US012697209B2

(12) United States Patent
Haynes et al.

(10) Patent No.: US 12,697,209 B2
(45) Date of Patent: Aug. 4, 2026

(54) SYSTEMS, DEVICES AND METHODS WITH STENT FRAME FEATURES

(71) Applicant: Capstan Medical Inc., Santa Cruz, CA (US)

(72) Inventors: Evelyn Haynes, Santa Cruz, CA (US); Ian Mahaffey, Santa Cruz, CA (US); Spencer Noe, Santa Cruz, CA (US); Dan Wallace, Santa Cruz, CA (US); Peter Gregg, Santa Cruz, CA (US)

(73) Assignee: Capstan Medical Inc., Santa Cruz, CA (US)

( * ) Notice: Subject to any disclaimer, the term of this patent is extended or adjusted under 35 U.S.C. 154(b) by 0 days.

(21) Appl. No.: 19/026,196

(22) Filed: Jan. 16, 2025

(65) Prior Publication Data

US 2025/0228663 A1 Jul. 17, 2025

Related U.S. Application Data

(60) Provisional application No. 63/621,496, filed on Jan. 16, 2024.

(51) Int. Cl.
A61F 2/24 (2006.01)
(52) U.S. Cl.
CPC .... A61F 2/2418 (2013.01); *A61F 2220/0075* (2013.01)
(58) Field of Classification Search
CPC ........ A61F 2/2418; A61F 2/2412; A61F 2/24; A61F 2/2427; A61F 2002/9534; A61F 2/95; A61F 2/2433; A61F 2/2439; A61F 2/2436; A61F 2220/0025; A61F 2002/9665; A61F 2002/9511; A61F 2/966
See application file for complete search history.

(56) References Cited

U.S. PATENT DOCUMENTS

| | | | | |
|---|---|---|---|---|
| 4,913,141 A | * | 4/1990 | Hillstead | A61F 2/88 623/1.11 |
| 5,035,706 A | * | 7/1991 | Giantureo | A61F 2/95 606/198 |
| 5,282,824 A | * | 2/1994 | Gianturco | A61F 2/86 623/1.13 |
| 5,375,612 A | * | 12/1994 | Cottenceau | A61F 2/0105 128/899 |
| 5,480,423 A | * | 1/1996 | Ravenscroft | A61F 2/95 623/1.11 |
| 5,554,181 A | * | 9/1996 | Das | A61F 2/88 623/1.11 |
| 5,800,521 A | * | 9/1998 | Orth | A61F 2/07 606/198 |
| 8,734,484 B2 | * | 5/2014 | Ahlberg | A61F 2/246 606/232 |

(Continued)

FOREIGN PATENT DOCUMENTS

| | | | | |
|---|---|---|---|---|
| WO | WO-2004017868 A1 | * | 3/2004 | A61F 2/966 |
| WO | WO-2008066923 A1 | * | 6/2008 | A61F 2/95 |

OTHER PUBLICATIONS

International Search Report and Written Opinion issued in International Application No. PCT/US2025/011940, mailed on Jun. 9, 2025, 15 pages,.

*Primary Examiner* — Seema Mathew
(74) *Attorney, Agent, or Firm* — Dorsey & Whitney LLP

(57) ABSTRACT

A replacement heart valve comprises one or more stent frame features, including inset barbs, ring attachment structures or attachment tabs.

24 Claims, 45 Drawing Sheets

(56)  References Cited

U.S. PATENT DOCUMENTS

| | | | | |
|---|---|---|---|---|
| 9,480,559 | B2 * | 11/2016 | Vidlund | .................. C08L 67/04 |
| 2006/0142836 | A1 * | 6/2006 | Hartley | ..................... A61F 2/95 |
| | | | | 623/1.11 |
| 2012/0310327 | A1 | 12/2012 | Mchugo | |
| 2014/0276979 | A1 * | 9/2014 | Sauer | ................. A61B 17/0487 |
| | | | | 606/232 |
| 2015/0039083 | A1 * | 2/2015 | Rafiee | ................ A61B 17/0401 |
| | | | | 623/2.37 |
| 2016/0278920 | A1 * | 9/2016 | Braido | .................. A61F 2/2487 |
| 2017/0156859 | A1 | 6/2017 | Chang et al. | |
| 2017/0165066 | A1 | 6/2017 | Rothstein | |
| 2018/0014955 | A1 | 1/2018 | Baxter et al. | |
| 2018/0116839 | A1 | 5/2018 | Mchugo et al. | |
| 2018/0116846 | A1 * | 5/2018 | McHugo | ................... A61F 2/95 |
| 2018/0125656 | A1 | 5/2018 | Bakis et al. | |
| 2019/0262129 | A1 | 8/2019 | Cooper et al. | |
| 2022/0313463 | A1 | 10/2022 | Li et al. | |
| 2023/0277307 | A1 | 9/2023 | Noe et al. | |
| 2025/0161052 | A1 * | 5/2025 | Spiegel | ................. A61F 2/2487 |

* cited by examiner

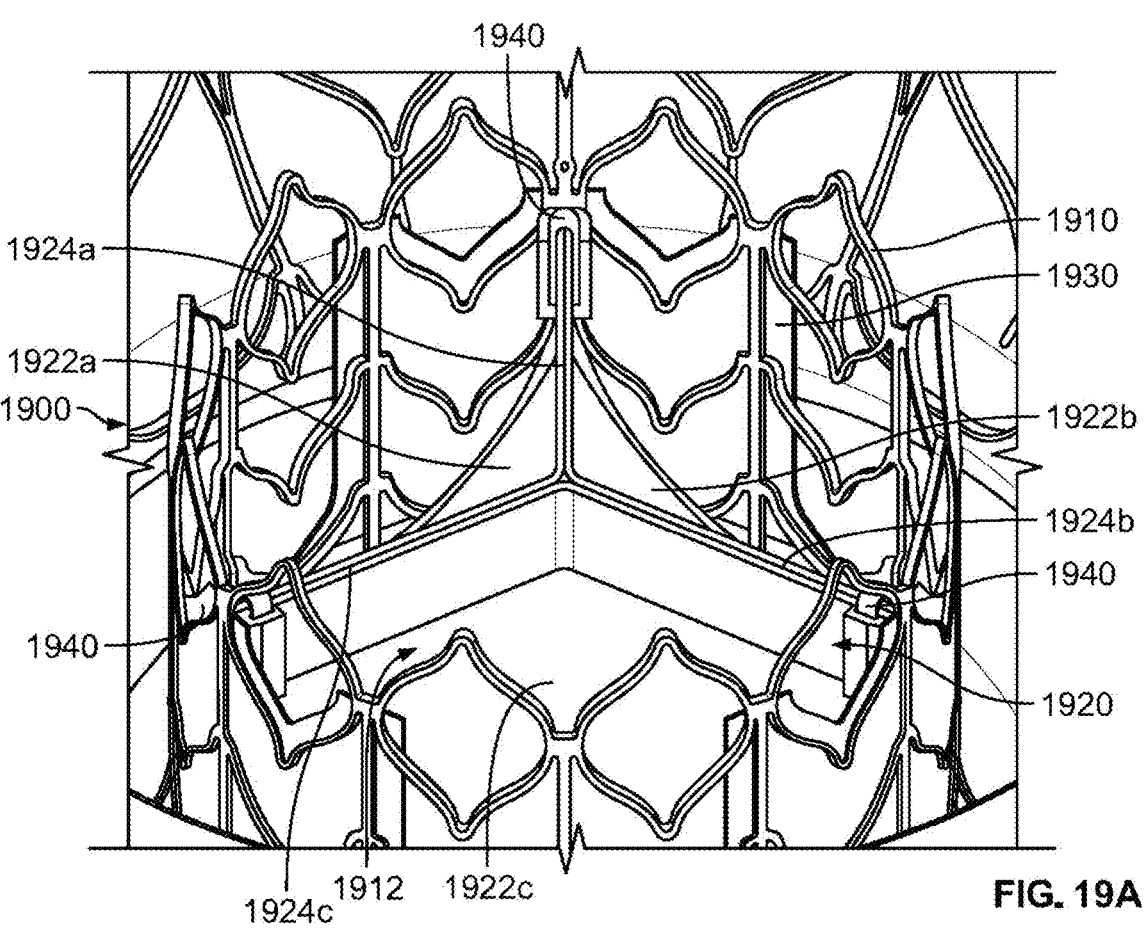
FIG. 19A
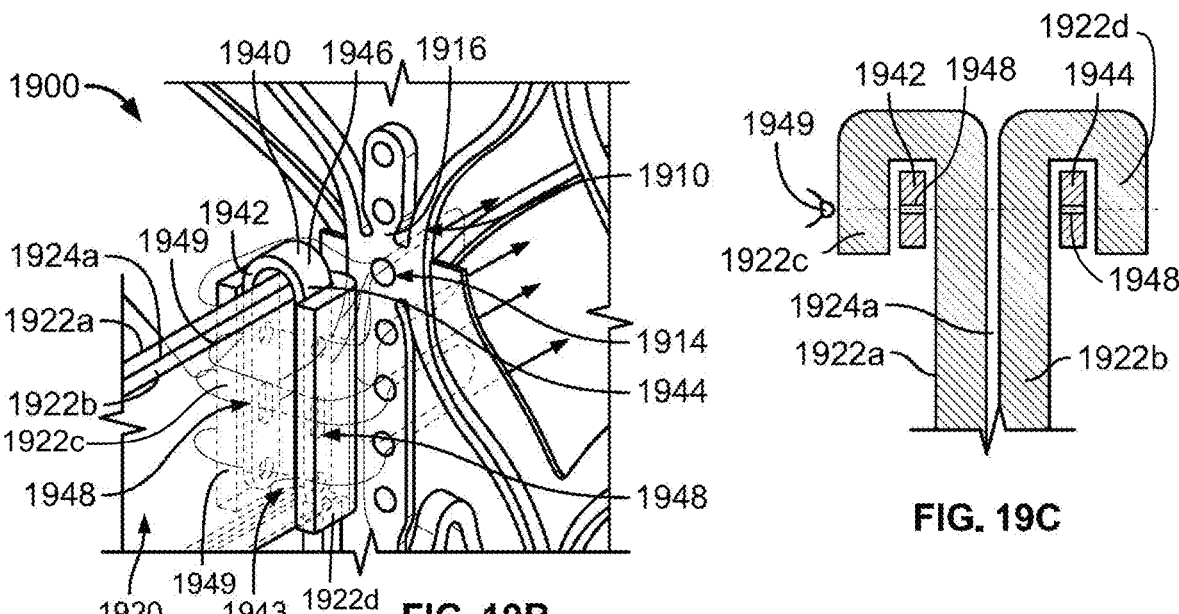
FIG. 19B
FIG. 19C

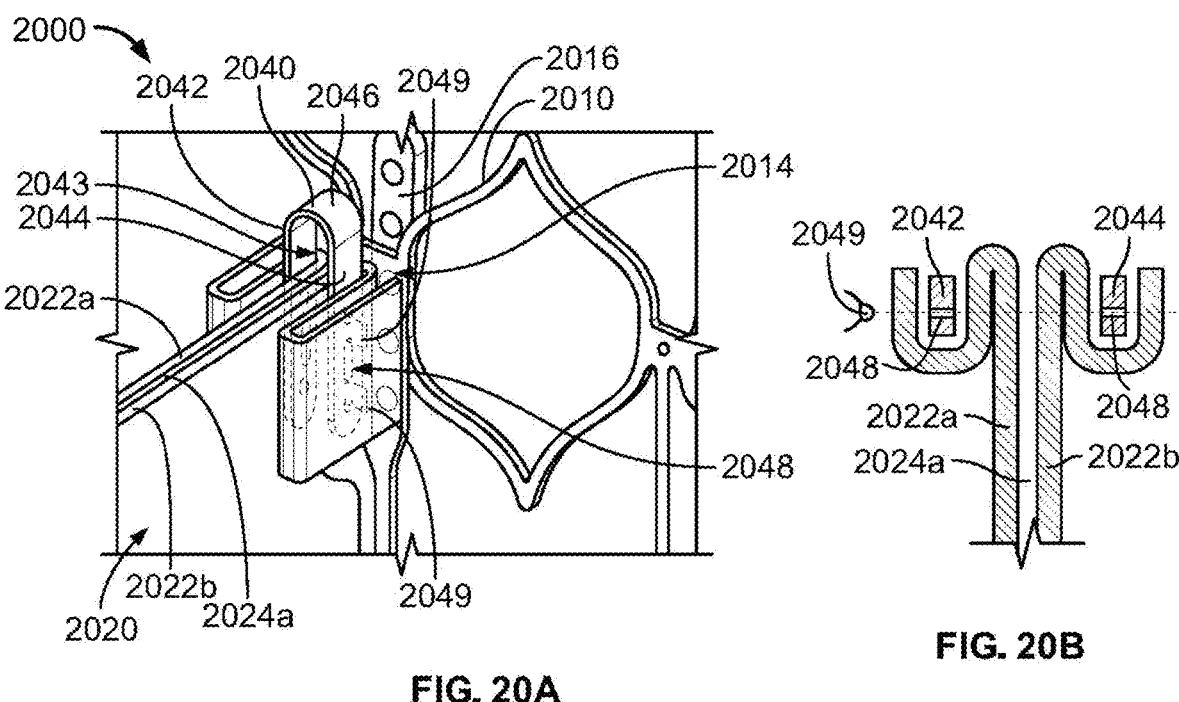
FIG. 20A
FIG. 20B
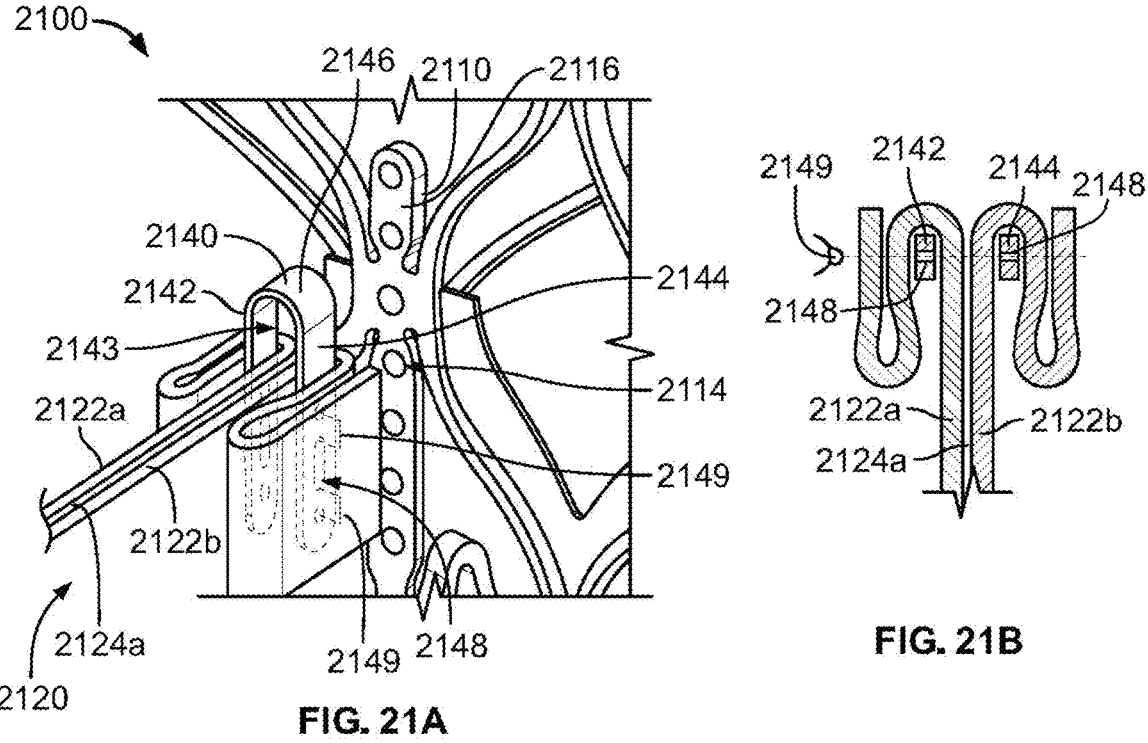
FIG. 21A
FIG. 21B

2300

2302

2350

2300

2302

2350

SYSTEMS, DEVICES AND METHODS WITH STENT FRAME FEATURES

RELATED APPLICATION(S)

This application claims priority under 35 U.S.C. § 119(c) to U.S. Application No. 63/621,496, filed Jan. 16, 2024, which is incorporated herein by reference, in its entirety, for any purpose.

BACKGROUND

This patent application relates generally to the treatment of valvular diseases, and more specifically to methods and apparatus for minimally invasive mitral valve replacement.

Valvular heart disease is a significant burden to patients and healthcare systems, with a prevalence of 2-3% worldwide, and with an increasing prevalence in aging populations. Valvular disease may result from a variety of etiologies, including autoimmune, infective and degenerative causes. The epidemiology of valvular disease also varies with the affected valve, with rheumatic heart disease being the cause worldwide of primary mitral regurgitation and mitral stenosis, but with secondary mitral disease from left ventricular dysfunction being more common in developed countries.

While surgical repair and valve replacement remains a mainstay of many mitral valve therapies in the current clinical guidelines by the American Heart Association and American College of Cardiology, transcatheter mitral repair is recommended for certain patient populations. In the 2017 Focused Update and the 2014 Guidelines for Management of Patients with Valvular Disease, the AHA/ACC recommended percutaneous mitral valve balloon commissurotomy for severe mitral valve stenosis, and transcatheter mitral valve repair in certain severely symptomatic patients with severe primary mitral regurgitation with a reasonable life expectancy who are non-surgical candidates due to comorbidities.

BRIEF SUMMARY

Further growth of transcatheter mitral valve therapies is challenged by the difficulty by mitral valve anatomy and physiology, compared to more established transcatheter aortic valve therapies. For example, some mitral valve replacement therapies in development make compromises between the sealing and anchoring properties of the outer portions of the replacement valve and the support of the leaflet valves. Other therapies attempt to address this challenge with two-part replacement valve structures, but these therapies may have high delivery failure rates or are too large for transcatheter delivery.

To address these issues, embodiments described herein are directed to a replacement heart valve comprising a unibody, folded, double-wall stent, with a stent cover and a leaflet valve attached to the inner lumen of the stent. The double wall stent structure decouples or reduces the effect on the geometry of the retention structure on the geometry of the valve support. This includes external forces acting through the valve annulus during the cardiac cycle, as well as the effect of non-circular valve annulus shapes. The double-wall stent structure also allows the valve support to have a different size and shape from outer annulus support, without having to conform to the native anatomy. This may reduce the risk of outflow track obstruction and/or impairment due to ventricular contraction, by permitting that the outer wall to have a shorter longitudinal length than the inner wall supporting the valve leaflets. The unibody design may also permit a greater structural integrity by reducing complications relating to force concentrations between joined, welded or mechanically connected support components and/ or their attachment in situ.

In some variations, this permits the contraction of the expandable valve to a size of less than 29 F, e.g., less than 10 mm, or between 24 F and 29 F, or between 8 mm and 10 mm. The heart valve may be delivered using a multi-pulley, suture-based stent restraint assembly on a catheter or delivery tool. Fixed guide openings or structures along the distal end of the delivery system that independently permits expansion of the distal and proximal ends of the outer wall of the stent via sutures passing through the openings. Control of the inner wall expansion may occur simultaneously with or occur independently from the expansion of the outer wall. The double-wall unibody design reduces the complexity over valves with multi-part structures while de-coupling the geometry of the valve support from the retention structure, while still providing a collapsibility suitable for transcatheter delivery.

In at least one example of the present disclosure, a replacement heart valve is provided comprising a unibody stent frame. The unibody stent frame comprises a plurality of longitudinal struts and a plurality of circumferential struts that form a tubular inner wall with a central lumen and an outer wall that surrounds the tubular inner wall. The replacement heart valve further includes a replacement leaflet valve located in the central lumen of the tubular inner wall and coupled to the tubular inner wall. The replacement valve further includes a bracket that couples to a commissure between two adjacent leaflets of the replacement leaflet valve and to one of the longitudinal struts of the tubular inner wall. The unibody stent frame of the replacement heart valve comprises a collapsed configuration and an expanded configuration.

In one example, the bracket comprises a U-shape with a first arm and a second arm that slides over the two adjacent leaflets and the commissure. A portion of each leaflet is disposed on an inner surface and an outer surface of the first arm and the second arm of the bracket. In one example, each arm of the bracket further comprises a plurality of apertures and the longitudinal strut comprises a plurality of apertures that enables the bracket to be sutured to the adjacent leaflets and to the longitudinal strut of the tubular inner wall. In one example, each leaflet comprises a layer within the bracket and a layer disposed outside of the bracket. In one example, each leaflet comprises two layers within the bracket and a layer disposed outside of the bracket. In one example, each leaflet comprises a layer within the bracket and two layers disposed outside of the bracket. In one example, a number of brackets of the replacement heart valve corresponds to the number of leaflets in the replacement leaflet valve. In one example, the replacement heart valve further includes a skirt that is disposed on the outer wall of the unibody stent frame. The skirt comprises a plurality of cutouts disposed on a lower edge of the skirt. In one example, the plurality of cutouts comprise an arc shape. In one example, each cutout of the plurality of cutouts are disposed between extensions of the skirt and each extension is aligned with a longitudinal strut of the outer wall of the unibody stent frame. In one embodiment, the replacement heart valve further includes a plurality of ring structures coupled to the unibody stent frame. Each ring structure of the plurality of ring structures includes a ring and an extension that extends from the ring. The extension comprises a plurality of apertures for lashing the ring structure to the unibody stent frame. In one example, the plurality of ring structures are coupled on an atrial side of the unibody stent frame. In one example, the plurality of longitudinal struts transition from straight longitudinal struts in the tubular inner wall to curved longitudinal struts in the outer wall via a transition wall between the outer wall and the tubular inner wall. In one example, the transition wall tapers at a predetermined angle relative to a longitudinal axis of the unibody stent frame. In one example, the plurality of longitudinal struts of the outer wall comprise a compound curve that transition from a concave curve to a convex curve to a concave curve to a convex curve to a concave curve. In one example, a first end region of the outer wall comprises circumferential struts that project radially outward from the outer wall.

In at least one example of the present disclosure, a replacement heart valve is provided comprising a unibody stent frame with a collapsed configuration and an expanded configuration. The unibody stent frame includes an inner wall defining a central lumen, an outer wall spaced radially apart from the inner wall, and a plurality of longitudinal struts. The plurality of longitudinal struts transition from straight longitudinal struts in the inner wall to curved longitudinal struts in the outer wall via a transition wall between the outer wall and the inner wall. The unibody stent frame further includes a plurality of inner circumferential struts that form the inner wall and a plurality of outer circumferential struts that form the outer wall. The unibody stent frame further includes a plurality of lateral projections that project radially outward from the outer wall and extend circumferentially around the outer wall of the unibody stent frame. Each lateral projection comprises a pair of angled legs that connect at an apex of the lateral projection. Each lateral projection comprises a compound curve with an inflection point that transitions each lateral projection from a concave curve where each lateral projection couples to the longitudinal strut of the outer wall to a convex curve. The replacement heart valve further includes a replacement leaflet valve location in the central lumen of the inner wall.

In one example, the plurality of longitudinal struts of the outer wall comprise a compound curve that transition from a concave curve to a convex curve to a concave curve to a convex curve to a concave curve.

In one example, of the present disclosure, a method of routing a suture to collapse a replacement valve includes obtaining a replacement valve. The replacement valve includes a unibody stent frame with a plurality of longitudinal struts and a plurality of circumferential struts that form a tubular inner wall with a central lumen and an outer wall that surrounds the tubular inner wall. The replacement valve further includes a replacement leaflet valve located in the central lumen of the tubular inner wall and coupled to the tubular inner wall. The replacement valve further includes twelve rings coupled to the unibody stent frame equally space around a circumference of the unibody stent frame disposed at the twelve hour positions of an analog clock. The method includes tying a first segment of the suture to a sixth ring, threading the first segment of the suture clockwise through a seventh ring, an eighth ring, a ninth ring, skipping a tenth ring, threading the first segment of the suture clockwise through an eleventh ring, a twelfth ring, a first ring, and trying the first segment of the suture to a second ring. The method further includes threading a second segment of the suture clockwise through a third ring, a fourth ring, a fifth ring, skipping the sixth ring, threading the second segment of the suture clockwise through the seventh ring, the eighth ring, the ninth ring, and tying the second segment of the suture to the tenth ring. The method further includes threading a third segment of the suture clockwise through the eleventh ring, the twelfth ring, the first ring, skipping the second ring, threading the third segment of the suture clockwise through the third ring, the fourth ring, and the fifth ring, and trying the third segment of the suture to the sixth ring.

In one example of the present disclosure, a method of routing a suture to collapse a replacement valve includes obtaining a replacement valve. The replacement valve includes a unibody stent frame, the unibody stent frame comprising a plurality of longitudinal struts and a plurality of circumferential struts that form a tubular inner wall with a central lumen and an outer wall that surrounds the tubular inner wall. The replacement valve further includes a replacement leaflet valve located in the central lumen of the tubular inner wall and coupled to the tubular inner wall. The replacement valve further includes twelve rings coupled to the unibody stent frame equally space around a circumference of the unibody stent frame disposed at the twelve hour positions of an analog clock. The method includes tying a first segment of the suture to a fifth ring, threading the first segment of the suture clockwise through a sixth ring, a seventh ring, an eighth ring, a ninth ring, skipping a tenth ring, threading the first segment of the suture counterclockwise through an eleventh ring, the tenth ring, and tying the first segment of the suture to the ninth ring. The method further includes threading a second segment of the suture clockwise through the tenth ring, the eleventh ring, a twelfth ring, a first ring, skipping a second ring, threading the second segment of the suture counterclockwise through a third ring, the second ring, and tying the second segment of the suture to the first ring. The method further includes threading a third segment of the suture clockwise through the second ring, the third ring, a fourth ring, the fifth ring, skipping the sixth ring, threading the third segment of the suture counterclockwise through the seventh ring, the sixth ring, and typing the third segment to the fifth ring.

In one example, a replacement heart valve is provided, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, and a bracket that couples to a commissure between two adjacent leaflets of the replacement leaflet valve and to one of the longitudinal struts of the tubular inner wall, wherein the unibody stent frame comprises a collapsed configuration and an expanded configuration. The bracket may comprise a U-shape with a first arm and a second arm that slides over the two adjacent leaflets and the commissure, wherein a portion of each leaflet is disposed on an inner surface and an outer surface of the first arm and the second arm of the bracket. Each arm of the bracket may further comprise a plurality of apertures and the longitudinal strut comprises a plurality of apertures that enables the bracket to be sutured to the adjacent leaflets and to the longitudinal strut of the tubular inner wall. Each leaflet may comprise a layer within the bracket and a layer disposed outside of the bracket, two layers within the bracket and a layer disposed outside of the bracket, and/or a layer within the bracket and two layers disposed outside of the bracket. A number of brackets may correspond to the number of leaflets in the replacement leaflet valve. The replacement heart valve may further comprise a skirt that is disposed on the outer wall of the unibody stent frame, wherein the skirt comprises a plurality of cutouts disposed on a lower edge of the skirt. The plurality of cutouts may comprise an arc or arcuate shape. Each cutout of the plurality of cutouts may be disposed between extensions of the skirt, and wherein each extension is aligned with a longitudinal strut of the outer wall of the unibody stent frame. The replacement heart valve may further comprise a plurality of ring structures coupled to the unibody stent frame, wherein each ring structure of the plurality of ring structures comprises a ring, and an extension that extends from the ring, wherein the extension comprises a plurality of apertures for lashing the ring structure to the unibody stent frame. The plurality of ring structures may be coupled on an atrial side of the unibody stent frame. The plurality of longitudinal struts may transition from straight longitudinal struts in the tubular inner wall to curved longitudinal struts in the outer wall via a transition wall between the outer wall and the tubular inner wall. The transition wall may taper at a predetermined angle relative to a longitudinal axis of the unibody stent frame. The plurality of longitudinal struts of the outer wall may comprise a compound curve that transition from a concave curve to a convex curve to a concave curve to a convex curve to a concave curve. A first end region of the outer wall may comprise circumferential struts that project radially outward from the outer wall.

In another example, a replacement heart valve may be provided, comprising a unibody stent frame with a collapsed configuration and an expanded configuration, the unibody stent frame comprising an inner wall defining a central lumen, an outer wall spaced radially apart from the inner wall, a plurality of longitudinal struts, wherein the plurality of longitudinal struts transition from straight longitudinal struts in the inner wall to curved longitudinal struts in the outer wall via a transition wall between the outer wall and the inner wall, a plurality of inner circumferential struts that form the inner wall and a plurality of outer circumferential struts that form the outer wall, and a plurality of lateral projections that project radially outward from the outer wall and extend circumferentially around the outer wall of the unibody stent frame, wherein each lateral projection comprises a pair of angled legs that connect at an apex of the lateral projection, wherein the lateral projection comprises a compound curve with an inflection point that transitions each lateral projection from a concave curve where each lateral projection couples to the longitudinal strut of the outer wall to a convex curve, and a replacement leaflet valve location in the central lumen of the inner wall. The plurality of longitudinal struts of the outer wall may comprise a compound curve that transition from a concave curve to a convex curve to a concave curve to a convex curve to a concave curve.

In another exemplary embodiment, a method of routing a suture to collapse a replacement valve may be provided, comprising obtaining a replacement valve, the valve comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, a plurality of rings coupled to the unibody stent frame equally space around a circumference of the unibody stent frame, attaching a first segment of the suture to a first anchor ring, threading the first segment of the suture through a first subset of rings comprising at least one consecutive ring immediately adjacent to the first attached ring, skipping a second anchor ring immediately adjacent to the first set of threaded rings, threading the first segment of the suture through a second subset of rings comprising at least one consecutive threaded ring immediately adjacent to the second anchor ring, and attaching the first segment of the suture to a third anchor ring immediately adjacent to the second threaded set of rings, threading a second segment of the suture through a third subset of threaded rings comprising at least one consecutive ring immediately adjacent to the third anchor ring, skipping the first anchor ring, threading the second segment of the suture through the first set of threaded rings, and tying the second segment of the suture to the second anchor ring, and threading a third segment of the suture through the second subset of rings, skipping the third anchor ring, threading the third segment of the suture through the third subset of rings, and attaching the third segment of the suture to the first anchoring. The first, second and third subsets of rings may each contain the same number of rings. The plurality of rings may comprise twelve rings, and wherein the first anchor ring is the sixth ring of the plurality of rings, the first subset of rings comprises the seventh, eighth and ninth rings of the plurality of rings, the second anchor ring is the tenth ring of the plurality of rings, the second subset of rings comprises the eleventh, twelfth and first rings of the plurality of rings, the third anchor ring is the second ring of the plurality of rings, and the third subset of rings comprises the third, fourth and fifth rings of the plurality of rings. The plurality of rings may comprise N rings and X subset of rings, wherein N is wholly divisible by X+1. Each of the X of subset of rings may comprises Y rings. In some further embodiments, each of the X of subset of rings may not overlap with any other X subset of rings. In some specific embodiments, Y=3 and N=12.

In another embodiment, a method of routing a suture to collapse a replacement valve I provided, comprising obtaining a replacement valve comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, a plurality of rings coupled to the unibody stent frame equally space around a circumference of the unibody stent, tying a first segment of the suture to a first anchor ring, threading the first segment of the suture in a first direction through a first X consecutive rings immediately adjacent to the first anchor ring, skipping a second anchor ring immediately adjacent to the first subset of consecutive rings, threading the first segment of the suture in a second direction through a first Y consecutive rings that is less in number than X consecutive rings, and tying the first segment of the suture to the ring of the first X consecutive rings closet to the second anchor ring, threading a second segment of the suture in the first direction through the second anchor ring and a second X consecutive rings immediately adjacent to the second anchor ring, skipping a third anchor ring immediately adjacent to the second X consecutive rings, threading the second segment of the suture in the second direction through a second Y consecutive rings that is less in number than X consecutive rings, and, and tying the second segment of the suture to the ring of the second X consecutive rings that is closest to the third anchor ring, threading a third segment of the suture in the first direction through the third anchor ring and third X consecutive rings immediately adjacent to the third anchor ring, skipping the fourth anchor ring immediately adjacent to the third X consecutive rings, threading the third segment of the suture in the second direction through a third Y consecutive rings, wherein Y<X, and tying the third segment to the first anchor ring. The plurality of rings may comprise N rings, and wherein N is wholly divisible by X. In some further embodiments, Y=0, or Y=2 and X=4.

In another example, a method of routing a suture to collapse a replacement valve, comprising obtaining a replacement valve is provided, the valve comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, and a plurality of rings coupled to the unibody stent frame equally space around a circumference of the unibody stent wherein the relative positions of rings are defined by positive and negative directions, then tying a first segment of the suture to a first anchor ring, threading the first segment of the suture in a first direction through a first X consecutive rings immediately adjacent to the first anchor ring, wherein X>0, skipping in the first direction Y rings immediately adjacent to the first X consecutive rings, threading in the second direction Z consecutive rings, wherein Z is zero or greater than one, and Z<X, and tying the first segment of the suture to the next consecutive ring in the first direction if Z=0, or the next consecutive rings in the second direction if Z>0, threading a second segment of the suture in the first direction a second X consecutive rings, skipping in the first direction Y rings immediately adjacent to the second X consecutive rings, threading in the second direction Z consecutive rings, wherein Z is zero or greater than one, and Z<X, and tying the second segment of the suture to the next consecutive ring from the second X consecutive rings in the first direction if Z=0, or the next consecutive rings in the second direction if Z>0, threading a third segment of the suture in the first direction a third X consecutive rings, skipping in the first direction Y rings immediately adjacent to the third X consecutive rings, threading in the second direction Z consecutive rings, wherein Z is zero or greater than one, and Z<X, and tying the third segment of the suture to the next consecutive ring from the third X consecutive rings in the first direction if Z=0, or the next consecutive rings in the second direction if Z>0. In some further variations, the suture patterns may be configured such that X=3 and Y=1 and Z=0, wherein X=4 and Y=1 and Z=2, wherein X>2, or wherein X−Z=2.

In one embodiment, a stent assembly is provided, comprising an expandable stent, the expandable stent comprising an arrangement of struts forming an outer wall, the outer wall comprising a first end region, a second end region and a middle region therebetween, a plurality of tether retention structures arranged circumferentially around the first end region of the stent and defining a circumferential tether path, a plurality of tether path locations uniformly spaced along the circumferential tether path, wherein each of the tether retention structures may be located at one of the tether path locations, and wherein each tether path location includes, and a plurality of tether lines, wherein each tether line of the plurality of tether lines may comprise a main region located along the circumferential tether path and a loop that loops away from the circumferential tether path between two tether retention structures, and wherein each tether line of the plurality of tether lines overlaps at least one other tether line of the plurality of tether lines along the circumferential tether path. The main region of each tether line of the plurality of tether lines may comprise a first end region with a first end, and a second end region with a second end, and a middle region therebetween and containing its loop. Each first end and second end of each tether line may be fixedly attached to one of the plurality of tether path locations, either directly to the outer wall or to a tether retention structure. Each tether path location may comprise at least one tether retention structure, and wherein at least one tether path location may comprise two tether retention structures, wherein the middle region of one of the tether lines may be configured to slidably pass through the two tether retention structures the loop of the one tether line loop away from the circumferential tether path between the two tether retention structures. The at least one tether path location comprising two tether retention structures may comprise a plurality of tether path locations with two tether retention structures corresponding in number to the plurality of tether lines. Each first end region and each second end region of each tether line may slidably pass through at least one first tether retention structure at a tether path location that may be different from the tether path location of the corresponding first end and second end, respectively. Each of the plurality of tether path locations that is fixedly attached to the first end or the second end of one of the tether lines may not fixedly attached to any other tether lines. Each tether retention structure that may be fixedly attached to the first end or the second end of one of the tether lines may be also slidably passed through by a different tether line. Each of the plurality of tether lines may be configured to slidably pass through one of the plurality of tether retention structures without any other of the first tether lines slidably passing through or attached thereto, may slidably pass through one of the plurality of tether retention structures along with another of the tether lines also slidably passing through, and may be fixedly attached to two of the tether retention structures that are also slidably passed through by another of the first tether lines. The number of tether path locations may be a multiple of three and the plurality of first tether lines may comprise three tether lines. The number of tether path locations may comprise twelve tether path locations. The twelve tether path locations may be consecutive tether path locations comprising a first, second, third, fourth, fifth, sixth, seventh, eighth, ninth, tenth, eleventh and twelfth path locations, and wherein the fourth, eighth and twelfth tether path locations each may comprise two first tether retention structures, and the first, second, third, fifth, sixth, seventh, ninth, tenth and eleventh tether path locations each may comprise one first tether retention structure. Each tether line of the plurality of tether lines may overlap at least two other tether lines of the plurality of tether lines along the circumferential tether path. The plurality of tether retention structures may be a plurality of first tether retention structures, and wherein the circumferential tether path may be a first circumferential tether path, the plurality of tether path locations are a plurality of first tether path locations, and wherein the stent assembly further may comprise a plurality of second tether retention structures arranged circumferentially around the second end region of the expandable stent and defining a second circumferential tether path, a plurality of second tether path locations uniformly spaced along the second circumferential tether path, wherein each of the second tether retention structures may be located at one of the first tether path locations, and wherein each second tether path location may contain either no second tether retention structure, one second tether retention structure, or two second retention structures, a plurality of second tether lines, wherein each second tether line of the plurality of second tether lines may comprise a main region located along the circumferential tether path and a loop that loops away from the circumferential tether path between two tether retention structures. Each second tether line of the plurality of second tether lines may overlap at least one other second tether line of the plurality of second tether lines along the second circumferential tether path. The main region of each tether line of the plurality of tether lines may comprise a first end region with a first end, and a second end region with a second end, and a middle region therebetween and containing its loop. Each first end and each second end of each second tether line may be fixedly attached to one of the plurality of second tether path locations either directly to a strut of the outer wall, or a second tether retention structure. The plurality of second tether lines may comprise a non-overlapping arrangement. The plurality of second tether lines may comprise an overlapping arrangement. The relative configurations of the plurality of first tether retention structures and the plurality of first tether lines along the first circumferential tether path may be identical to the relative configuration of the plurality of second tether retention structures and the plurality of second tether lines along the second circumferential tether path. The stent further may comprise an inner wall and a transition wall between the inner wall and the transition wall, wherein the transition wall may be located in the first end region of the stent. Each of the plurality of tether retention structures may comprise an opening with a transverse or tangential orientation to the outer wall of the stent. Each of the plurality of tether retention structures may comprise rings, hoops or clips. Each of the plurality of tether retention structures may be fixedly attached or contiguously formed with the outer wall of the stent. Each of the plurality of tether retention structures may be movably or pivotably attached to the outer wall of the stent via sutures or wires. The stent assembly further may comprise a stent cover, and wherein each of the plurality of first tether retention structures may be also attached to the stent cover via the sutures or wires. Each of the plurality of tether path locations may be located at a longitudinal strut of the arrangement of struts. At least one of the first end region and second end region of each tether line of the plurality of tether lines may overlap itself along the circumferential tether path. At least one of the plurality of tether path locations may lack a tether retention structure. The at least one of the plurality of tether path locations may lack a tether retention structure corresponds in number to the plurality of tether lines. Each of the first plurality of tether retention structures may project radially outward from the outer wall of the stent.

In another variation, a replacement heart valve is provided, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, and a bracket coupled to a commissure between two adjacent leaflets of the replacement leaflet valve and to the tubular inner wall, wherein the unibody stent frame may comprise a collapsed configuration and an expanded configuration. The bracket may comprise a U-shape with a first arm and a second arm that slides over the two adjacent leaflets and the commissure, wherein a portion of each leaflet may be disposed on an inner surface and an outer surface of the first arm and the second arm of the bracket. Each arm of the bracket further may comprise a plurality of apertures and a longitudinal strut of the plurality of longitudinal struts may comprise a plurality of apertures, and wherein the bracket may be sutured to the adjacent leaflets and to the longitudinal strut. The bracket may be sutured to the adjacent leaflets with at least one suture, and wherein each suture of the at least one suture may be looped through an aperture of the plurality of apertures of the longitudinal strut of the plurality of longitudinal struts, through an everted layer of one of the adjacent leaflet, through a corresponding aperture of the first arm of the bracket, through apposed layers of the adjacent leaflets, through a corresponding aperture of the second arm of the bracket, through the everted layer of the other adjacent leaflet, and back through the first aperture of the plurality of apertures of the longitudinal strut of the plurality of longitudinal struts. Each suture may be further passed through an adjacent aperture to the of the plurality of apertures of the longitudinal strut of the plurality of longitudinal struts, through the everted layer of the one of the adjacent leaflet, through an adjacent corresponding aperture of the first arm of the bracket, through the apposed layers of the adjacent leaflets, through an adjacent corresponding aperture of the second arm of the bracket, through the everted layer of the other adjacent leaflet, and back through the adjacent aperture of the plurality of apertures of the longitudinal strut of the plurality of longitudinal struts. Each leaflet may comprise a layer within the bracket and a layer disposed outside of the bracket. Each leaflet may comprise two layers within the bracket and a layer disposed outside of the bracket. Each leaflet may comprise a layer within the bracket and two layers disposed outside of the bracket. A number of brackets may correspond to the number of leaflets in the replacement leaflet valve. The leaflet valve may be a tri-leaflet valve and the number of brackets may be three. The replacement heart valve may further comprise a skirt that may be disposed on the outer wall of the unibody stent frame, wherein the skirt may comprise a plurality of cutouts disposed on a lower edge of the skirt. The plurality of cutouts may comprise an arc shape. Each cutout of the plurality of cutouts may be disposed between extensions of the skirt, and wherein each extension may be aligned with a longitudinal strut of the outer wall of the unibody stent frame. The stent frame further may comprise a plurality of tissue barbs formed within the longitudinal struts and surrounded by an elongate cavity. The skirt further may comprise pre-formed elongate slots corresponding to locations of the plurality of tissue barbs. The replacement heart valve may further comprise a plurality of ring structures coupled to the unibody stent frame, wherein each ring structure of the plurality of ring structures may comprise a ring, and an extension that extends from the ring, wherein the extension may comprise a plurality of apertures for lashing the ring structure to the unibody stent frame. The plurality of ring structures may be coupled on an atrial side of the unibody stent frame. The plurality of longitudinal struts may transition from straight longitudinal struts in the tubular inner wall to curved longitudinal struts in the outer wall via a transition wall between the outer wall and the tubular inner wall. The transition wall may taper at a predetermined angle relative to a longitudinal axis of the unibody stent frame. The plurality of longitudinal struts of the outer wall may comprise a compound curve that transition from a concave curve to a convex curve to a concave curve to a convex curve to a concave curve. A first end region of the outer wall may comprise circumferential struts that project radially outward from the outer wall.

In another embodiment, a replacement heart valve may be provided, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, and a skirt that may be disposed on the outer wall of the unibody stent frame, wherein the skirt may comprise a plurality of cutouts disposed on a lower edge of the skirt wherein the unibody stent frame may comprise a collapsed configuration and an expanded configuration. The plurality of cutouts may comprise an arc shape. Each cutout of the plurality of cutouts may be disposed between extensions of the skirt, and wherein each extension may be aligned with a longitudinal strut of the outer wall of the unibody stent frame. Each extension of the skirt may comprise a rectangular shape. The stent frame further may comprise a plurality of tissue barbs formed within the longitudinal struts and surrounded by an elongate cavity. The skirt further may comprise pre-formed elongate slots corresponding to locations of the plurality of tissue barbs.

In still another embodiment, a replacement heart valve is provided, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, and wherein the unibody stent frame may comprise a collapsed configuration and an expanded configuration. The replacement heart may further comprise a plurality of ring structures coupled to the unibody stent frame, wherein each ring structure of the plurality of ring structures may comprise a ring, and an extension that extends from the ring, wherein the extension may comprise a plurality of apertures for lashing the ring structure to the unibody stent frame. The plurality of ring structures may be coupled on an atrial side of the unibody stent frame. The plurality of longitudinal struts may transition from straight longitudinal struts in the tubular inner wall to curved longitudinal struts in the outer wall via a transition wall between the outer wall and the tubular inner wall. The transition wall may taper at a predetermined angle relative to a longitudinal axis of the unibody stent frame. The plurality of longitudinal struts of the outer wall may comprise a compound curve that transition from a concave curve to a convex curve to a concave curve to a convex curve to a concave curve. A first end region of the outer wall may comprise circumferential struts that project radially outward from the outer wall.

In another variation, a replacement heart valve is provided, comprising a unibody stent frame with a collapsed configuration and an expanded configuration, the unibody stent frame comprising an inner wall defining a central lumen, an outer wall spaced radially apart from the inner wall, a plurality of longitudinal struts, wherein the plurality of longitudinal struts transition from straight longitudinal struts in the inner wall to curved longitudinal struts in the outer wall via a transition wall between the outer wall and the inner wall, a plurality of inner circumferential struts that form the inner wall and a plurality of outer circumferential struts that form the outer wall, a plurality of lateral projections that project radially outward from the outer wall and extend circumferentially around the outer wall of the unibody stent frame, wherein each lateral projection may comprise a pair of angled legs that connect at an apex of the lateral projection, wherein the lateral projection may comprise a compound curve with an inflection point that transitions each lateral projection from a concave curve where each lateral projection couples to the longitudinal strut of the outer wall to a convex curve, and a replacement leaflet valve location in the central lumen of the inner wall. The plurality of longitudinal struts of the outer wall may comprise a compound curve that transition from a concave curve to a convex curve to a concave curve to a convex curve to a concave curve.

In another embodiment, a stent valve may be provided, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, a plurality of rings coupled to the unibody stent frame equally space around a circumference of the unibody stent frame, the plurality of rings comprising a first anchor ring, a first subset of rings comprising at least one consecutive ring immediately adjacent to the first anchor ring, a second anchor ring immediately agent to the first subset of rings, and a second subset of rings comprising at least one consecutive ring immediately adjacent to the second anchor ring, subset of consecutive rings, a third anchor ring immediately adjacent to the second set of rings, a third subset of rings comprising at least one consecutive ring immediately adjacent to the third anchor ring, a first suture segment attached to the first anchor ring and threaded through the first subset of rings and the second subset of rings while skipping the second anchor ring, and attached the third anchor ring, a second suture segment attached to the third anchor ring and threaded through the third subset of rings and the first subset of rings while skipping the first anchor ring, and attached to the second anchor ring, and a third suture segment attached to the second anchor ring and threaded through the second subset of rings and the third subset of rings while skipping the third anchor ring, and attached to the first anchor ring. The first suture segment, second suture segment and third suture segment may comprise one contiguous suture. The first suture segment, second suture segment and third suture segment may comprise separate sutures. The first, second and third subsets of rings each may contain the same number of rings. The plurality of rings may comprise twelve rings, and wherein the first anchor ring may be the sixth ring of the plurality of rings, the first subset of rings may comprise the seventh, eighth and ninth rings of the plurality of rings, the second anchor ring may be the tenth ring of the plurality of rings, the second subset of rings may comprise the eleventh, twelfth and first rings of the plurality of rings, the third anchor ring may be the second ring of the plurality of rings, and the third subset of rings may comprise the third, fourth and fifth rings of the plurality of rings. The plurality of rings may comprise N rings and X subset of rings, wherein N may be wholly divisible by X+1. The each of the X of subset of rings may comprise Y rings. Each of the X of subset of rings may not overlap with any other X subset of rings. The values may be Y=3 and N=12.

In another embodiment, a stent valve is provided, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, a plurality of rings coupled to the unibody stent frame equally space around a circumference of the unibody stent wherein the relative positions of rings are defined by positive and negative directions, a first suture segment attached to a first anchor ring of the plurality of rings and threaded in a first direction through a first X consecutive rings of the plurality of rings immediately adjacent to the first anchor ring, wherein X>0, skipping in the first direction Y rings immediately adjacent to the first X consecutive rings, and threaded in the second direction through Z consecutive rings of the plurality of rings, wherein Z may be zero or greater than one, and Z<X, and attached to the next consecutive ring of the plurality of rings in the first direction if Z=0, or the next consecutive rings of the plurality of rings in the second direction if Z>0, a second suture segment attached to the same ring as the first segment of suture that may be not the first anchor ring, and threaded in the first direction through a second X consecutive rings of the plurality of rings, skipping in the first direction Y rings of the plurality of rings immediately adjacent to the second X consecutive rings, threaded in the second direction Z consecutive rings of the plurality of rings, wherein Z may be zero or greater than one, and Z<X, and attached to the next consecutive ring of the plurality of rings from the second X consecutive rings in the first direction if Z=0, or the next consecutive rings of the plurality of rings in the second direction if Z>0, and a third suture segment attached to the same ring as the second suture segment corresponding to the next consecutive ring from the second X consecutive rings in the first direction if Z=0, or the next consecutive rings in the second direction if Z>0 in the first direction, and threaded through a third X consecutive rings of the plurality of rings, skipping in the first direction Y rings immediately adjacent to the third X consecutive rings, threaded in the second direction Z consecutive rings of the plurality of rings, wherein Z may be zero or greater than one, and Z<X, and attached to the next consecutive ring from the third X consecutive rings in the first direction if Z=0, or the next consecutive rings in the second direction if Z>0. The values, may be X=3, Y=1 and Z=0, or X=4, Y=1 and Z=2, or X>2, or X−Z=2. The first suture segment, second suture segment and third suture segment may comprise serially consecutive segments of one contiguous suture. The first suture segment, second suture segment and third suture segment may comprise separate sutures.

In still another embodiment, a stent valve is provided, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, a plurality of rings coupled to the unibody stent frame equally space around a circumference of the unibody stent, a first segment of the suture tied to a first anchor ring of the plurality of rings, the first segment of the suture threaded in a first direction through a first X consecutive rings of the plurality of rings immediately adjacent to the first anchor ring, skipping a second anchor ring of the plurality of rings immediately adjacent to the first subset of consecutive rings, threaded in a second direction through a first Y consecutive rings of the plurality of rings that may be less in number than X consecutive rings, and tied t to the ring of the plurality of rings of the first X consecutive rings closet to the second anchor ring, a second segment of the suture threaded in the first direction through the second anchor ring and a second X consecutive rings of the plurality of rings immediately adjacent to the second anchor ring, skipping a third anchor ring of the plurality of rings immediately adjacent to the second X consecutive rings, threaded the second direction through a second Y consecutive rings of the plurality of rings that may be less in number than X consecutive rings, and, and tied to the ring of the second X consecutive rings that may be closest to the third anchor ring, a third segment of the suture threaded in the first direction through the third anchor ring and third X consecutive rings immediately adjacent to the third anchor ring, skipping the fourth anchor ring of the plurality of rings immediately adjacent to the third X consecutive rings, threading the third segment of the suture in the second direction through a third Y consecutive rings of the plurality of rings, wherein Y<X, and tying the third segment to the first anchor ring. The plurality of rings may comprise N rings, and wherein N may be wholly divisible by X. The values may correspond to Y=0, or wherein Y=2 and X=4.

In another embodiment, a method of routing a suture to collapse a replacement valve comprising obtaining a replacement valve is provided, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, and a plurality of rings coupled to the unibody stent frame equally space around a circumference of the unibody stent frame, the plurality of rings comprising a first anchor ring, a first subset of rings, a second anchor ring, a second subset of rings, a third anchor ring and a third subset of rings, attaching a first segment of the suture to the first anchor ring, threading the first segment of the suture through the first subset of rings comprising at least one consecutive ring immediately adjacent to the first anchor ring, skipping the second anchor ring immediately adjacent to the first set of rings, threading the first segment of the suture through the second subset of rings comprising at least one consecutive threaded ring immediately adjacent to the second anchor ring, and attaching the first segment of the suture to a third anchor ring immediately adjacent to the second subset set of rings, threading a second segment of the suture through the third subset of rings comprising at least one consecutive ring immediately adjacent to the third anchor ring, skipping the first anchor ring, threading the second segment of the suture through the first set of rings, and tying the second segment of the suture to the second anchor ring, threading a third segment of the suture through the second subset of rings, skipping the third anchor ring, threading the third segment of the suture through the third subset of rings, and attaching the third segment of the suture to the first anchoring ring. The first, second and third subsets of rings each contain the same number of rings. The plurality of rings may comprise twelve rings, and wherein the first anchor ring may be the sixth ring of the plurality of rings, the first subset of rings may comprise the seventh, eighth and ninth rings of the plurality of rings, the second anchor ring may be the tenth ring of the plurality of rings, the second subset of rings may comprise the eleventh, twelfth and first rings of the plurality of rings, the third anchor ring may be the second ring of the plurality of rings, and the third subset of rings may comprise the third, fourth and fifth rings of the plurality of rings. The plurality of rings may comprise N rings and X subset of rings, wherein N may be wholly divisible by X+1. Each of the X of subset of rings may comprise Y rings. Each of the X of subset of rings do not overlap with any other X subset of rings. The values may be Y=3 and N=12.

In another variation, a method of routing a suture to collapse a replacement valve is provided, comprising obtaining a replacement valve, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, a plurality of rings coupled to the unibody stent frame equally space around a circumference of the unibody stent, tying a first segment of the suture to a first anchor ring of the plurality of rings, threading the first segment of the suture in a first direction through a first X consecutive rings of the plurality of rings immediately adjacent to the first anchor ring, skipping a second anchor ring of the plurality of rings immediately adjacent to the first subset of consecutive rings, threading the first segment of the suture in a second direction through a first Y consecutive rings of the plurality of rings that may be less in number than X consecutive rings, and tying the first segment of the suture to the ring of the plurality of rings of the first X consecutive rings closet to the second anchor ring, threading a second segment of the suture in the first direction through the second anchor ring and a second X consecutive rings of the plurality of rings immediately adjacent to the second anchor ring, skipping a third anchor ring of the plurality of rings immediately adjacent to the second X consecutive rings, threading the second segment of the suture in the second direction through a second Y consecutive rings of the plurality of rings that may be less in number than X consecutive rings, and, and tying the second segment of the suture to the ring of the second X consecutive rings that may be closest to the third anchor ring, threading a third segment of the suture in the first direction through the third anchor ring and third X consecutive rings immediately adjacent to the third anchor ring, skipping the fourth anchor ring of the plurality of rings immediately adjacent to the third X consecutive rings, threading the third segment of the suture in the second direction through a third Y consecutive rings of the plurality of rings, wherein Y<X, and tying the third segment to the first anchor ring. The plurality of rings may comprise N rings, and wherein N may be wholly divisible by X. The values may be Y=0, or wherein Y=2 and X=4.

In another embodiment, a method of routing a suture to collapse a replacement valve is provided, comprising obtaining a replacement valve, comprising a unibody stent frame, the unibody stent frame comprising a plurality of longitudinal struts and a plurality of circumferential struts that form a tubular inner wall with a central lumen and an outer wall that surrounds the tubular inner wall, a replacement leaflet valve located in the central lumen of the tubular inner wall and coupled to the tubular inner wall, a plurality of rings coupled to the unibody stent frame equally space around a circumference of the unibody stent wherein the relative positions of rings are defined by positive and negative directions, tying a first segment of the suture to a first anchor ring, threading the first segment of the suture in a first direction through a first X consecutive rings immediately adjacent to the first anchor ring, wherein X>0, skipping in the first direction Y rings immediately adjacent to the first X consecutive rings, threading in the second direction Z consecutive rings, wherein Z may be zero or greater than one, and Z<X, and tying the first segment of the suture to the next consecutive ring in the first direction if Z=0, or the next consecutive rings in the second direction if Z>0, threading a second segment of the suture in the first direction a second X consecutive rings, skipping in the first direction Y rings immediately adjacent to the second X consecutive rings, threading in the second direction Z consecutive rings, wherein Z may be zero or greater than one, and Z<X, and tying the second segment of the suture to the next consecutive ring from the second X consecutive rings in the first direction if Z=0, or the next consecutive rings in the second direction if Z>0, threading a third segment of the suture in the first direction a third X consecutive rings, skipping in the first direction Y rings immediately adjacent to the third X consecutive rings, threading in the second direction Z consecutive rings, wherein Z may be zero or greater than one, and Z<X, and tying the third segment of the suture to the next consecutive ring from the third X consecutive rings in the first direction if Z=0, or the next consecutive rings in the second direction if Z>0. In some variations, X=3, Y=1 and Z=0, or wherein X=4, Y=1 and Z=2, or wherein X≥2, or wherein X−Z=2.

BRIEF DESCRIPTION OF THE DRAWINGS

FIG. 1F is a schematic cross-sectional view of FIG. 1B.

FIGS. 13A and 12B depict another embodiment of a replacement valve and stent structure comprising partially rotated eyelets.

FIG. 19A depicts perspective view of a replacement valve that includes a valve assembly coupled to a stent structure with a clip, according to one embodiment of the present disclosure.

FIG. 19B depicts a detailed perspective view of the clip of FIG. 19A coupling the valve assembly to the stent structure.

FIG. 19C depicts a cross-sectional view of the clip and the valve assembly of FIGS. 19A and 19B.

FIG. 20A depicts perspective view of a replacement valve that includes a valve assembly coupled to a stent structure with a clip, according to one embodiment of the present disclosure.

FIG. 20B depicts a cross-sectional view of the clip and the valve assembly of FIG. 20A.

FIG. 21A depicts perspective view of a replacement valve that includes a valve assembly coupled to a stent structure with a clip, according to one embodiment of the present disclosure.

FIG. 21B depicts a cross-sectional view of the clip and the valve assembly of FIG. 21A.

DETAILED DESCRIPTION

Figure 1A:
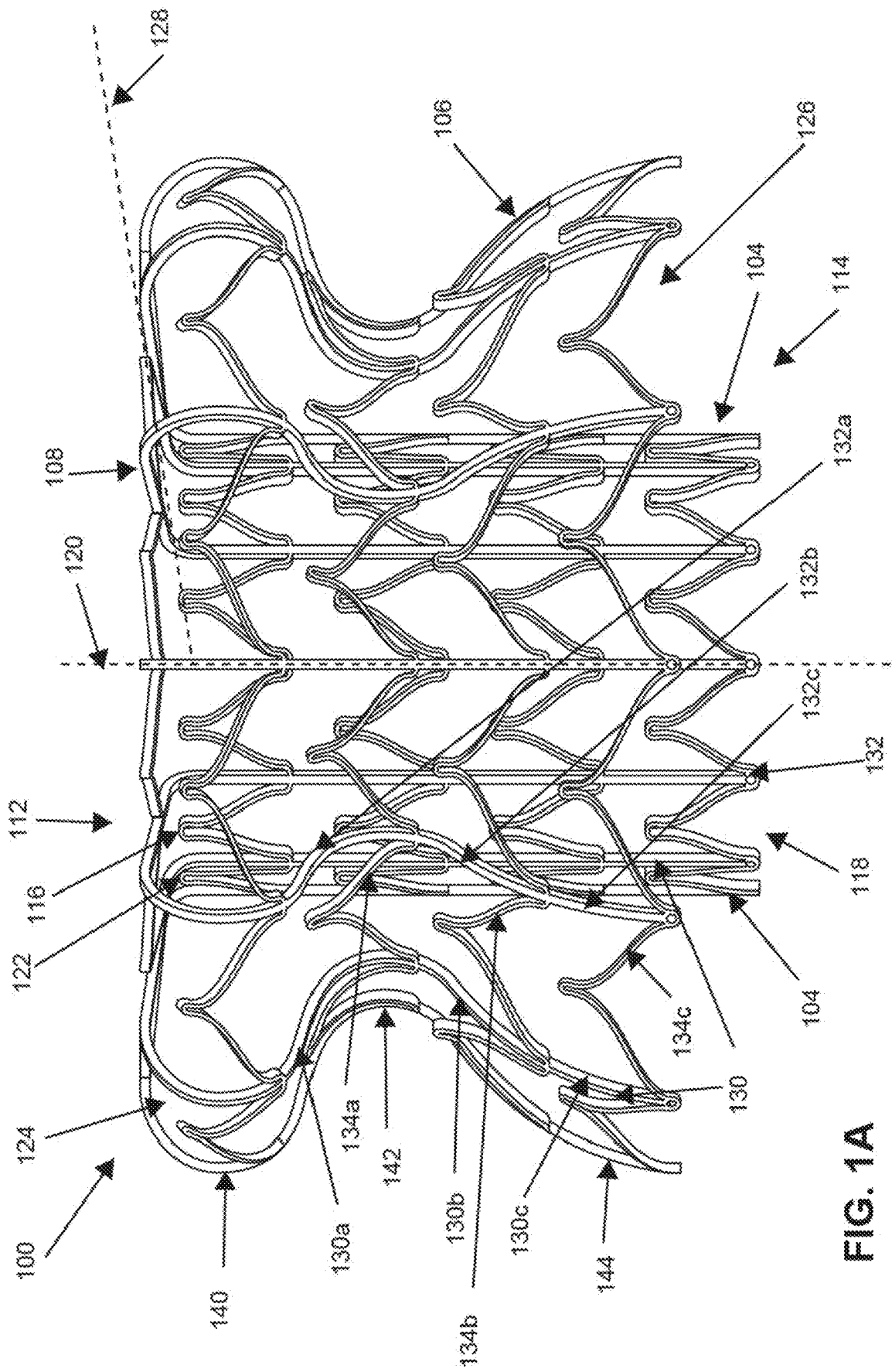
FIGS. 1A and 1B are schematic side elevation and top plan views of one embodiment of a heart valve stent.
Figure 1B:
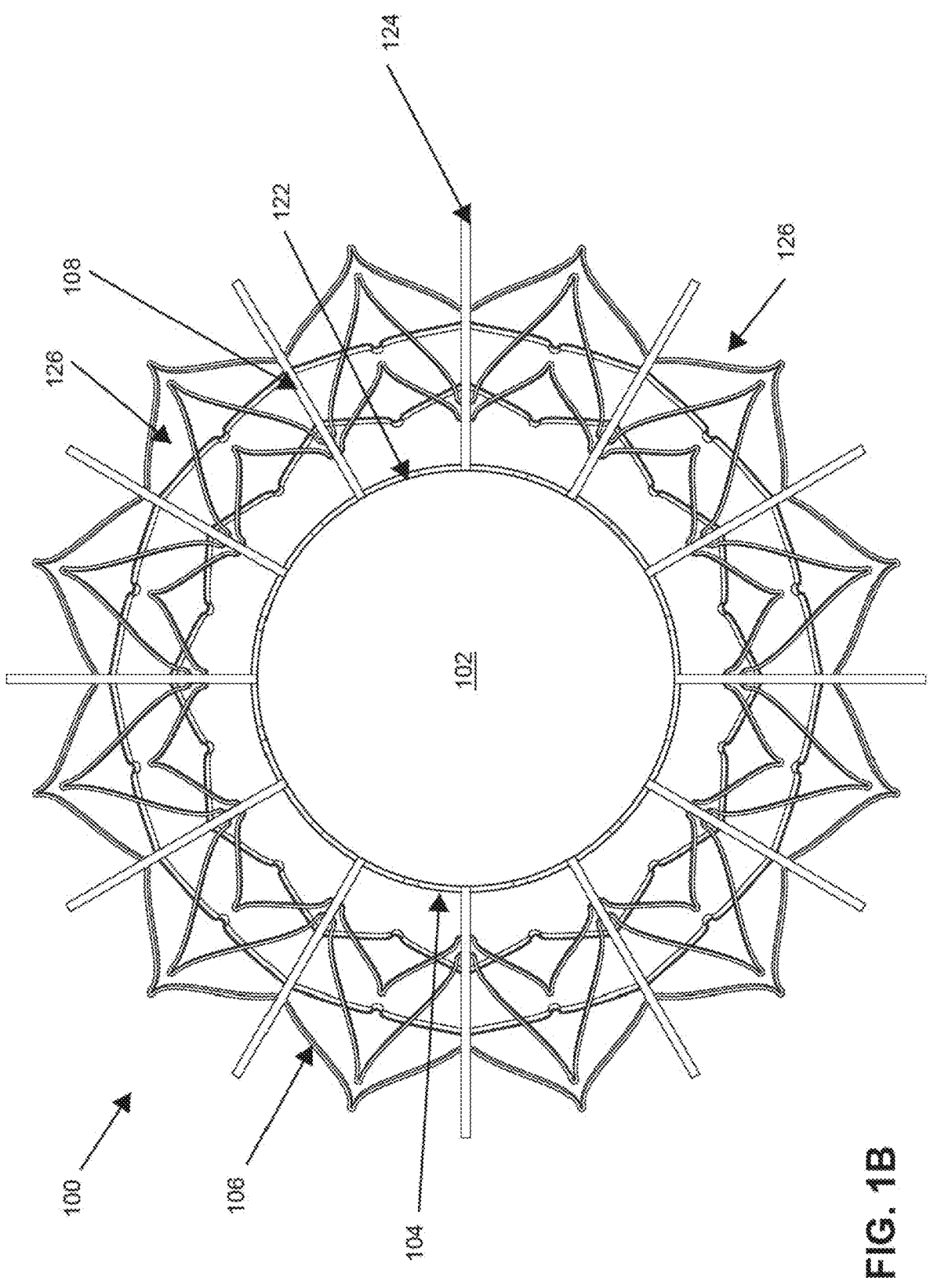

The embodiments herein are directed to a double-wall, folded stent structure with an inner wall providing a tubular lumen that is attached to a leaflet valve assembly. The inner wall is spaced apart from a tubular outer wall that is configured to seal and/or anchor to the surround native valve anatomy, but is contiguous with the inner wall via a transition wall. The transition wall may result from the folding, inversion or eversion of a single tubular structure into a double-wall unibody tubular stent frame or structure. The stent is configured to reversibly collapse into a reduced diameter or reduced cross-sectional shape for loading into a catheter and for delivery to a target anatomical site, and then to re-expand at the implantation site.

In further embodiments, the folded stent structure may be shaped with a middle region having a reduced cross-sectional size in the outer wall, which may facilitate anchoring of the structure across the desired anatomical site. The middle region with the reduced diameter or dimension is configured to expand against the native valve leaflets and/or anatomical orifice, while the enlarged diameter or dimensions of the end regions provide mechanical interference or resistance to displacement. The transition wall of the stent structure may be configured to facilitate inflow of fluid into the inner lumen and through the replacement valve leaflets, while reducing turbulence and/or hemodynamic forces that may displace or dislodge the valve. For example, the transition wall may be angled or tapered radially inward from the outer wall to the inner wall, to improve flow or decreased peak forces acting on the transition wall, compared to a transition wall that is orthogonally oriented between the outer wall and inner wall, or to the longitudinal axis of the stent structure.

Although some of the exemplary embodiments described herein are directed to transcatheter replacement of mitral valves, the components and structures herein are not limited to any specific valve or delivery method, and may be adapted to implantation at the tricuspid, pulmonary, aortic valve locations, and also in non-cardiac locations, e.g., the aorta, venous system or cerebrospinal fluid system, or a native or artificial conduit, duct or shunt. As used herein, the spatial references to a first or upper end of a component may also be characterized by the anatomical space the component occupies and/or the relative direction of fluid flow. For example, the first or upper end of folded stent structure of a replacement mitral valve may also be referenced as the atrial end or upstream end of the valve, while the opposite end may be referenced as the ventricular end or downstream end of the valve.

An exemplary embodiment of a stent structure 100 are depicted in FIGS. 1A-1G, in their expanded configuration. The stent structure 100 comprises an inner lumen 102 formed by an inner all 104. An outer wall 106 is spaced radially apart from the inner wall 104 via a transition wall 108, and forms an annular cavity 110. The stent structure 100 has first closed end 112 that is located at the transition wall 108, and a second open end 114 of the outer wall 106, wherein the annular cavity 110 is open and accessible.

The inner lumen 102 comprises a first opening 116 surrounded by the transition wall 108 and a second opening 118 at the second open end 114 of the stent structure 100. The longitudinal axis 120 of the inner lumen 102 is typically coincident with the central axis of the stent structure 100, but in some variations, the inner lumen may be eccentrically located relative to the outer wall of the stent structure. The inner lumen 102 typically comprises a circular cross-sectional shape with a generally cylindrical shape between the first opening 116 and second opening 118, as depicted in FIGS. 1A to 1D. In other examples, the inner lumen may comprise a frustoconical, oval or polygonal shape. In some variations, the stent structure may comprises an inner lumen where the size and/or shape of the first and second openings may be different. The lengths of the inner lumen 102 may be in the range of 10 mm to 50 mm, 15 mm to 40 mm, or 20 mm to 25 mm, and the diameter or maximum cross-sectional dimension of the inner lumen along its longitudinal length may be in the range of 15 mm to 40 mm, 20 mm to 30 mm, or 25 mm to 30 mm. In embodiments where the inner lumen comprises a non-cylindrical shape, the difference between the diameter or cross-sectional dimension of the first opening 116 and the second opening 118 may be in the range of 1 mm to 10 mm, 1 mm to 5 mm, or 1 mm to 3 mm.

The location of the first and second openings 116, 118 of the inner lumen 102 relative to the overall stent structure 100 may also vary. In some variations, the first opening 116 of the inner lumen 102 may be recessed relative to the first end 112, as depicted in FIGS. 1A to 1G. In other examples, the first opening may be generally flush with the first end transition wall of the stent structure. The location of the first opening 116 may also be characterized as recessed, flush or protruding relative to the longitudinal location of the inner junction 122 between the inner wall 104 or lumen 102 and transition wall 108, or relative to the outer junction 124 between the transition wall 108 and the outer wall 106, as depicted in FIG. 1G. Likewise, the second opening 118 of the inner lumen 102 may also be characterized as recessed, flush or protruding, relative to the longitudinal location of outer opening 126 of the outer wall 106. For example, with stent structure 100, the second opening 118 of the inner lumen 102 comprises an offset or protruding location relative to the outer opening 126 of the outer wall 106. In some variations, the inner lumen may protrude relative to the second opening of the outer wall in variations where a smaller or shorter outer wall is preferred to accommodate smaller size native valve anatomy. The inner lumen size, however, may remain relatively the same size between different size variations, to provide consistent valve geometry and/or hemodynamic characteristics.

The transition wall 108 of the stent structures 100 has a generally annular and slightly tapered shape surrounding the inner lumen 102 in the expanded configuration, but in other variations may have a different shape and/or surface angle. Referring to FIG. 1G, for example, the transition walls 108 on cross section may comprise a generally linear shape between the inner junction 122 and the outer junction 124, but in other variations, may comprise a curved shape, e.g., concave or convex shape. In other variations, the transition wall may have a generally orthogonal angle relative to the longitudinal axis of the inner lumen. Referring back to FIG. 1G, the transition walls 108 of stent structure 100 may form an external acute angle 128 relative to the longitudinal axes 120 of the inner lumen 102. The angle 128 may be in the range of +45 to +89 degrees, +75 to +89 degrees, or +81 to +85 degrees, with optional variances in the range of ±1 degree, ±2 degrees, ±3 degrees or ±4 degrees. In other variations, the transition wall angles may be in the range of −45 to +45 degrees, −75 to +75 degrees, or −85 to +85 degrees.

As noted previously, in some embodiments, the outer wall 106 of the stent structure 100 comprises a non-cylindrical shape when in the expanded configuration. The outer wall 106 may comprise a first end region 140 that is contiguous with the transition wall 108, comprising an external convex shape, a second end region 142 that forms the outer opening 126, As shown, the inner junction 122 between the upper region of inner wall 104 and the transition wall 108 may comprise a first or upper inner radius of curvature $R_1$ along the inner curvature of the bend, and a first or upper inner bend angle $A_1$. The bend angle is the angle defined by the arc length of the bend from the center of the radius of curvature, between points where the bend transitions to a linear segment or a different bend. The outer junction 124 between the transition wall 308 and the upper region of the outer wall 106 may comprise a second or upper outer radius of curvature $R_2$ and a second or upper outer bend angle $A_2$. The middle region of the outer wall 108 comprises a third or middle radius of curvature $R_3$ and a third or middle bend angle $A_3$, and the lower region of the outer wall 108 may comprise a fourth or lower radius of curvature $R_4$ and fourth or lower bend angle $A_4$.

As shown in FIG. 1G, the centerpoints of the first and second radii of curvatures $R_1$, $R_2$ lie may lie within the annular cavity 110 of the stent structure 100, while the third radii of curvature $R_3$ may be external to the outer wall 108, and the fourth radii of curvature $R_4$ may be in the ipsilateral annular cavity 110, the inner lumen 102, the contralateral annular cavity 110*b*, depending on the size.

The radii of curvature and the bend angles of the stent structure may be used to define the geometry of the stent in the expanded configuration, but also affect the geometry of the stent in its delivery or collapsed configuration. Regions or segments of the stent may be configured with a smaller radius of curvature and/or larger bend angle to facilitate the folding of the stent at that region or segment as the stent is collapsed for the delivery or collapsed configuration. A larger radius of curvature or a smaller bend angle may be provided to facilitate straightening of that region or segment for the delivery or collapsed configuration. For example, with stent structure 100, a relatively smaller radius of curvature $R_1$ facilitates the folding or collapse of the stent structure at the inner junction 122, while a larger radius of curvature $R_2$ facilitates the flattening of the first end region 140 during delivery or loading of the device into the delivery system. Thus, in the collapsed configuration, the transition wall 108 is further bent at the inner junction 122 and collapsed around the inner wall 104. The outer wall 106 is also collapsed around the inner wall 104, but not collapsed around the transition wall 108 Similarly, the middle region 142 and second end region 144 of the outer wall 106 may also be provided with a larger radius of curvature $R_3$ and $R_4$, which will result in flattening of the concave shape in the middle region 142 and convex shape of the second end region 144 to also facilitate collapse of the outer wall 106. Thus, for the stent structure 100 in its collapsed configuration, the inner wall 104 will be radially inward to the outer wall 106 and to the transition wall 108. The outer wall 106 and transition wall 108 will be in contact with a sheath, capsule or outer wall of a delivery system, while the inner wall 104 may be in contact with an inner core or inner catheter wall. In other embodiments, the stent structure may be provided with a relative larger radius of curvature $R_1$ and smaller radius of curvature $R_2$, such that in the collapsed configuration, the transition wall will collapse proximally against the delivery device and not the inner wall 104, and where the outer wall 106 is collapsed against both the inner wall 104 and the transition wall 108.

In some variations, the stent geometry may be characterized by one or more relative characteristics of the stent in its expanded configuration. For example, the stent structure 100 may be characterized as $A_3>A_1$ and $A_3>A_2$ and $A_3>A_4$ and/or $R_1<R_2<R_3<R_4$, $R_1<R_2\approx R_3\leq R_4$ $R_1<R_2\approx R_3\approx R_4$, or $R_1<R_2\leq R_3\leq R_4$.

Other stent variations may include:
1) $R_2<R_1<R_3<R_4$;
2) $R_2<R_1\approx R_3<R_4$;
3) $R_2<R_1\approx R_3\approx R_4$;
4) $R_4>R_1\approx R_2$;
5) $R_4>R_1\approx R_2>R_3$;
6) $A_2$:$A_1$ ratio in the range of 1 to 3, 1.5 to 2.5 or 1.8 to 2.2;
7) $A_3$:$A_4$ ratio in the range of 1 to 4, 1.5 to 3.0 or 2.2 to 2.4;
8) $A_2$:$A_4$ ratio in the range of 2 to 4, 2.5 to 3.5 or 2.8 to 3.2;

The stent structures herein further comprise a plurality of integrally formed stent struts segments, as depicted in FIGS. 1A to 1G. Some struts may be characterized as longitudinal strut segments 130a, 130b, 130c which generally reside within a radial plane in which the longitudinal axis of the stent structure also resides, or lateral strut segments 134a, 134b, 134c, which are integrally formed with longitudinal struts 130a, 130b, 130c, 132a, 132b, 132c, where the two longitudinal struts 130, 132 are lying in different adjacent radially oriented planes, respectively. In embodiments with an even number of equally spaced apart longitudinal struts, as depicted in FIG. 1G, each radial plane 150 will include the longitudinal axis 120 of the stent structure 100, and two longitudinal struts 130, 136 located on opposite sides of the stent structure 100. The longitudinal and lateral strut segments may also be further grouped, with a group of longitudinal strut segments lying in the same radial plane to form a contiguous length of longitudinal strut 130, 132 in the inner wall 104 transition wall 108 and/or outer wall 106.

Figure 1C:
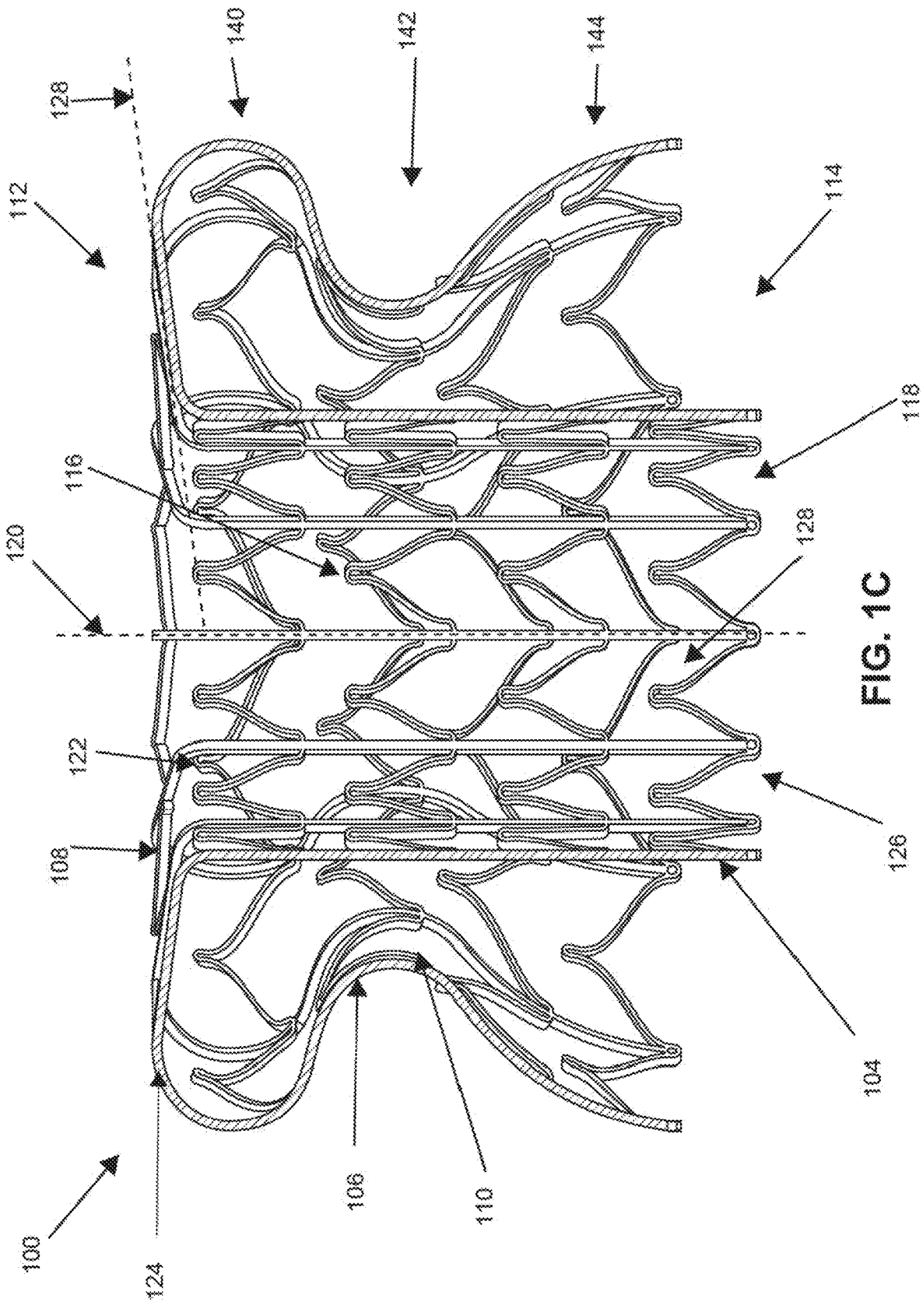
FIG. 1C is a partial cross-sectional view of the heart valve stent of FIG. 1A with a portion of the outer wall omitted.
Figure 1D:
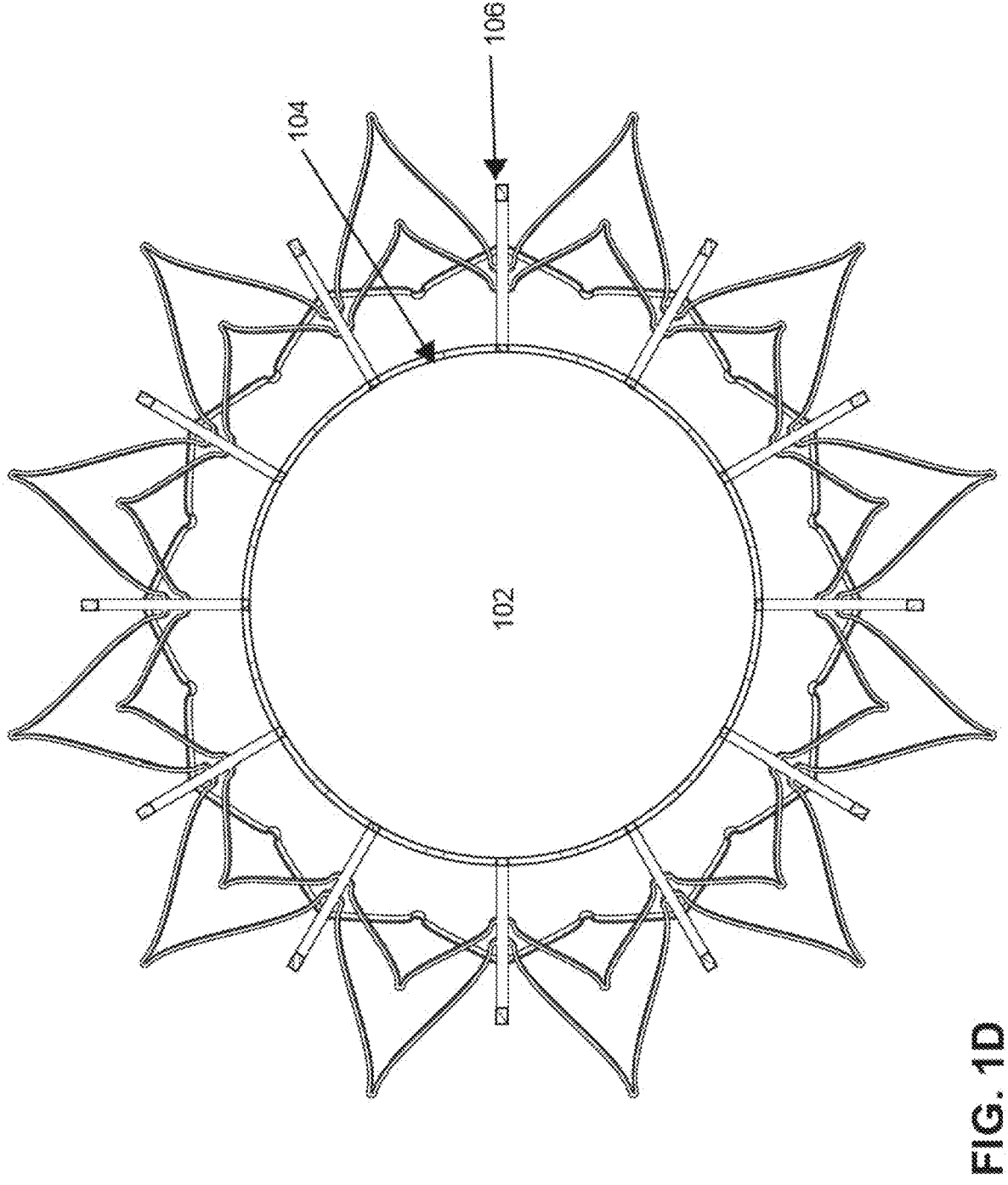
FIG. 1D is a schematic cross-sectional view of FIG. 1B.
Figure 1E:
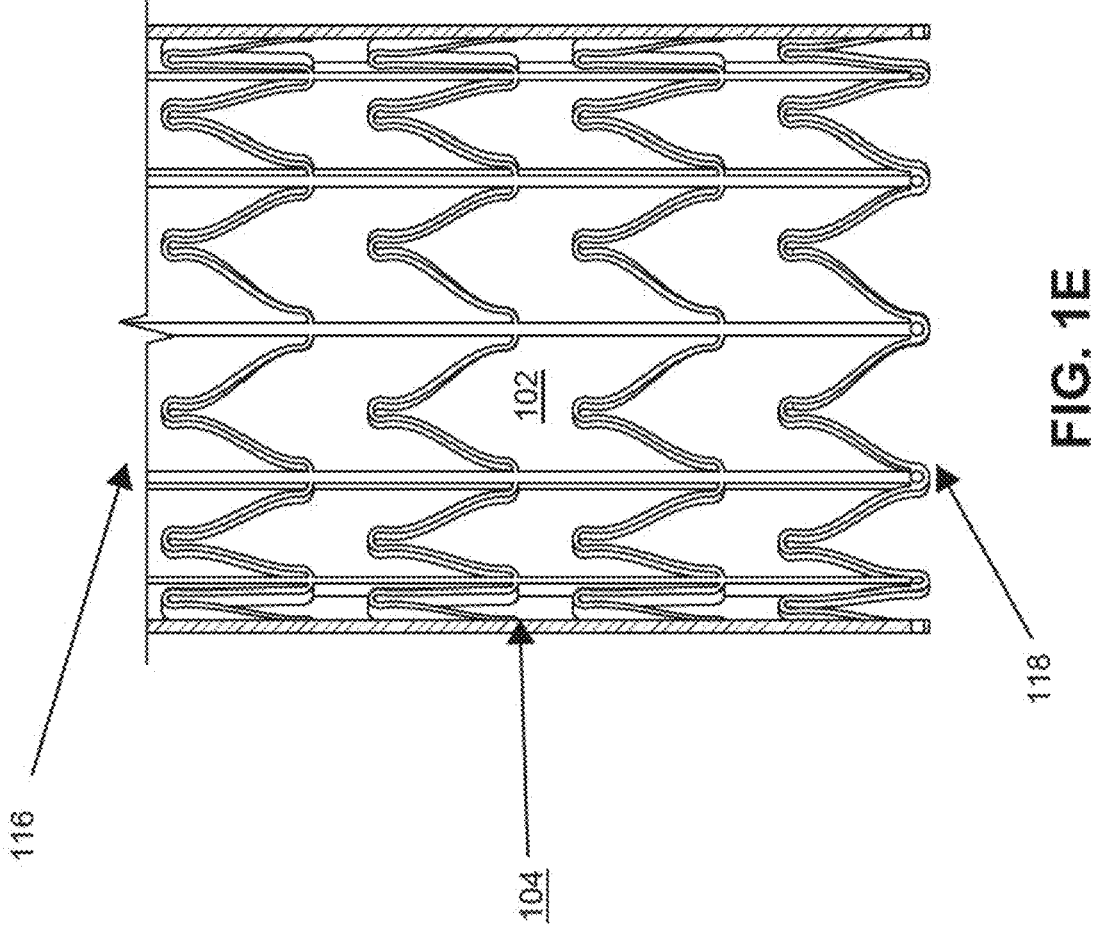
FIG. 1E is a schematic cross-sectional view of the inner wall of the heart valve stent, without the outer wall.
Figure 1F:
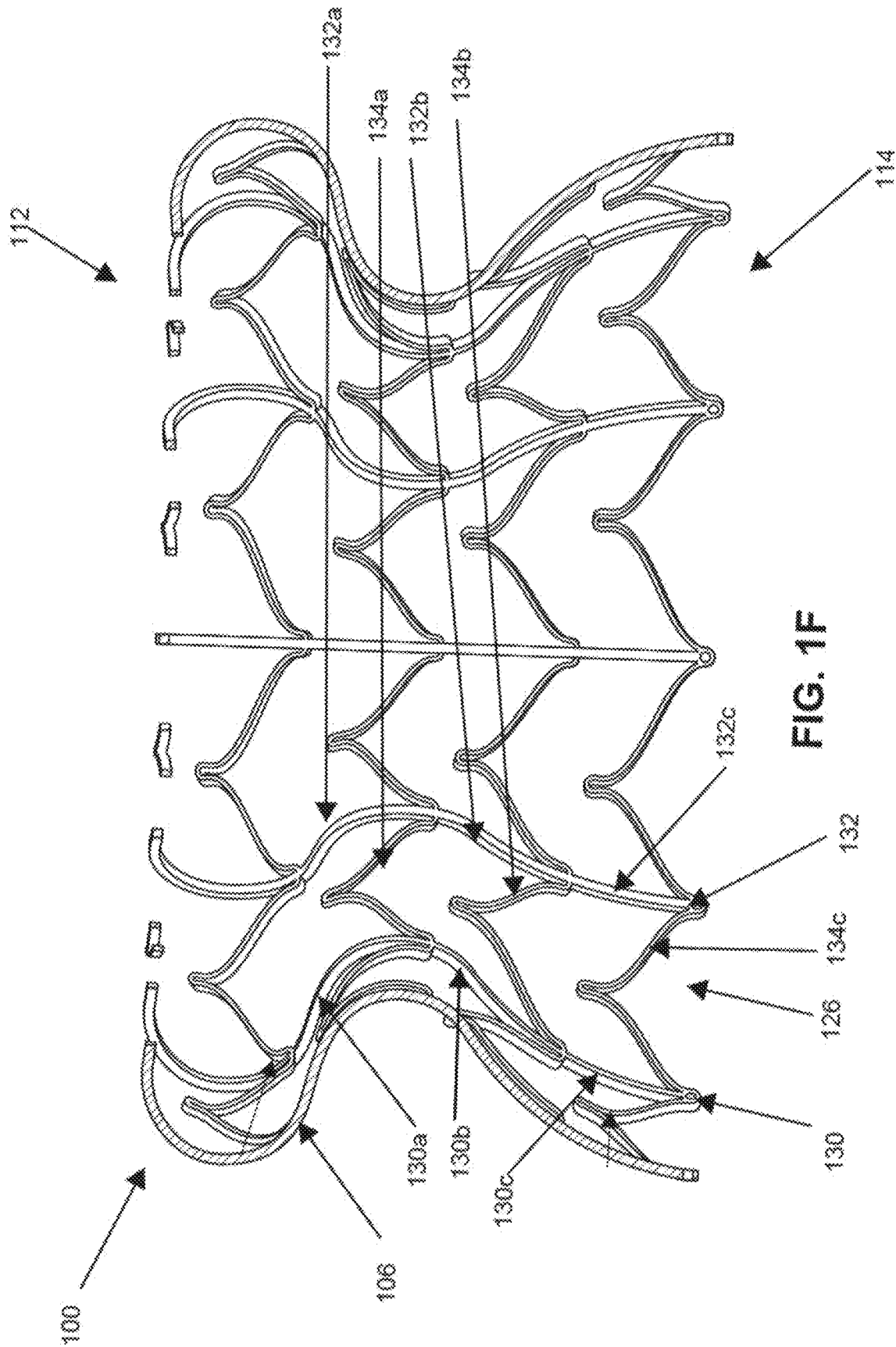
FIG. 1F is a schematic cross-sectional view of the outer wall of the heart valve stent, without the inner wall.
Figure 1G:
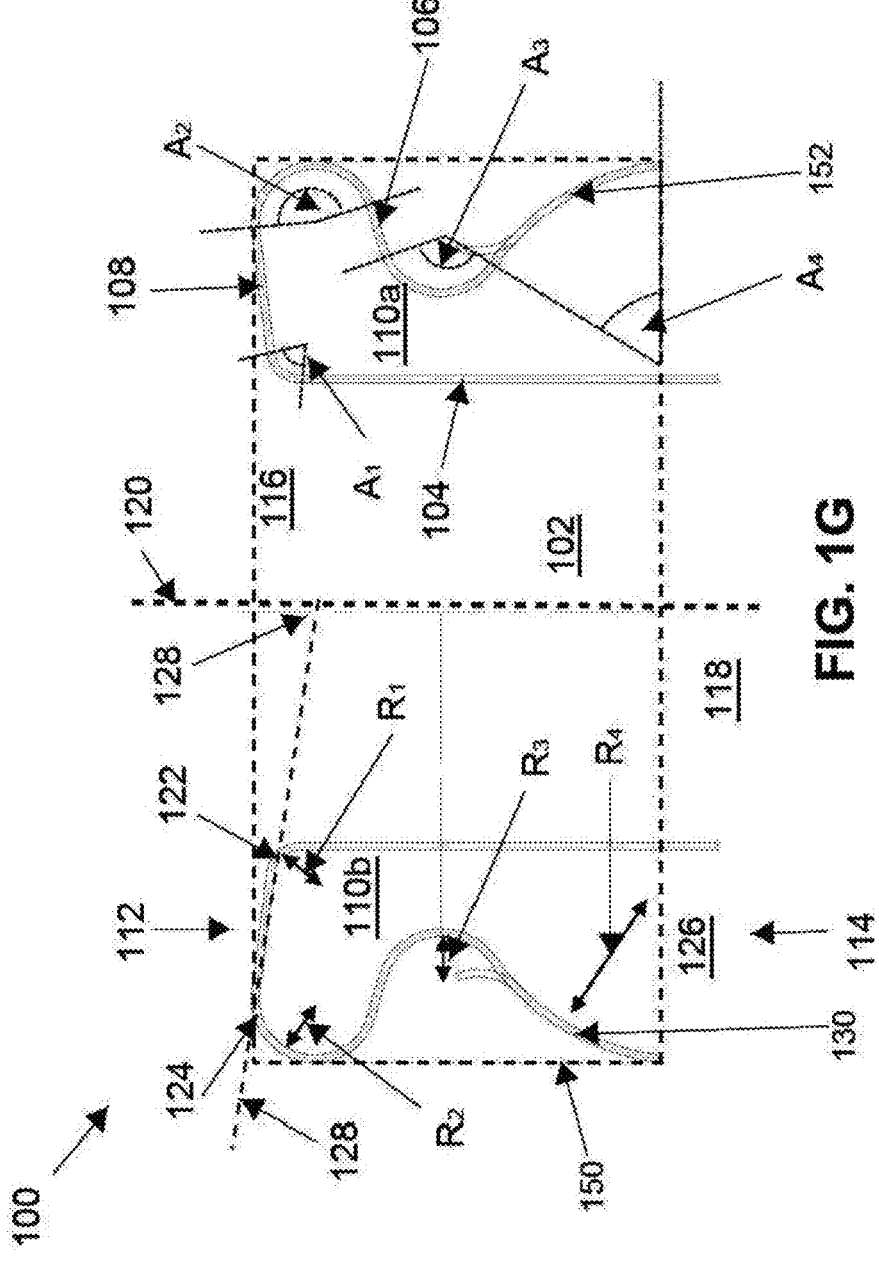
FIG. 1G is a schematic component view of two longitudinal struts from FIG. 1A.
Figure 1H:
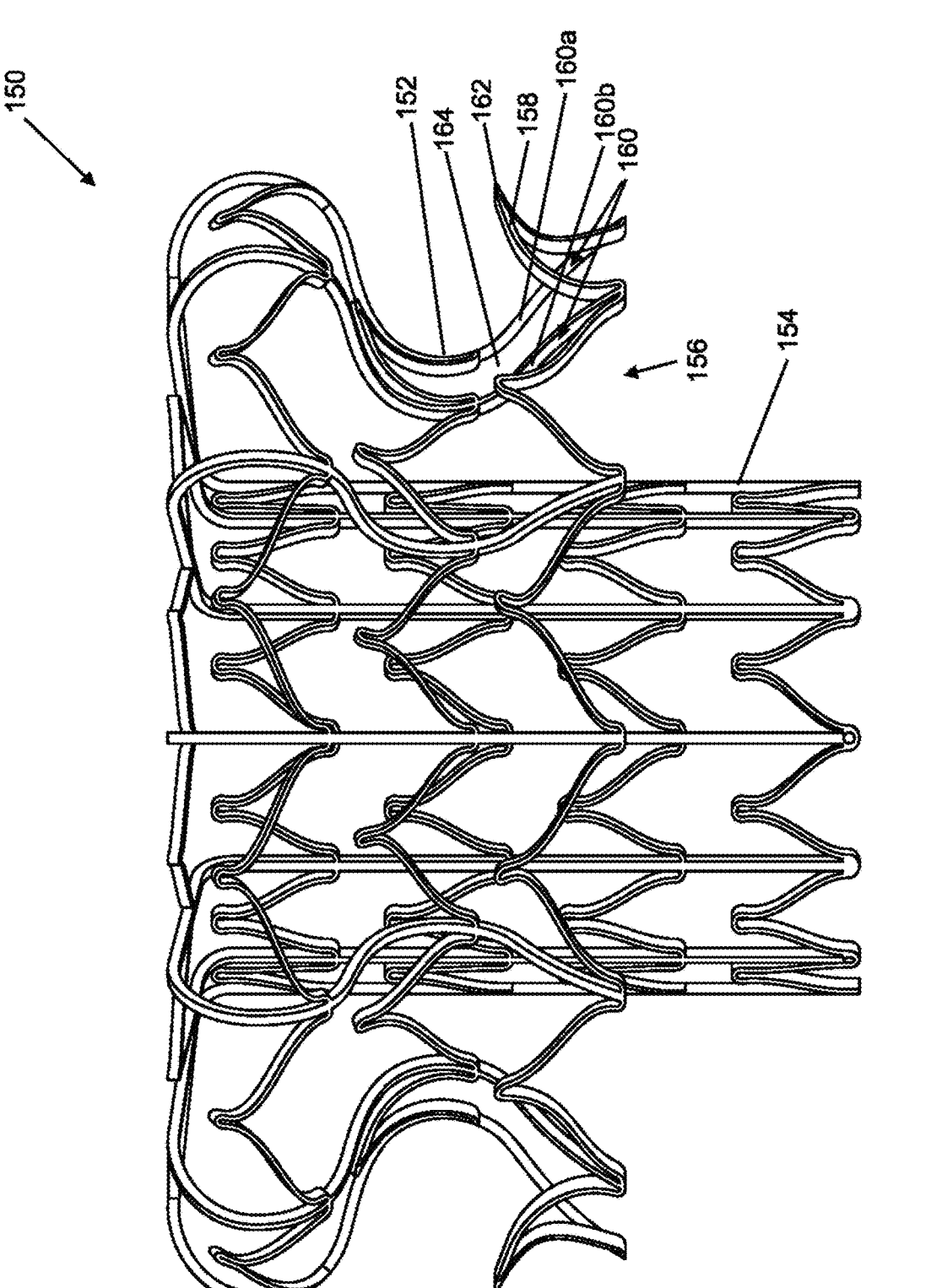
FIG. 1H is a schematic side elevation view of a variant of the heart valve stent with a shorter outer wall.

FIG. 1H depicts another embodiment of a stent structure 150, similar to stent structure 100, except that its outer wall 152 is shorter in longitudinal length, and thus even more of the inner wall 154 extends from the open end 156 of the outer wall 152, relative to and wherein the lateral struts 158 located at the open end 156 of the outer wall 152 are bent radially outward relative to the adjacent longitudinal struts

160. In some variations, the radial distance from which the center 162 of the lateral strut 158 to a location 164 corresponding to where the center 162 of the lateral strut 158 would be if not displaced radially outward, e.g., midway between the two closest locations of the two closest longitudinal struts 160a, 160b, is in the range of 2 to 10 mm, or 3 to 8 mm or 3 to 5 mm. This feature of the increased radially outward position of the lateral struts may also be provided in any of the other stent structure embodiments described herein.

In some examples, a longitudinal strut, comprising a plurality of contiguous longitudinal strut segments, provided in one wall may terminate or be interrupted at the junction of the next wall, but in some embodiments, may span the two or three walls. In some further embodiments, a longitudinal strut may be provided along the entire folded length of a stent structure, between the opening of the inner lumen, along the length of the inner wall and through the transition and outer wall to the end of the outer wall, while still having each of the contiguous strut segments residing in the same radial plane 150, as depicted for longitudinal struts 130, 152 in FIG. 1G. It is hypothesized that such an arrangement of the multiple contiguous longitudinal struts throughout the folded stent structure provides a structural integrity to the stent structure that better redistributes forces acting on the stent structure, with less force concentration found in stent structures that comprises multiple components that are welded or attached together, whether at the point of manufacture or at the point of use. In still other examples, the contiguous length of longitudinal struts may span all three walls but the stent may comprise a different strut configuration at one or both of the inner and outer ends of the folded stent structure, e.g., different orientation of circumferential struts or tissue anchors.

In exemplary stent structure 100, the longitudinal strut segments along the inner lumen of the stent structure 100 comprise a linear configuration, so the longitudinal strut segments are generally parallel in both their expanded and contracted configurations. Because of this arrangement, the inner lumen 102 do not exhibit any foreshortening when changing from the contracted to the expanded configuration. This may reduce or eliminate any axial stretching of the valve structure attached to the inner lumen. This may also permits the inner lumen to be predictably positioned and deployed while reducing the risk of inadvert position shifting.

While the non-cylindrical configuration of the outer wall 106 may exhibit some foreshortening as the outer wall 106 transitions from a relatively straight orientation in the contracted configuration to the hourglass shape or convex/concave/convex contour in its expanded configuration, the foreshortening effect may not be uniform or symmetrical, and thus may alter the relative position of some features of the outer wall 106. This may be mitigated by adjusting the angular orientation of the transition wall 108, which can then displace the outer wall 106 toward or away from the inlet opening 116 of the stent structure 100 and offset some of the longitudinal displacement of the outer wall 106 that results from the foreshortening. This allows, for example, the reduced diameter middle section of the outer wall 106 to generally maintain the same relative longitudinal location with respect to the overall length of the stent, or to the valve location with the stent, before and after expansion. This in turn may help to maintain the expected implant location during delivery. In some variations, the longitudinal shift upon expansion of the stent structure in the reduced diameter middle section of the outer wall may be less than 5 mm, 4 mm, 3 mm, 2 mm, or 1 mm.

The lateral strut segments may also be characterized by a contiguous set of lateral strut segments that form a partial or complete circumferential or perimeter strut around a wall of the stent structure. The lateral strut segments, however, can vary in more than just their circumferential orientation. To facilitate the expansion and contraction of the overall stent structure, one or more of the lateral strut segments, or all of the strut segments, may comprise a pair of angled legs, each lateral end of each angled leg is contiguous or integrally formed with a longitudinal strut segment or strut and where each angled leg is joined together centrally. While the bend configuration of the formed by the two angled legs may comprise a simple bend, in other examples, each leg may extend centrally to form a hairpin bend region.

Figure 4A:
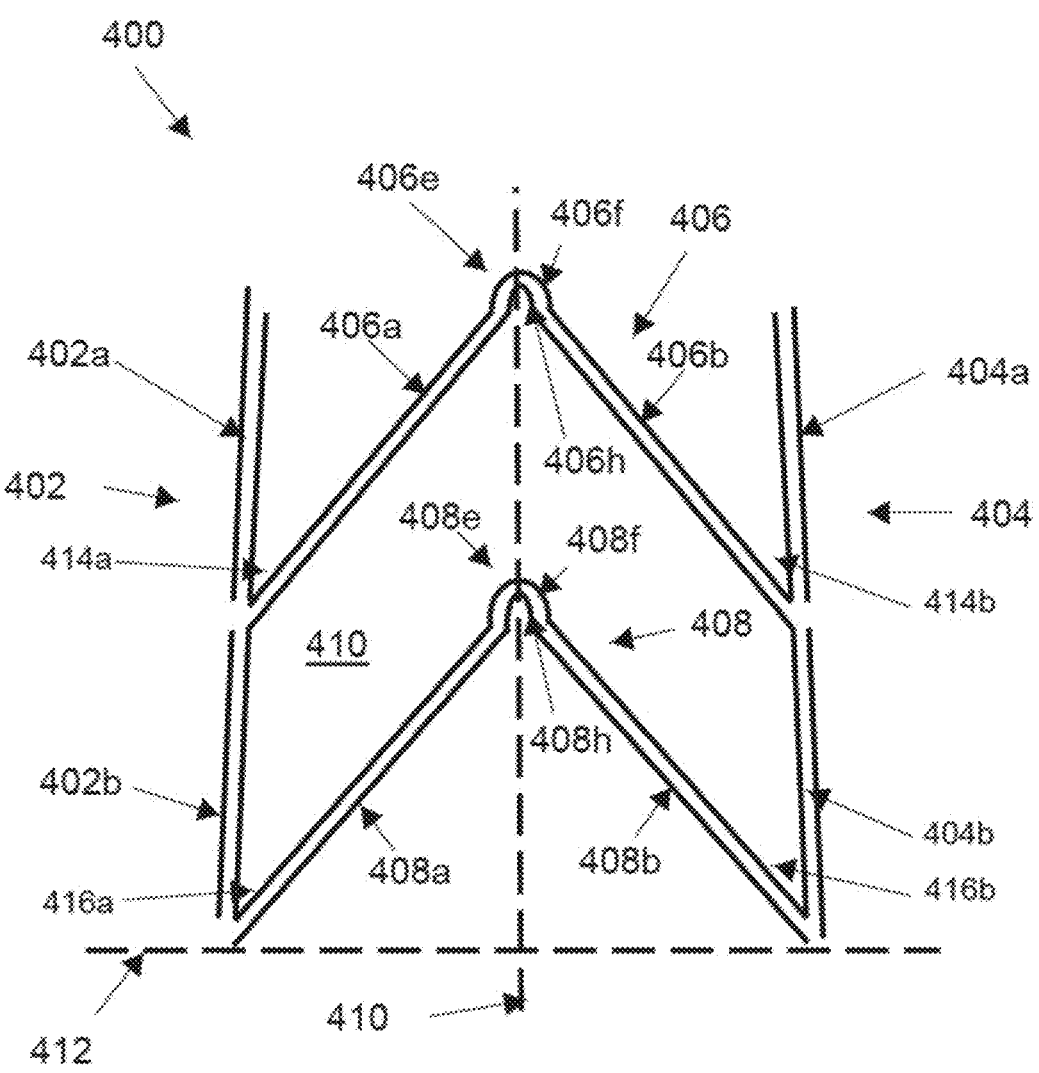
FIGS. 4A to 4C depict various exemplary strut configurations.
Figure 4B:
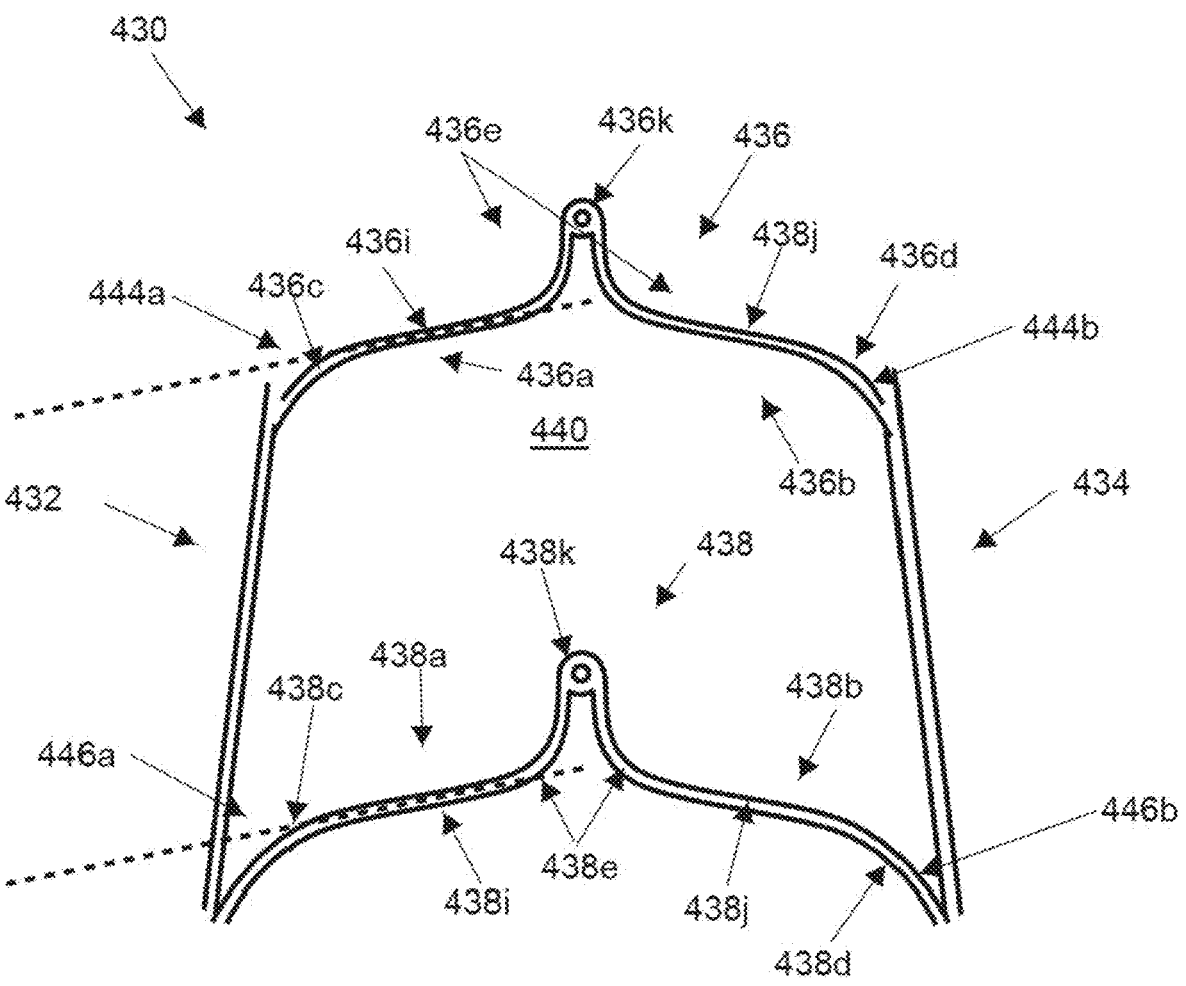
Figure 4C:
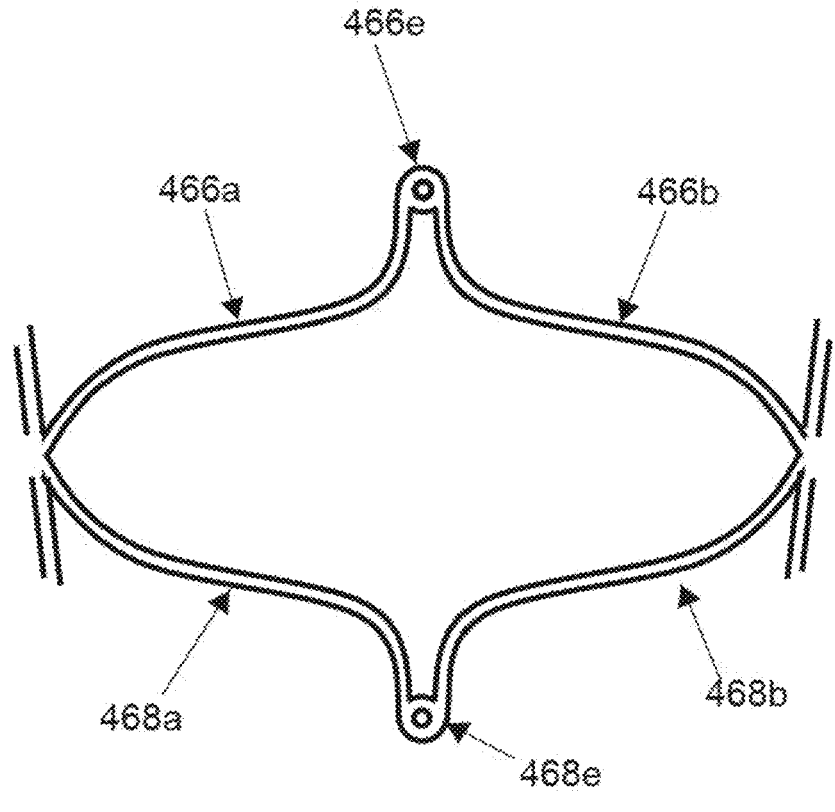

The leg angle formed between each leg and the longitudinal strut may vary in different regions of the stent structure, and may vary depending on the leg length. In FIG. 4A, an exemplary configuration of the lateral strut segment in the inner wall of the stent structure is depicted. Because of the relative lower amount of radial expansion that is exhibited by the inner wall compared to the outer wall, in the expanded configuration the leg lengths of the inner wall are typically shorter than the leg lengths found in the outer wall. Also, due to the limited radial expansion, the legs in the inner wall may have a generally linear configuration, since the structure strain generated at the leg angle is limited. Referring to FIGS. 4B and 4C, in other regions of the stent structure, where a greater amount of radial expansion is experienced, e.g., the outer wall and potentially the transition wall, each leg may comprise a convex curvature along the acute leg angle and a concave curvature along the acute leg angle closer to the middle bend region.

In some embodiments, the lateral strut segments in the inner wall may comprise an acute leg angle that is less than 50 degrees, 45 degrees or 40 degrees, or in the range of 30-50 degrees, 35-45 degrees, or 35-40 degrees, while the acute leg angle in the outer wall may be in the range of 30-75 degrees, 30-60 degrees, 35-55 degrees, or 40-50 degrees. The longitudinal spacing between longitudinally adjacent lateral strut segments in the inner lumen may be smaller than the longitudinal spacing in the outer wall, e.g., 2-8 mm, 3-7 mm, 4-6 mm, 2-6 mm, or 3-5 mm for the inner wall, and 4-10 mm, 5-10 mm, 6-9 mm. This spacing is also the length of the longitudinal strut segments in the various wall regions.

Referring to FIG. 1G, the orientation of the legs and middle bends of one or more set of circumferential strut segments may also deviate radially outward relative to the adjacent longitudinal struts to provide barb-like or force concentration structures to resist displacement of the strut structure relative to the native valve tissue. The lateral struts configured with barbs may be located anywhere along and/or around the outer wall of the stent structure, but in some variations, may be located in the outer wall regions 142 and 144, between the reduced diameter region 142 and the outer opening 126 of the stent structure 100, and oriented toward the reduced diameter region 142. In some further examples, the radially outward displaced circumferential struts may be provided at one or more circumferential struts that are closest to and point toward the region of the outer wall with the smallest diameter. In variations of valves used for mitral valve replacement, the barbs may be formed in the struts to engage the sub-annular tissue on the ventricular side. In some examples, every lateral strut segment in a circumferential strut is radially displaced, but in other examples, 2, 3, 4, 5, 6, 7, 8, 9, 10, 11, 12 or any range between any two of these numbers may radially displaced, or every other or every third or fourth lateral strut segment may be radially displaced. The degree of projection from outer wall shape defined by the plurality of longitudinal struts may be in the range of 2-10 mm, 2-6 mm, or 2-4 mm. In some variations, the barb configuration may be characterized by the ratio of the radial distance between the barb tip and the longitudinal axis of the stent structure, and the radial distance between an adjacent longitudinal strut or outer wall segment (excluding the barb) and the longitudinal axis of the stent structure. This ratio may be in the range of 1.1 to 1.5, 1.05 to 1.30, or 1.10 to 1.20.

Figures 11A, 11B, 11D:
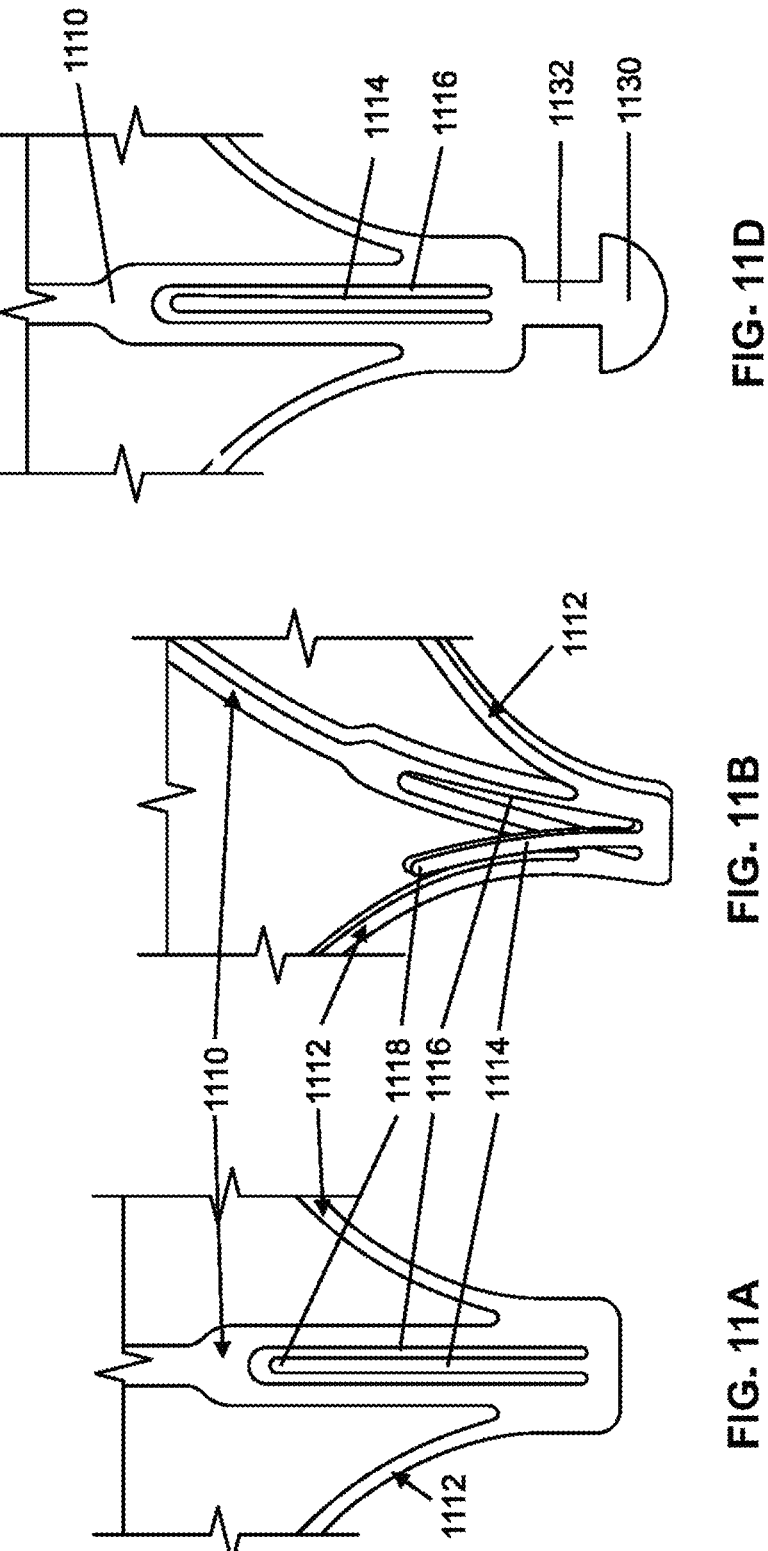
FIGS. 11A and 11B are schematic component view of a stent structure with inset barbs, in the flat and the extended positions, respectively.
FIG. 11D is a schematic component view of a variation with an attachment tab.
Figure 11C:
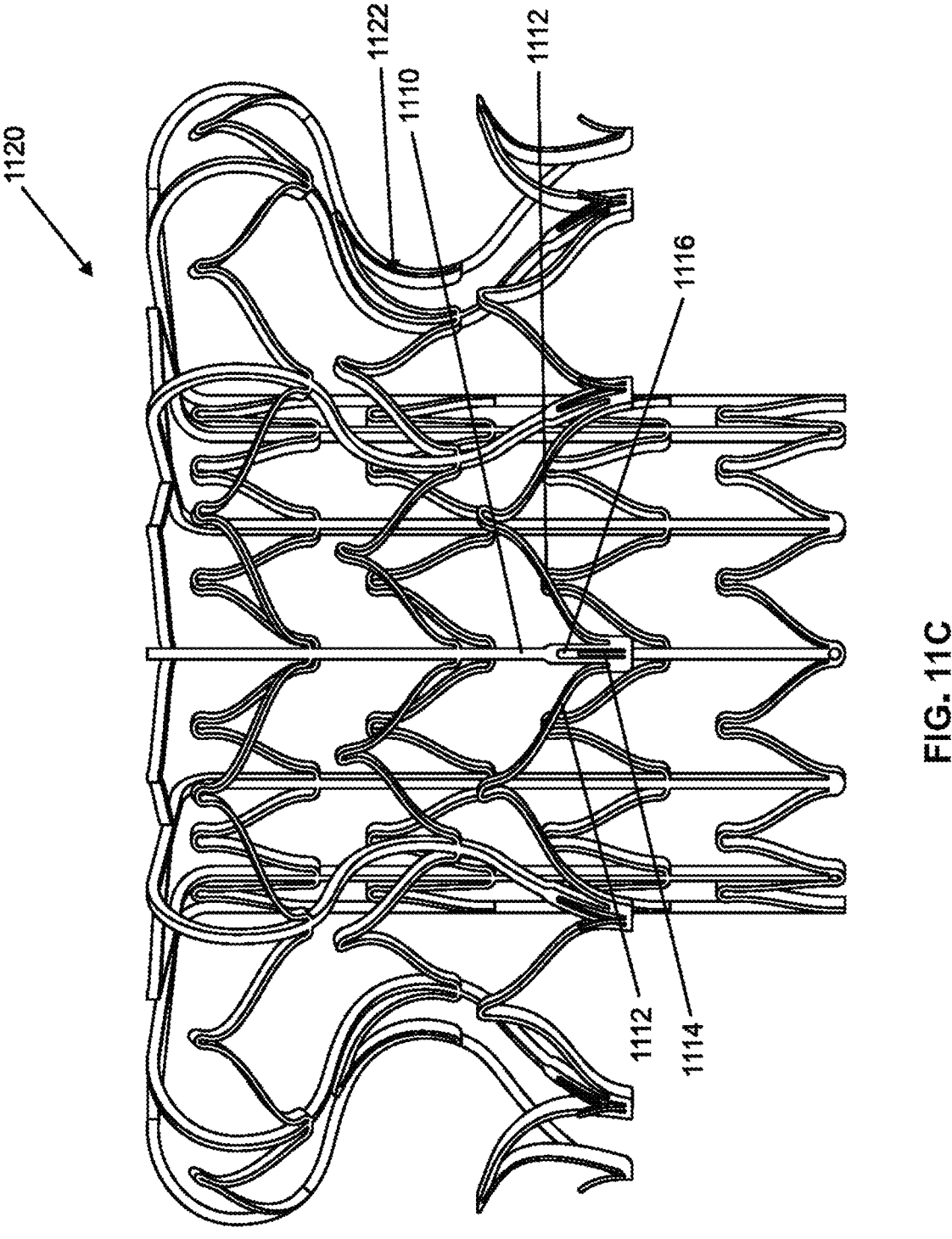
FIG. 11C is a side elevational view of a stent frame with the barbs of FIGS. 11A and 11B.

As depicted in FIG. 1G, the barbs may comprise extensions of the lateral strut, which may be located at the midline of a lateral strut. In other variations, however, barbs may be provided on the longitudinal strut, or other strut of the stent frame. FIGS. 11A and 11B, for example, depict a longitudinal barb 1114 that may be optionally adapted for any of the stent frame embodiments described herein. The barb 1114 is located within an elongate cavity or opening 1116 of the strut 1110. The barb 1114 may have a length in the range of about 1 mm to 10 mm, 2 mm to 8 mm, or 3 mm to 6 mm, and a width of 0.05 mm to 3 mm, 0.1 mm to 1 mm, or 0.1 mm to 0.5 mm. The end 1118 of the barb may be pointed or rounded. The orthogonal distance between the end 1118 of the barb 1114 and the elongate opening 1116 may be in the range of 1 mm to 10 mm, 2 mm to 8 mm, or 3 mm to 6 mm. The elongate cavity may have a length in the range of 3 mm to 15 mm, 4 mm to 12 mm, or 2 mm to 7 mm, and a width in the range of 1 mm to 4 mm, 1 mm to 3 mm, or 0.4 mm to 2 mm. The transverse gap between the side of a barb 1114 and the side of the opening 1116 may be in the range of 0.05 mm to 2 mm, 0.1 mm to 1 mm, or 0.1 mm to 0.5 mm. The distal gap between the end 1118 of the barb 1114 and the opening 1116 may be in the range 0.05 mm to 2 mm, 0.1 mm to 1 mm, or 0.1 mm to 0.5 mm. The width of the strut 1110 may be increased at segments or regions where the inset barb 1114 and opening 1116 are located, relative to the width of the strut where the barb 1114 and opening 1116 are not located. The exemplary embodiments depicted in FIGS. 11A and 11B are located at an end of a longitudinal strut 1110, at a junction between two lateral struts 1112, but in other variations the barb 1114 may be located along the longitudinal strut 1110 at junction spaced away from the end of the longitudinal strut 1110, or at a location spaced away from a junction where the lateral struts 1112 are located. FIG. 111C depicts a stent structure 1120 with the insert barbs 1114 and elongate openings 1116 located at each end of the longitudinal strut 1110 on the outer wall 1122.

In some further examples, control apertures or attachment structures may be provided on a strut segment or at the junction between two or more strut segments. The control aperture may be used to releasably attach tensioning members, including but not limited sutures, wires and hooks, which may be relaxed or tensioned to control the expansion, contraction, release or loading of the stent structure during delivery of the valve prosthesis or loading of the valve prosthesis into its delivery system. Various embodiments of the delivery system and method are described in greater detail below. Referring to example in FIG. 1E, control apertures are optionally provided at the junction of the end of each contiguous longitudinal strut in the outer wall and in the inner wall. In addition, control apertures may be optionally provided in the middle bends of one or both of the two circumferential struts closest to the outer opening 126 of the outer wall 106.

In another variation, depicted in FIG. 11D, an end of a longitudinal strut 1110 includes an attachment head 1130 projecting from the end of the strut 1110 via an attachment neck 1132. This attachment head 1130 and neck 1132 may be provided on one, two, three, four or more, or all of the longitudinal struts of the stent frames, on the inner wall and/or outer wall. The attachment head 1130 and neck 1132 structures may be used to retain or otherwise engage a delivery system, when a rigid attachment is preferred over a tension line attachment, for example. Here, the attachment head 1130 comprises a hemispheric shape, but in other variations, the head may be polygonal, square, rectangular, circular, oval, triangular, star or other shape. In the exemplary embodiment depicted in FIG. 11D, the head and neck structures 1130, 1132 is provided on a strut 1110 that also includes an inset barb 1114 and barb opening 1116, but the two features are not necessary to include together and the head and neck structures 1130, 1132 may be incorporated on any of the stent structures described herein.

Figure 12A:
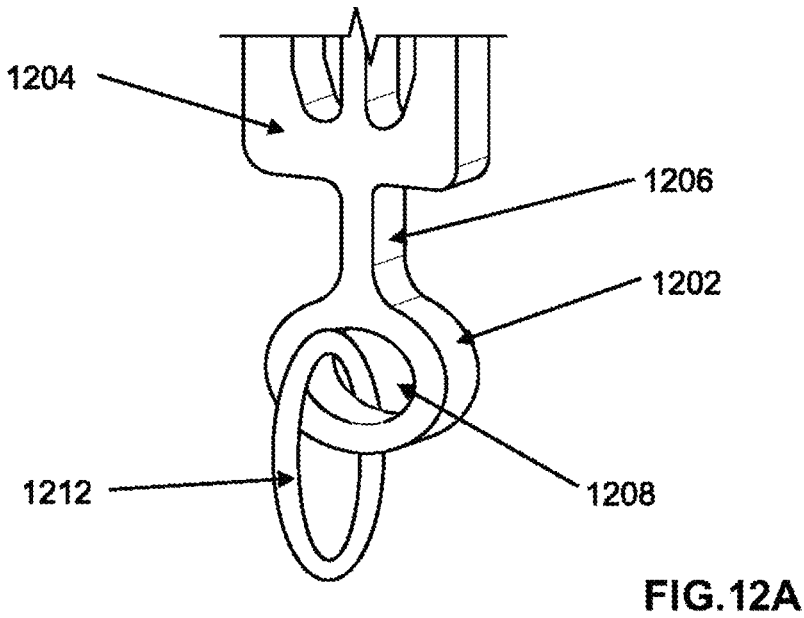
FIGS. 12A and 12B depict another embodiment of a replacement valve and stent structure comprising radially oriented eyelets.
Figure 12B:
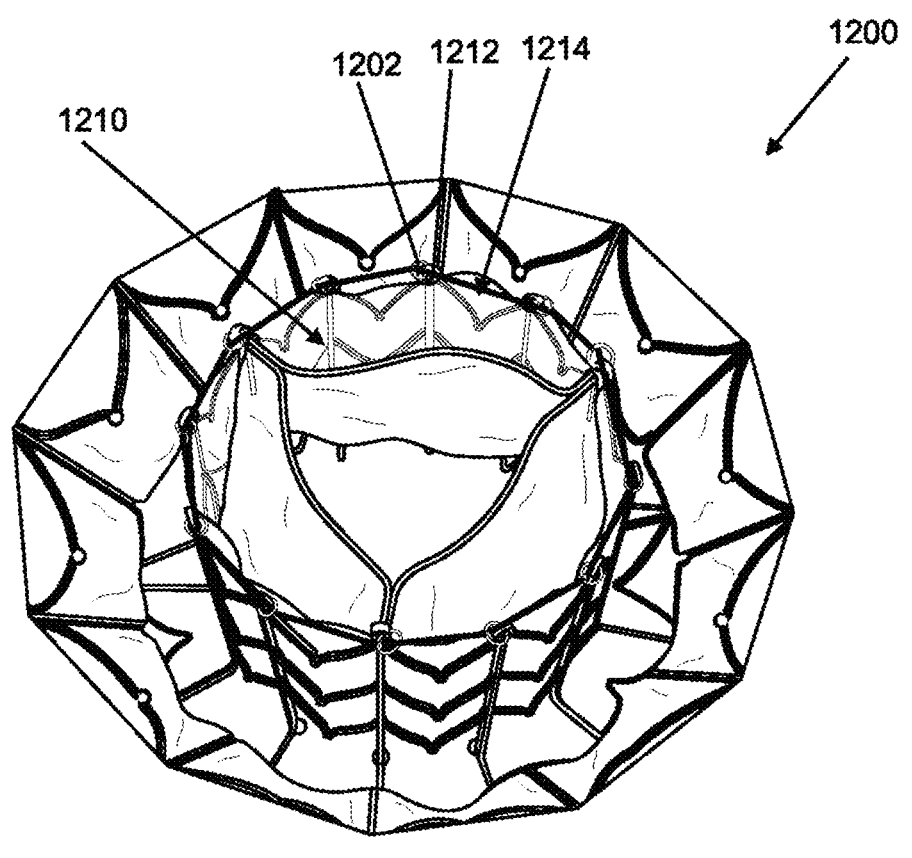

FIGS. 12A and 12B depict another embodiment of a stent structure or replacement valve 1200, comprising an attachment structure with an elliptical or circular eyelet 1202 provided on an end of the longitudinal struts 1204 of the valve 1200 via an eyelet extension or neck 1206, with a circular opening 1208 in the eyelet 1202. In this exemplary embodiment, the eyelets 1202 are provided on the struts 1204 of the inner wall 1210, and a ring 1212 is also attached to each eyelet 1202. The rings 1212 may be used to facilitate the threading of a delivery line or loop 1214, as the orientation of the openings 1208 of the eyelets 1202 in a radial inward/outward pose may increase friction when the delivery line 1214 is tensioned to facilitate collapse and/or loading of the valve 1200.

Figure 13A:
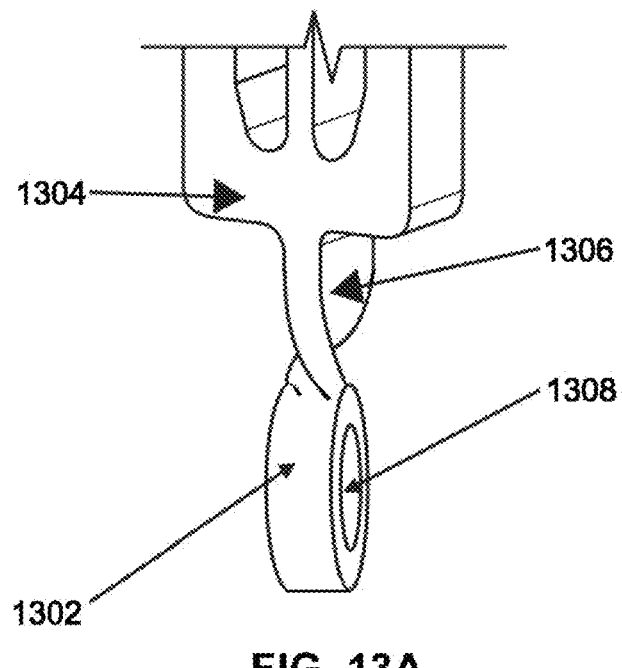
Figure 13B:
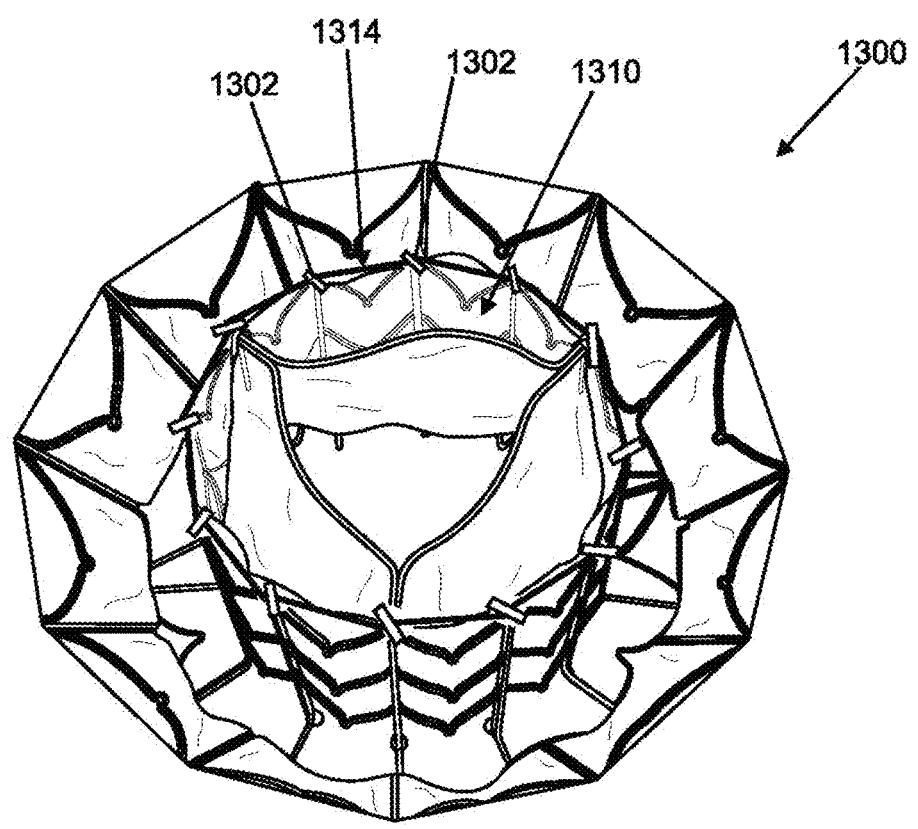

FIGS. 13A and 13B depict still another embodiment of a stent structure or replacement valve 1300, comprising an attachment structure with a circular eyelet 1302 that is also provided on an end of the longitudinal struts 1304 of the inner wall 13010 of valve 1300 via an extension or neck 1306, and a circular opening 1308 in the eyelet 1302. This exemplary embodiment, however, differs from valve 1200 depicted in FIGS. 12A and 12B in that the eyelets 1302 are rotated 30 to 45 degrees. This can be done by twisting the neck 1306 of the eyelet 1302. This rotation reorients the eyelet openings 1308 in so that they are partially facing the toward a circumferential or tangential direction and thus the other adjacent eyelets, thereby decreasing friction between the eyelet 1302 and the delivery line or loop 1314, so that the attachment of a ring to each eyelet 1302 is not required or otherwise provided, as with the valve 1200 in FIGS. 12A and 12B. In other variations, the eyelet necks 1306 may be twisted in a range of about 15 to 90 degrees, or 30-60 degrees, though it is contemplated that larger twist angles may result in weakening of the eyelet neck. An increased number of smaller heating/deformation steps may be used during the manufacturing process to increase the twist angle while minimizing a decrease in structural integrity.

Figure 14A:
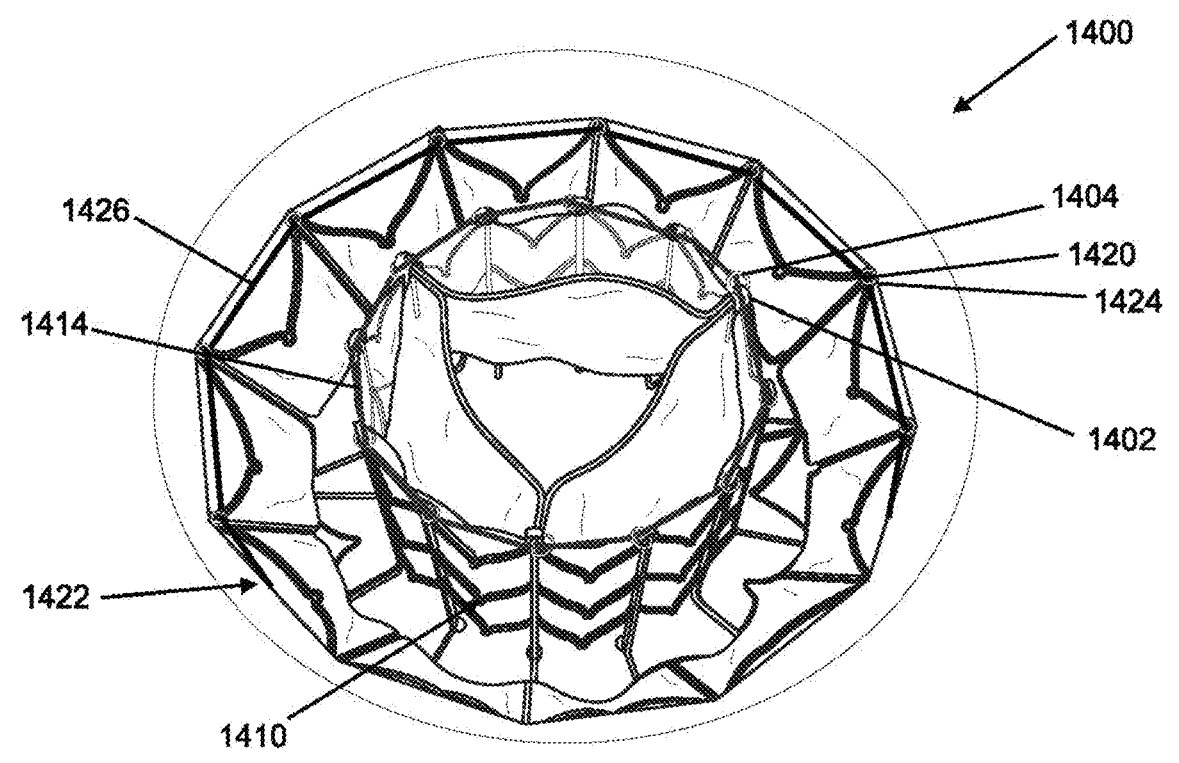
FIGS. 14A and 14B depict embodiments comprising eyelets and rings on the inner and outer walls.
Figure 14B:
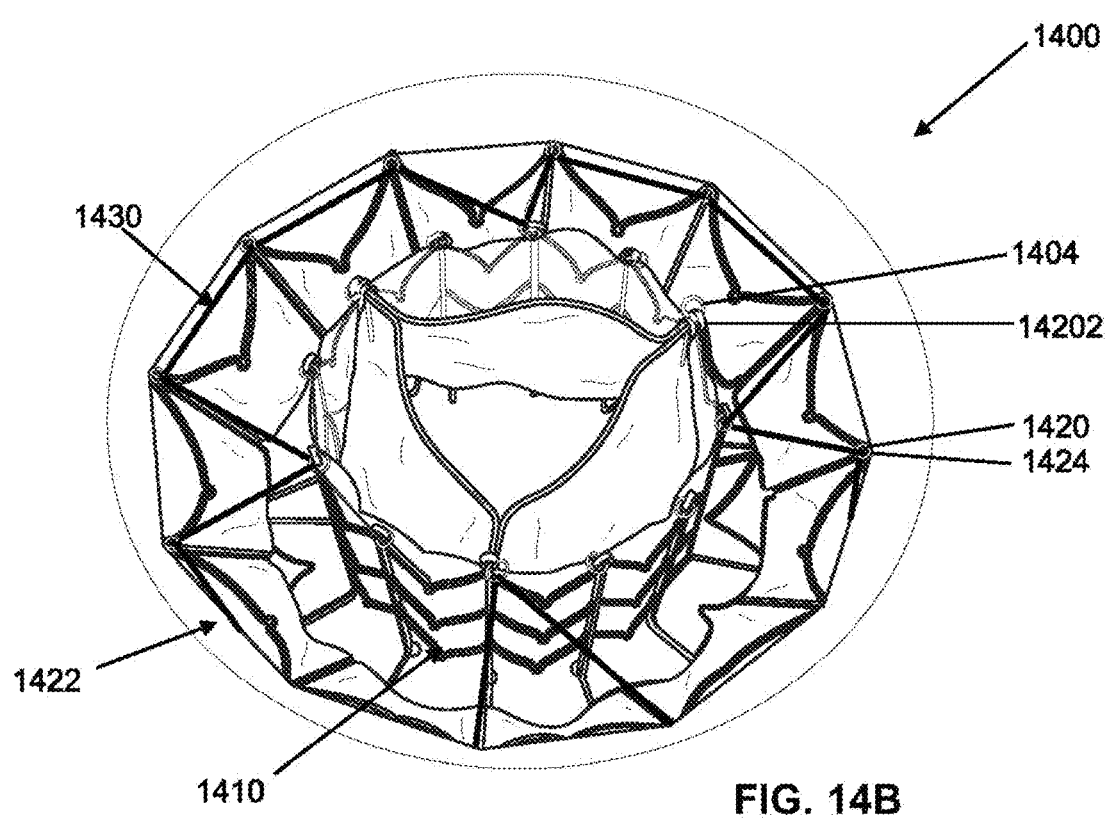

In the exemplary valve embodiments 1200, 1300 in FIGS. 12A to 13B, the eyelets 1202, 1302 were located only on the inner walls 1210, 1310 of the valves 1200, 1300, respectively. In other variations, however, as depicted in FIGS. 14A and 14B, the replacement valve and stent structure 1400 may comprise eyelets 1402, 1420 and rings 1404, 1424 on both the inner wall 1410 and outer wall 1422 of the valve 1400, or optionally only the outer wall 1422. The eyelets

1420 and rings 1424 of the outer wall 1422 may be otherwise be provided at the same range of variations and configurations as with the eyelets 1202 and rings 1212 of the inner wall 1210 as described above. In such embodiments, a second or separate tension line or loop 1426 may be provided through the outer wall 1422 eyelets 1420 or rings 1424, with respect to the loop 1414 of the inner wall 1410. In other embodiments as depicted in FIG. 14B, however, a single loop 1430 that is threaded through eyelets 1402, 1420 or rings 1404, 1424 of both the inner wall 1410 and outer wall 1422 may be provided. In this embodiment, the loop 1430 may or may not be threaded through every eyelet 1402, 1420 of the valve 1400. In FIG. 14B, for example, while every eyelet 1420 of the outer wall 1422 of the valve 1400 is looped or threated, only every third of the eyelets 1402 (four total) of the inner wall 1410 is looped. In such embodiment, only three eyelets 1402 may be provided on the inner wall 1410. Thus, in such embodiments, the valve 1400 may only be provided with eyelets where used. In some variations, the number of outer wall eyelets provided may be the same, less, or greater than the number of inner wall eyelets, as is the number of outer wall eyelets looped with delivery loop, relative to the number of inner wall eyelets.

FIG. 4A schematically depicts one example of a strut configuration 400 that may be provided on a region or wall of a stent structure. The strut configuration 400 comprises longitudinal struts 402, 404 and lateral struts 406, 408. Longitudinal strut segments 402a, 404a and lateral strut segments 406, 408 together form a closed perimeter of a stent opening or cell 410. For purposes of characterizing various geometrical configurations of the strut configuration, a longitudinal axis 410 and a transverse axis 412 are described herein, but a person of skill in the art will understand that other reference points or axis may be also be used. Longitudinal axis 410 that is parallel to the longitudinal axis of the overall stent structure, while transverse axis 412 is orthogonal to the longitudinal axis 412.

In the schematic strut configuration 400 depicted in FIG. 4A, the longitudinal struts 402, 404 may be parallel or non-parallel, depending on whether the inner lumen comprises a cylindrical or non-cylindrical shape, e.g., a frusto-conical shape. In variations, where the longitudinal struts are non-parallel, the longitudinal struts 402, 404 may have a small radial angle orientation about 1-5 degrees, 2-10 degrees, or 5 to 30 degrees from the longitudinal axis of the stent structure, so as to provide a frustoconical shape. As depicted in FIG. 4A, the longitudinal and lateral struts 402, 404, 406, 408 may comprise strut segments 402a, 402b, 404a, 404b, 406a, 406b, 408a, 408b. In some variations, the inner walls 104 of stent structures 100, the legs 406a, 406b, 408a, 408b of lateral struts 406, 408 may comprise a generally linear or straight configuration, with deformations occurring primarily at the base 406c, 406d, 408c, 408d and the bend region 406e, 408e of each lateral strut 406, 408. In some variations, where greater rigidity is desired, the lateral struts may be generally non-uniform along its length. This would be achieved by increasing the relative width near the base of the strut and decreasing the relative width in the mid-portion of the strut. The acute angle 414a, 414b, 416a, 416b between the longitudinal struts 402, 404 and the legs 406a, 406b, 408a, 408b in this strut configuration 400 may in the range of 1-45 degrees, 10-40 degrees, or 20-35 degrees. In some variations, the middle region where the pairs of legs are integrally formed may comprise a simple angle or curved configuration, but in other variations, may comprise bend regions 406e, 408e, with arcuate structures having a greater curvature 406*f*, 408*f* on the same side as the acute angle of the lateral strut, and the lesser curvature 406*g*, 408*g* found on the obtuse side of the lateral struts. The bend recess 408*h* of each bend region 406*e*, 408*c*, comprises a longitudinal length and lateral width at the lesser curvature 406*g*, 408*g*. In some variations, these lengths and widths may be configured to assist with force distribution as the stent structure is contracted into its collapsed or delivery configuration. In some examples, the bend recess may comprise a longitudinal length in the range of 50-500 microns, 50-300 microns, or 50-250 microns, and a lateral width in the range 50-500 microns, 50-350 microns, or 100-300 microns.

In some embodiments, the configuration of the lateral struts as to the orientation of the bend region and the relative configuration between the lateral strut and the longitudinal struts may vary. In the exemplary strut configuration 400 in FIG. 4A, the both bend regions are oriented toward the transition end or otherwise "pointing" to the upstream end of the valve, but in other variations, the or more bend regions may be oriented relative to the legs of the lateral strut toward the open end or downstream end of the valve.

FIG. 4B depicts another exemplary embodiment of a stent configuration 430, which comprises longitudinal struts 432, 434 and lateral struts 436, 438. Longitudinal strut segments 432*a*, 434*a* and lateral strut segments 436, 438 together form a closed perimeter of a stent opening or cell 440. Here, the legs 436*a*, 436*b*, 438*a*, 438*b* of lateral struts 436, 438 may comprise a curved or curvilinear configuration in its expanded configuration. Legs 436, 438 which have a generally convex configuration at their base 436*c*, 436*d*, 438*c*, 438*d*, and a concave configuration at their bend regions 436*e*, 438*c*. In some variations, the convex/concave configuration permits a greater amount of expansion from the delivery configuration to the expanded configuration, and/or may distribute more stress and strain more along the entire length of the strut leg. The angle 444*a*, 444*b*, 446*a*, 446*b* between the longitudinal struts 432, 434 and the straight or middle portion of each leg 436*i*, 436*j*, 438*i*, 438*j* may be in the range of 25-135 degrees, 45-90 degrees or 30-60 degrees. The bend regions may also comprise a bend recess 436*h*, 438*h* with a longitudinal length and lateral width, which can be configured to adjust the force and force distribution of the stent in its delivery and expanded configurations. The one or more bend region 436*e*, 438*e* of each lateral strut 436, 438 may also optionally comprise control apertures 436*k*, 438*k* as described elsewhere herein. In FIG. 4B, the legs 436*a*, 436*b*, 438*a*, 438*b* and bend regions 436*e*, 438*e* are also oriented in the same direction, but in FIG. 4C, the legs 466*a*, 466*b*, 468*a*, 468*b* bend regions 466*e*, 468*e* are oriented in opposite directions.

Each of the strut segments or contiguous length of longitudinal or lateral struts comprises by a lateral width or dimension, a radial height or dimension, and a cross-sectional shape. The shape may be generally square, rectangular, trapezoidal or other polygonal shape, circular or ovoid shape. The lateral width or dimension of each strut segments may be configured to provide different levels of radial force, with larger widths providing greater force, and smaller widths providing less force. In variations wherein the stent structure is formed from laser cutting of a tubular base structure, the cross-sectional shape of the strut segment relative to its elongate length may comprise a segmented annular shape, as depicted in FIGS. 2A to 3B. In the specific exemplary embodiment in FIGS. 2A and 2B, struts 200*a* and 200*b* represent struts from the outer and inner wall of a stent structures, respectively. The inner wall strut 200*b* comprises the segmented annular shape, with an outer convex curvature 202*b*, farthest from the longitudinal axis of the stent structure, that is also its greater or longer curvature, and an inner concave curvature 204*b*, closer to the longitudinal axis of the stent structure, that is also its lesser or shorter curvature, with lateral surfaces 206*b*, 208*b* that are generally linear in cross-section but with an angular axes 210*b*, 212*b* that are generally orthogonal to the longitudinal axis of the stent structure. The outer wall strut 200*a* may comprise the same or similar orientation as the inner wall strut 200*b* initially, but in embodiment where the outer wall is formed by eversion, the outer wall struts 200*a* will have an everted orientation, such that its outer curvature 202*a*, relative to the longitudinal axis of the stent structure, is concave and also its lesser curvature, while its inner curvature 204*a* that is closer to the longitudinal axis of the stent structure is convex and its greater curvature is concave. The lateral surfaces 206*a* and 208*b* have angular orientations that are skewed relative to the longitudinal axis of the stent structure, e.g., the angular axes 210*a*, 210*b* of lateral surfaces 206*a*, 208*a* do not intersect the longitudinal axis of the stent structure. These configurations are also notable in that they are located on different regions of the same longitudinal strut of a unibody folded stent structure that is formed by eversion. The corresponding transition wall strut, in its expanded state, would have a similar configuration as the outer wall strut 200*a* in a unibody folded stent structure that is formed by eversion.

Figure 2A:
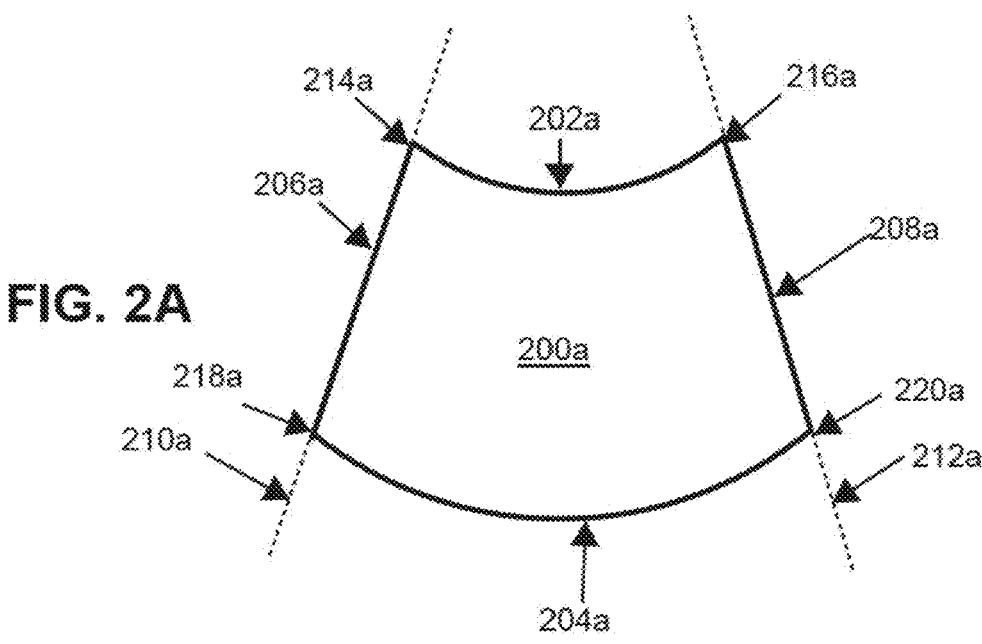
FIGS. 2A and 2B schematically depict cross-sectional configurations of struts in the outer and inner walls of an exemplary folded stent structure.
Figure 2B:
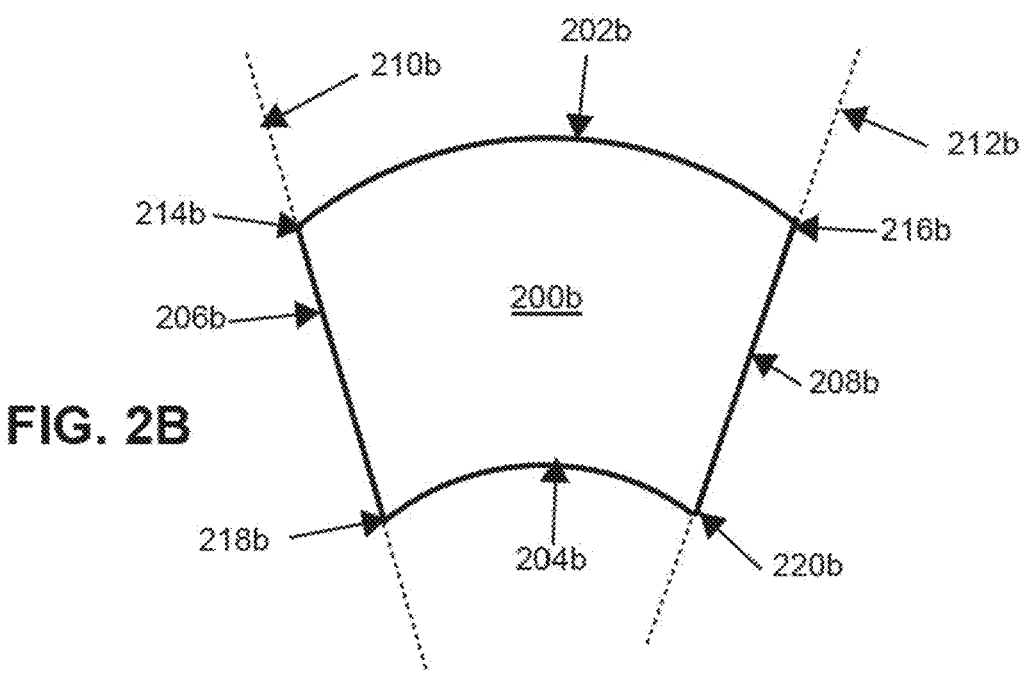
Figures 3A, 3B:
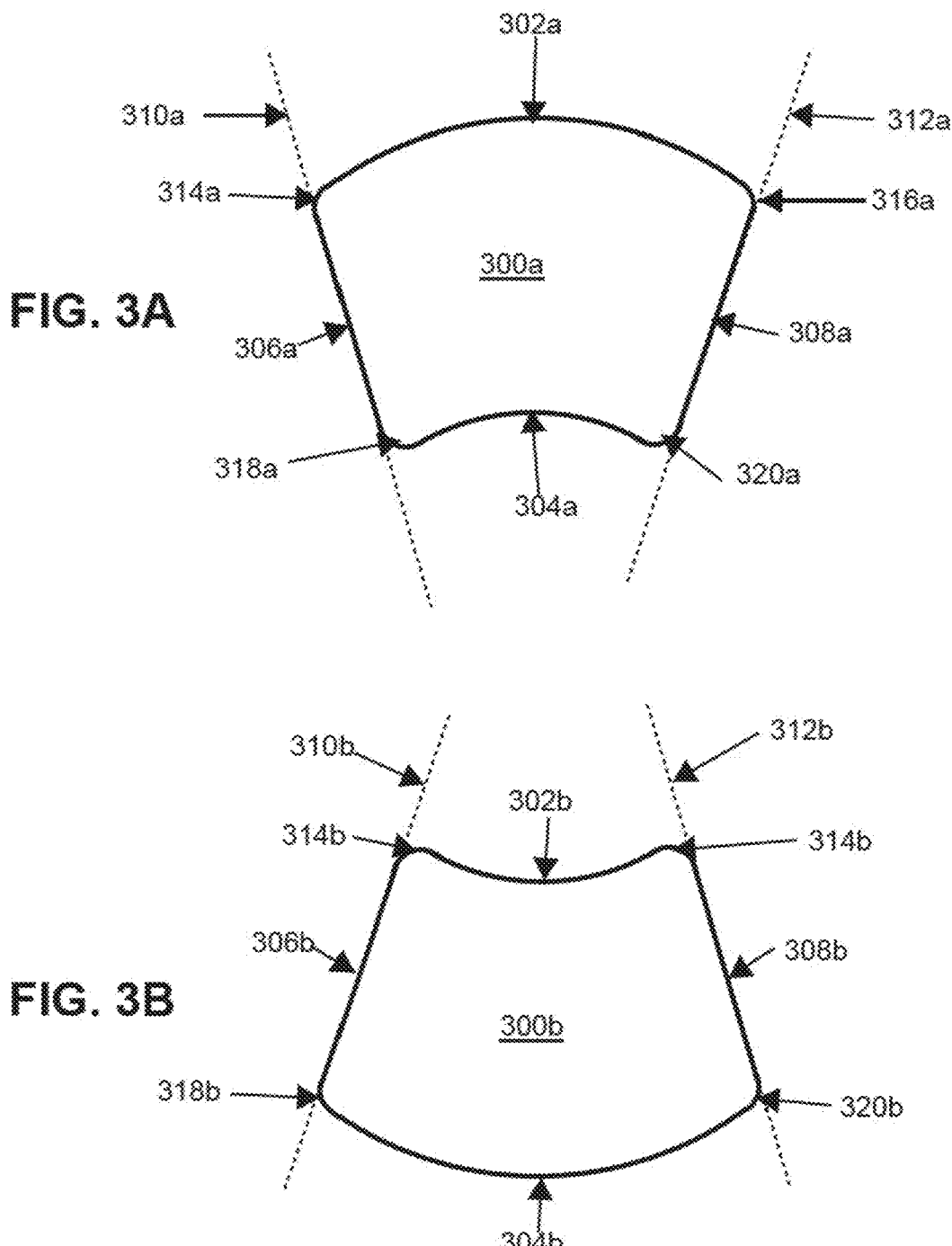
FIGS. 3A and 3B schematically depict cross-sectional configurations of struts in the outer and inner walls of another exemplary folded stent structure.

FIGS. 3A and 3B depict another embodiment of folded stent structure with a set of configurations of the struts in the outer and inner walls resulting from inversion of a laser cut tube to form the inner lumen and wall, rather than the eversion configuration depicted in FIGS. 2A and 2B. In FIGS. 3A and 3B, struts 300*a* and 300*b* represent struts from the outer and inner wall of a stent structures, respectively. The outer wall strut 300*a* comprises the segmented annular shape, with an outer convex curvature 302*a*, farthest from the longitudinal axis of the stent structure, that is also its greater or longer curvature, and an inner concave curvature 304*a*, closer to the longitudinal axis of the stent structure, that is also its lesser or shorter curvature. Lateral surfaces 306*a*, 308*a* are generally linear in cross-section but with an angular axes 310*a*, 312*a* that are generally skewed or non-intersecting to the longitudinal axis of the stent structure. The inner wall strut 300*b* may comprise the same or similar orientation as the outer wall strut 300*a* initially, but in embodiment where the inner wall is formed by inversion, the inner wall struts 300*b* will have an inverted orientation, such that its outer curvature 302*b*, relative to the longitudinal axis of the stent structure, is concave and also its lesser curvature, while its inner curvature 304*b* that is closer to the longitudinal axis of the stent structure is convex and also its greater curvature is concave. The lateral surfaces 306*b* and 308*b* have angular orientations that are skewed or non-intersecting relative to the longitudinal axis of the stent structure. Like the everted configuration of the folded stent structure, these outer and inner wall configurations are located on different regions of the same longitudinal strut of a unibody folded stent structure that is formed by inversion. The corresponding transition wall strut, in its expanded state, would have a similar configuration as the outer wall strut 200*a* in a unibody folded stent structure that is formed by inversion. In some variations, the resulting radial force in the outer wall of the stent structure may be greater with an inverted stent structure, as compared to an everted stent structure, as the everting or inverting process may weaken or adversely affect that portion of the stent structure, compared to the portion that does not undergo eversion or inversion.

The edges of the polygonal shaped struts may be rounded, smooth or sharp. In FIGS. 2A and 2B, the corners 214a-220b comprise well defined angular edges, while FIGS. 3A and 3B, the corner edges 314a-320b comprises rounded corners. The rounded corners and edges may be formed using mechanical polishing, chemical electropolishing, or multi-step combinations thereof, e.g., mechanical polishing, followed by chemical polishing or electropolishing. In some variations, the polishing may be performed before any inversion or eversion of the laser cut tubing. The dimensions and/or shape of the strut segments or struts may be uniform or may vary along its length. The radial thickness and/or the circumferential width of the struts may be in the range of 300-500 microns, 360-460 microns, or 400-500 microns. The strut thickness and/or width may or may not be uniform along the length of a strut segment. As noted previously, in some examples, relatively larger widths may be provided at the base of a circumferential strut segment, and relatively smaller widths may be provided about the middle bend regions.

The spacing between adjacent longitudinal or circumferential struts may be equal throughout the folded stent structure or may be different along the folded stent structure. For longitudinal struts, the number of struts may vary depending on the desired flexibility or radial expansion force desired for the stent structure, or based on the desired strut segment width to achieve the desired radial expansion force or flexibility. For circumferential struts, a relatively larger spacing may be provided in areas were greater radial expansion and/or reduced expansion force is desired, and small spacing in areas of reduced radial expansion and/or greater expansion force is desired.

The various stent structures described herein may comprise one or more of the following characteristics 1) a net longitudinal stent length (i.e. the maximum distance spanned by the stent along the longitudinal axis) in the range of 15-60 mm, 20-40 mm, or 25 to 35 mm;

2) a folded longitudinal stent length (e.g., the longitudinal length of the end to end contiguous longitudinal strut if completely straightened out) in the range of 40-100 mm; 50-90 mm; 60-80 mm;

3) a maximum stent diameter or transverse dimension in the expanded configuration in the range of 20-80 mm, 30-60 mm, or 45-55 mm;

4) a maximum outer end diameter or transverse dimension in the expanded configuration in the range of 25-75 mm, 35-65 mm, or 48-58 mm;

5) a maximum transition end diameter or maximum transition end transverse dimension in the expanded configuration in the range of 20-80 mm, 25-55 mm, or 40-50 mm, and is optionally less than the maximum outer end or maximum stent diameter or transverse dimension by 0-20 mm, 1-15 mm, 2-10 mm, 2-8 mm, or 2-5 mm;

6) an inner lumen length in the range of 10-50 mm, 15-40 mm, or 20-26 mm;

7) an inner lumen diameter or maximum cross-sectional dimension in the range of 10-40 mm, 15-35 mm, or 26-31 mm;

8) an inner upper radius of curvature $R_1$ in the range of 1-10 mm, 2-8 mm or 3-5 mm;

9) an inner upper bend angle in the range of 0-180 degrees, 60-135 degrees, or 75 to 90 degrees, or 83 degrees;

10) a transition wall external angle relative to the longitudinal axis of the stent structure in the range of 0-180 degrees, 45-100 degrees, 75-90 degrees, or 90 degrees;

11) a transitional wall radial width in the range of 5-30 mm, 5-20 mm, or 5-10 mm;

12) an outer upper radius of curvature $R_2$ in the range of 0.5-6 mm, 1.5 to 5 mm, or 2.5 to 4 mm;

13) an outer upper bend angle $A_2$ in the range of 45-270 degrees, 90-235 degrees, 135-200 degrees, or 160 to 200 degrees;

14) an outer wall longitudinal length in the range of 10-40 mm, 20-35 mm, or 25-30 mm;

15) an outer wall curvilinear length in the range of 10-50 mm, 20-50 mm, or 30-40 mm;

16) an outer wall longitudinal strut length from the outer end to the transition wall in the range of 12-50 mm, 20-40 mm, or 25-35 mm;

17) an outer wall middle region radius of curvature in the range of 1-15 mm, 3-12 mm, 4-8 mm, or 3-6 mm;

18) an outer wall middle region bend angle in the range of 10-180 degrees, 30-160 degrees, 60-160 degrees, or 80-140 degrees;

19) an outer wall open end region or lower region radius of curvature $R_4$ in the range of 5-100 mm, 5-40 mm, mm, or 10-20 mm;

20) an outer wall open end region or lower region bend angle $A_4$ in the range of 1-90 degrees, 10-90 degrees, 20-80 degrees, or 30-70 degrees;

21) a maximum radial difference between the smallest radius and largest radius in the same radial plane of the outer wall of the stent structure is in the range of about 6-15 mm, 8-12 mm, 9-11 mm, or about 10 mm;

22) a first end/atrial/upper region maximum radius of the outer wall in the range of 20-30 mm, 22-28 mm, or 24-27 mm;

23) a middle region minimum radius of the outer wall in the range of 10-30 mm, 12-25 mm, or 15-20 mm;

24) a second end/ventricular/lower region maximum radius of the outer wall in the range of 20-35 mm, 25-30 mm, or 26-29 mm;

25) a longitudinal length to diameter ratio in the range of 0.40 or 1.0, 0.45 to 0.80, or 0.50 to 0.60;

26) a number of longitudinal struts that is divisible by 3, e.g., selected from a group consisting of one or more of 3, 6, 9, 12, 15 longitudinal struts;

27) a ratio between the radial distance between the barb tip and the longitudinal axis of the stent structure, and the radial distance between an adjacent longitudinal strut or outer wall segment (excluding the barb) and the longitudinal axis of the stent structure, in the range of 1.1 to 1.5, 1.05 to 1.30, 1.05 to 1.20, or 1.05 to 1.15; and/or 28) an inner opening position relative to the outer opening position along the longitudinal axis that is positive (i.e. protrudes from the outer opening), neutral (i.e. flush with the outer opening), negative (i.e. recessed from the outer opening), and/or in the range of −4 to −12 mm, −5 to −10 mm, −6 to −9 mm, +1 to +8 mm, +2 to +6 mm, +3 to +5 mm, −3 to +3 mm; +0 to +3 mm, −12 to +5 mm, −6 to +6 mm, or −7 mm to +4 mm.

The scope of stent structures described herein need not be limited so as to require a selection of each characteristic recited above, and single characteristics or a subset of characteristics are also contemplated. For example, in some variations, the stent structure, which may or may not be provided with the valve and/or skirt material, may be:

1) a folded unibody stent structure with an everted outer wall strut configuration or an inverted inner wall strut configuration;

2) a folded unibody stent structure and wherein the number of longitudinal struts divisible by 3; with a non-foreshortening inner lumen, and optionally a fore-shortening outer wall, with a radial strut thickness in the range of 400-450 microns and a longitudinal length to diameter ratio in the range of 0.50 to 0.60;

3) a folded unibody stent structure comprising an upper inner radius of curvature that is smaller than the upper outer radius of curvature, an inner lumen that extends from the outer opening of the outer wall by 0 to 3 mm, and a barb to outer wall radius ratio in the range of 1.1 to 1.2; or 4) a folded double-wall unibody stent structure 12 longitudinal struts and 3-5 circumferential struts in the inner lumen, 1-2 circumferential strut in the transition wall and 3-5 circumferential struts in the outer wall.

In the embodiment depicted in FIGS. 1A to 1G, the stent structure 100 comprises a plurality of end-to-end longitudinal struts and a plurality of circumferential lateral struts, each in turn comprising a contiguous set of contiguous longitudinal or lateral strut segments, respectively. In the particular example of stent structure 100, twelve equally spaced apart end-to-end longitudinal struts are provided, and nine sets of complete circumferential struts along the folded stent structure 100. Four sets of closely spaced circumferential struts are provided along the inner wall, with relatively straight or minimally curved legs and with their middle bends oriented to point toward the upper or closed end of the stent structure. The transition wall 108 comprises one set of circumferential struts with a relatively increased base curvature in each leg and a relatively reduced curvature about the middle bend oriented to point radially outward toward the outer wall 106. The outer wall 106 comprises four sets of circumferential struts, with their middle bends oriented toward the closed end of the stent structure 100, except for the set of circumferential struts closest to the opening of the outer wall 106, which may be oriented toward the open end of the stent structure 100. The orientation of the legs and middle bends in the third set of circumferential struts also deviates radially outward relative to the adjacent longitudinal struts to provide barb-like or force concentration structures resist displacement of the strut structure relative to the native valve tissue. Typically, these radially outward displaced circumferential struts may be provided at one or more circumferential struts that are closest to the portion of the outer wall between the narrowest diameter and the downstream or open end of the stent structure, and oriented toward the narrowest diameter or inlet/upstream end of the stent structure, as shown in FIGS. 1A and 1C.

As noted previously, control apertures are also provided at the outer end of, or at the junction of the longitudinal struts and the circumferential strut at the outer end of the stent structure 100, and at the inner end of, or at the junction of the longitudinal strut and the circumferential strut at the inner end of the stent structure, at the inner lumen. Control apertures are also provided at the middle bends of the two circumferential struts closest to the outer end of the stent structure 100.

For stent structure 100, the net longitudinal stent length may be 25 to 35 mm, the folded longitudinal stent length may be 60-90 mm, the maximum stent diameter or transverse dimension in the expanded configuration may be 45-55 mm, the maximum outer end diameter or transverse dimension in the expanded configuration may be 45-55 mm, the maximum transition end diameter or transverse dimension in the expanded configuration may be 40-50 mm, and may be less than the maximum outer end or maximum stent diameter or transverse dimension by 1-5 mm, the inner lumen length may be 20-25 mm, the inner lumen diameter or maximum cross-sectional dimension is 20-30 mm, the inner upper radius of curvature may be 3-5 mm, the inner upper bend angle may be 90 to 105 degrees, the transition wall external angle relative to the longitudinal axis of the stent structure may be 75-90 degrees, the transitional wall radial width may be 15-20 mm, the outer upper radius of curvature in the range may be 1 to 4 mm, the outer upper bend angle may be 160 to 200 degrees, the outer wall longitudinal length may be 20-25 mm, the outer wall curvilinear length may be 25-40 mm, the outer wall longitudinal strut length from the outer end to the transition wall may be 25-35 mm, the outer wall middle region radius of curvature may be 3-6 mm, the outer wall middle region bend angle may be 60-120 degrees, the outer wall open end region or lower region radius of curvature may be 10-50 mm, 10-30 mm, or 10-20 mm, the outer wall open end region or lower region bend angle may be 20-135 degrees, 30-90 degrees, or 50-70 degrees, the maximum radial difference between the smallest radius and largest radius in the same radial plane of the stent structure may be 9-11 mm, and/or the inner opening position relative to the outer opening position along the longitudinal axis that is negative may be −6 to −9 mm.

In FIGS. 1A to 1F, the stent structure 100 also comprises twelve contiguous longitudinal struts, and nine circumferential struts as with stent structure 100. Stent structure 100 comprises four circumferential struts along the inner lumen 102, but in other variations may have two, three, five or six circumferential struts in the inner lumen. While the orientations of the circumferential struts in the inner wall 104 are also pointed toward the closed end of the stent structure 100, and the circumferential strut of the transition wall 108 are oriented radially outward, in some variations, one or more circumferential struts that are oriented radially inward and/or toward the open end of the stent structure, e.g., the circumferential strut closest to the open end of the outer wall. Other optional variations may include a transition wall with has an orthogonal orientation relative to its longitudinal axis, while the transition wall 108 of stent structure 100 is slight or substantially angled. It is hypothesized that an inwardly angle transition wall may reduce turbulence or non-laminar flow into the opening of the inner lumen, or peak axial forces that may dislodge the stent structure from the target location during atrial contraction.

In several of the embodiments described herein, the upper end or transition end of the stent structure is configured to be used as the upstream end of the replacement valve, with blood flow received in the transition end of the inner lumen and to pass through the valve structure attached to the inner lumen. The valve structure may be any of a variety of valve structures, including a flap valve, ball-in-cage valve, or a leaflet valve. The leaflet valve material may comprise an autologous, homologous or heterologous or artificial material, e.g., a natural material or anatomical structure, such as porcine, bovine or equine pericardial tissue or valve, or biomaterials derived from the patient's own cells, and may be fixated with any of a variety of chemicals, such as glutaraldehyde, to decrease the antigenicity of the valve and/or to alter the physiological and/or mechanical properties of the valve materials. Where a leaflet valve is provided, the leaflet valve may be a bi-leaflet or tri-leaflet valve structure. The commissures of the valve may be attached or sutured to the longitudinal and/or circumferential struts of the inner lumen, e.g., every fourth longitudinal strut of the stent structures 100 provided with a tri-leaflet valve.

The replacement valve may further comprise one or more skirt materials to one or more regions of the stent structure. The skirt materials may comprise solid, tight weave, or loose knit woven sheet of autologous, homologous or heterologous or artificial material that may be the same or different from the leaflet material of the valve. The skirt material may comprise polytetrafluoroethylene (PTFE), polyester or polyethylene terephthalate (PET) material. In variations comprising open pore materials, the average pore size may be in the size range of about 0.035 mm to 0.16 mm, or 0.05 mm to 0.10 mm, or 0.07 mm to 0.09 mm. The open pore materials may provide greater elasticity or flexibility in regions of the stent structure that undergo greater configuration change. Other regions of the stent may be provided with a solid sheet materials, lacking pores, where elasticity or flexibility are not needed. The skirt material may comprise a single layer or a multi-layer structure, and comprise one or more coatings to modulate thrombus formation, tissue ingrowth, and/or lubricity.

Figure 5A:
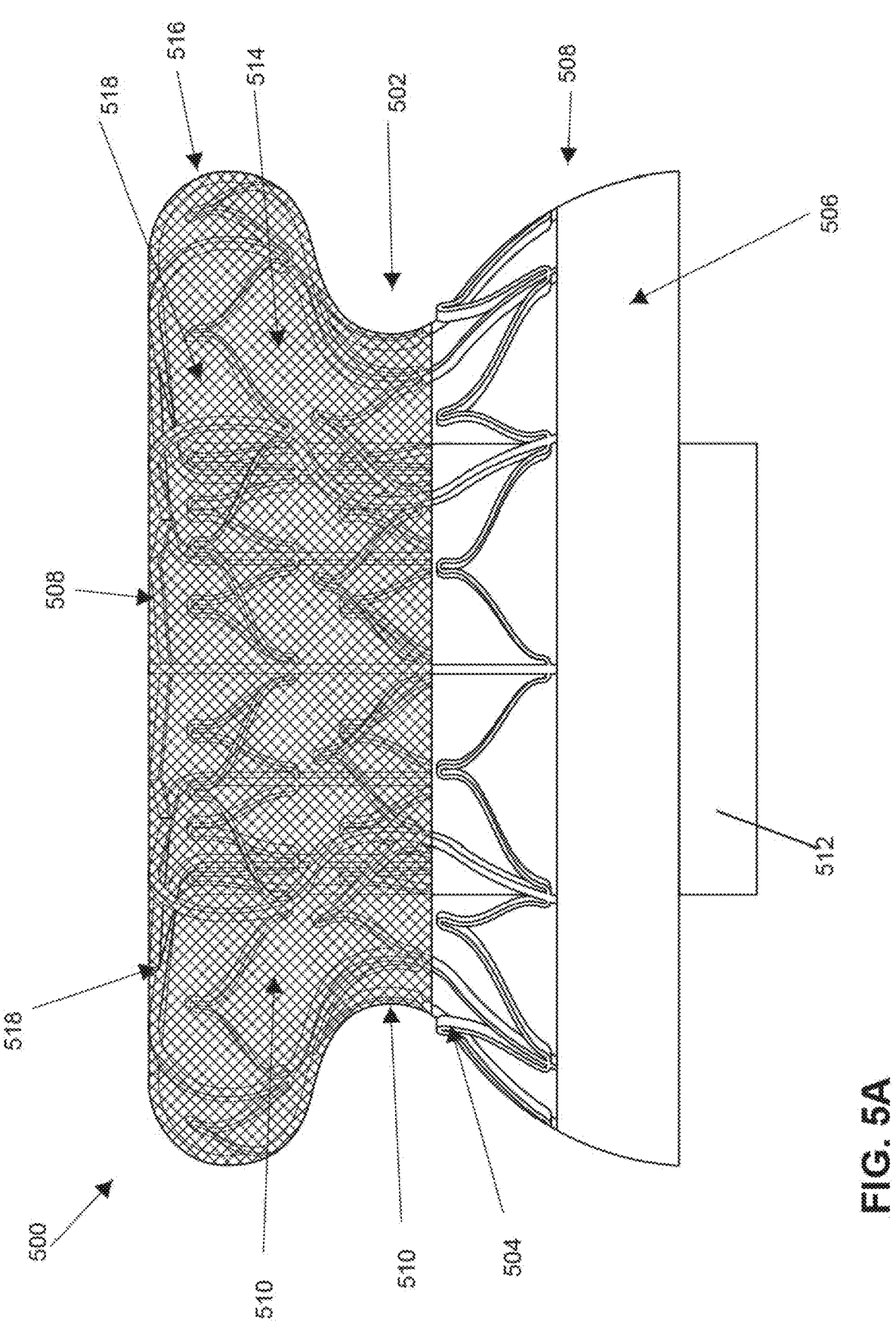
FIG. 5A is a schematic side elevation view of another embodiment of a heart valve stent with the leaflet valve and skirt attached.
Figure 5B:
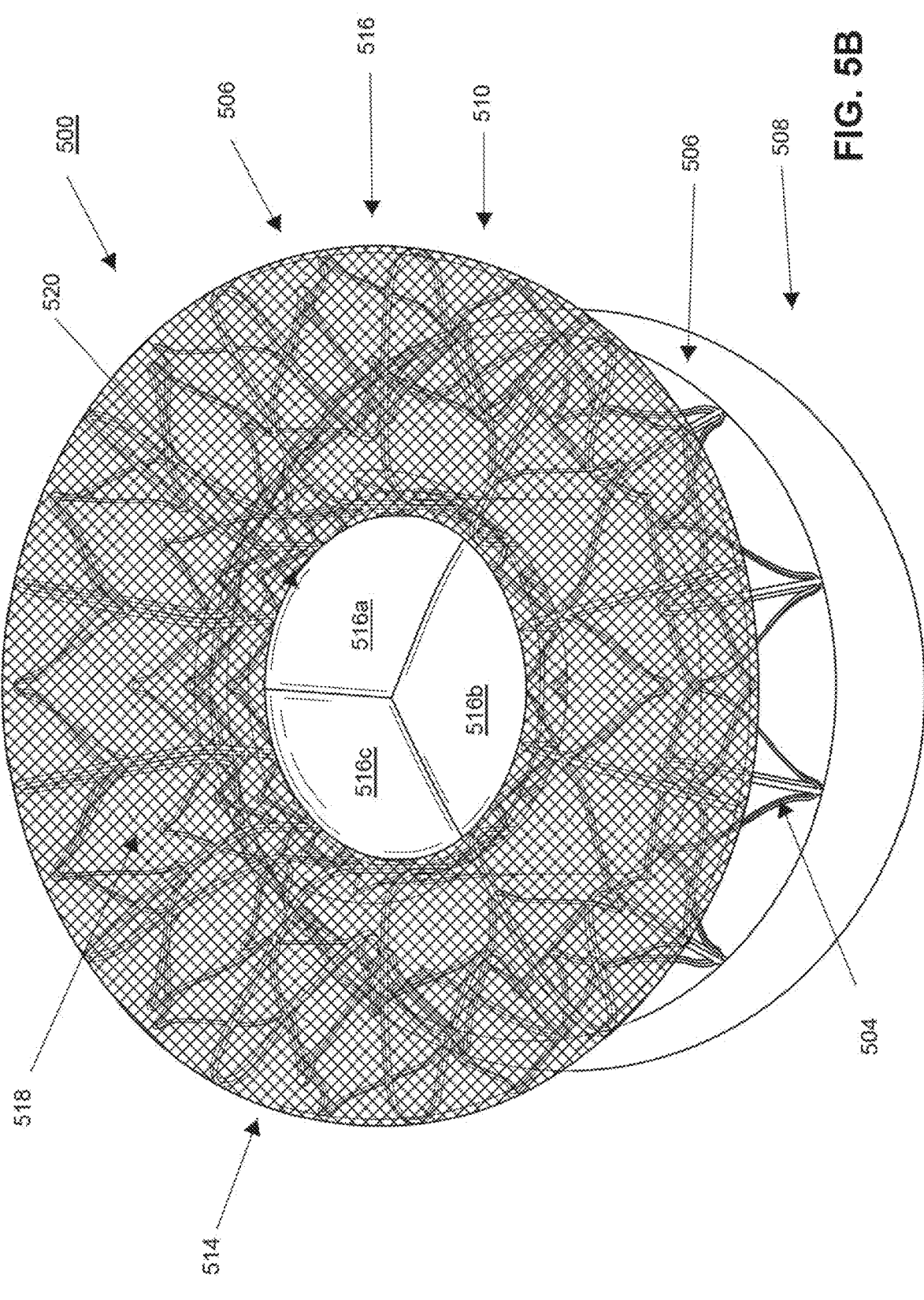
FIGS. 5B and 5C are schematic bottom and top perspective view of the heart valve stent in FIG. 5A.
Figure 5C:
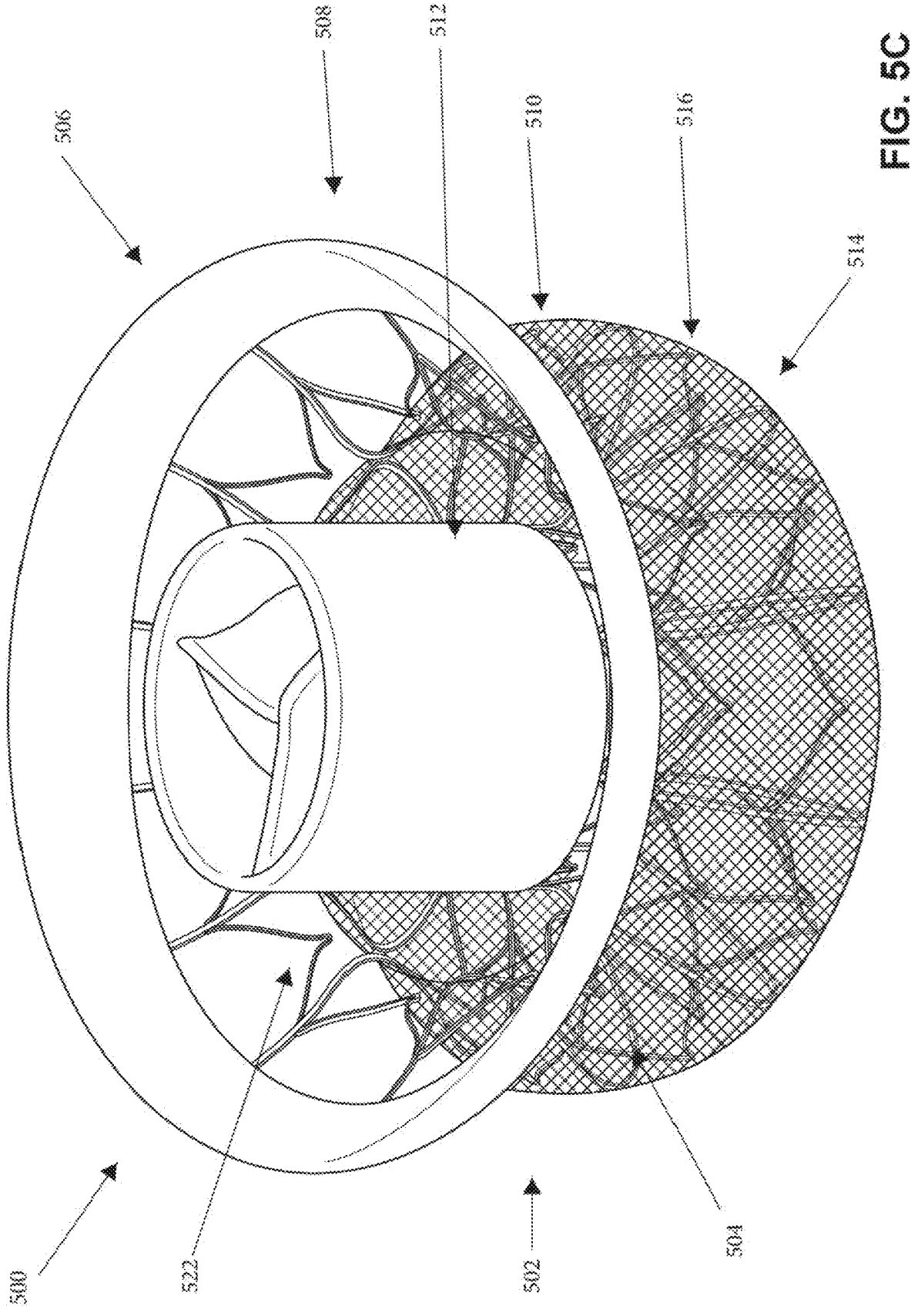
Figure 5D:
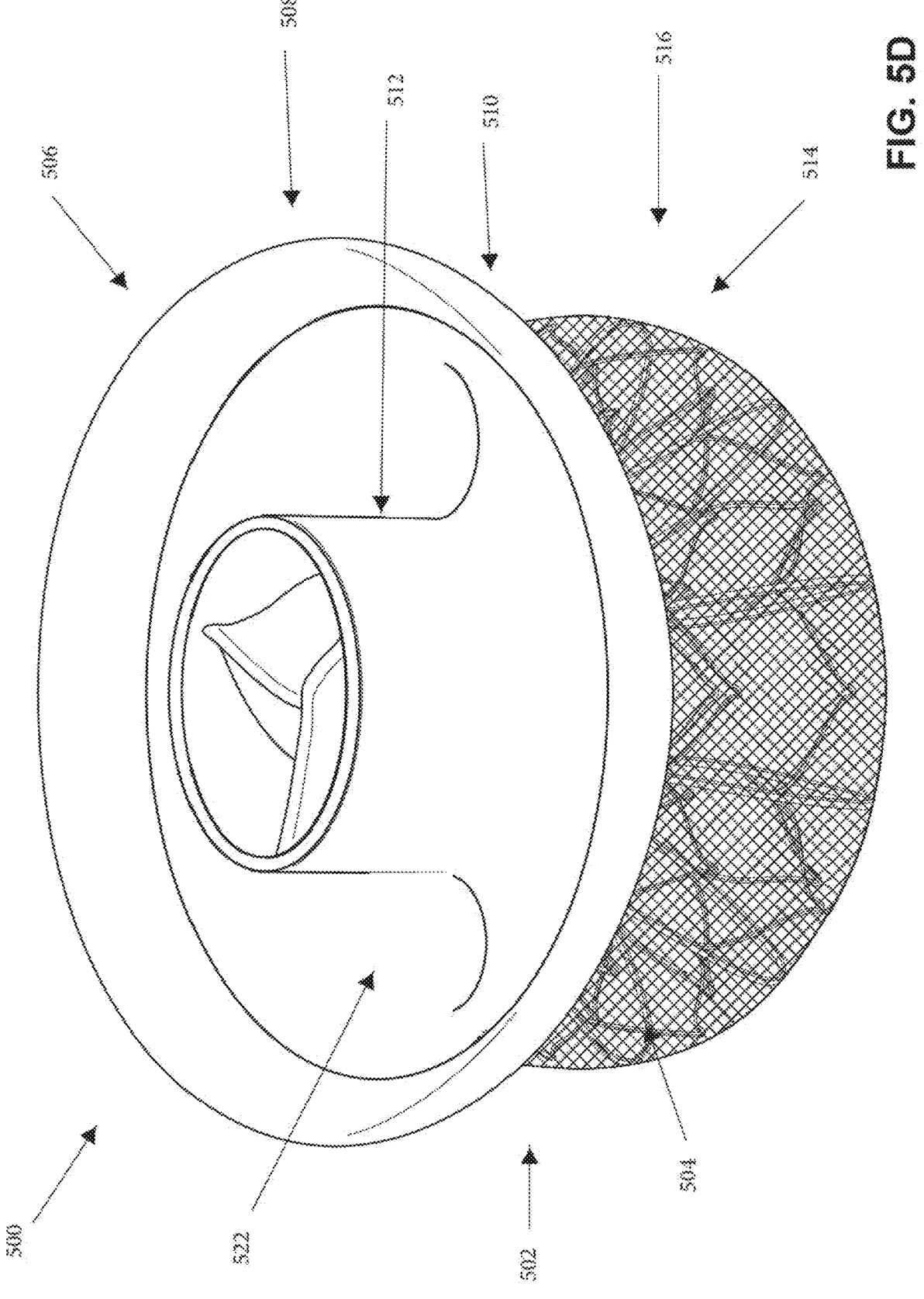
FIG. 5D is a schematic top perspective view of a variant of the cuff structure in FIG. 5C.
Figure 6A:
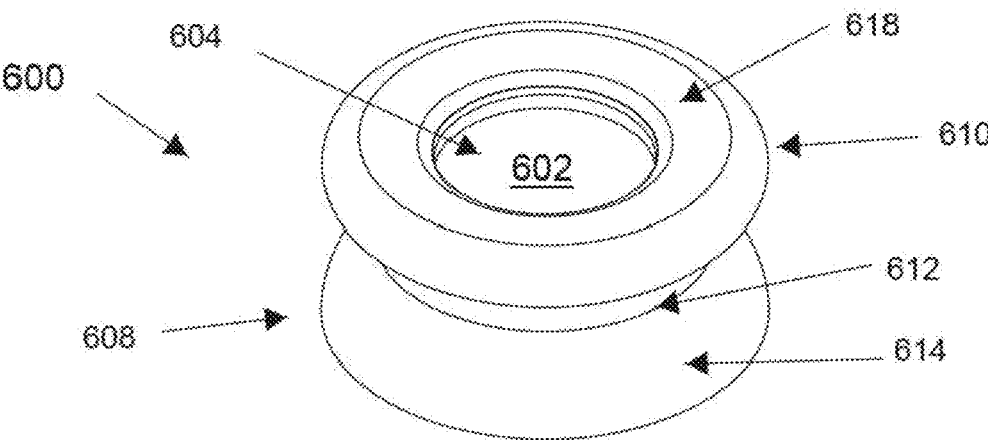
FIGS. 6A to 6C are top perspective, top plan and side elevation views of a skirt structure for use with a heart valve stent.
Figure 6B:
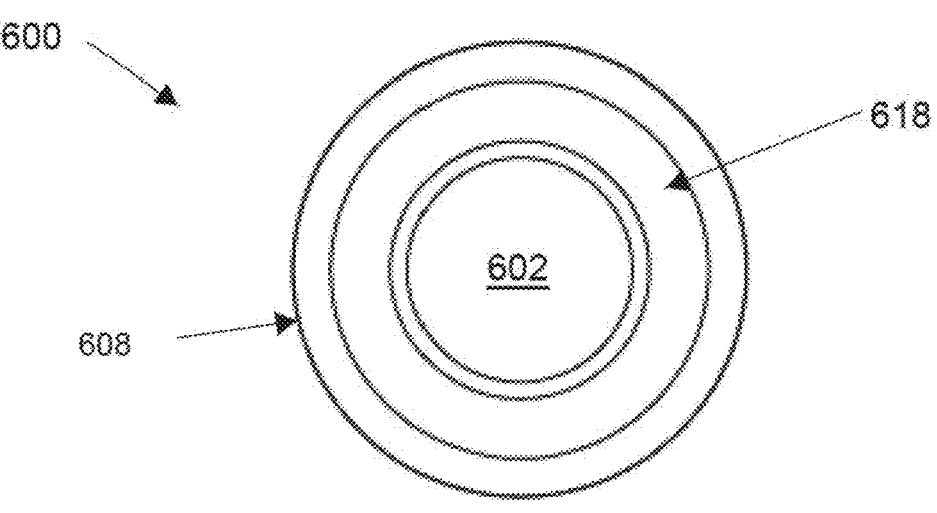
Figure 6C:
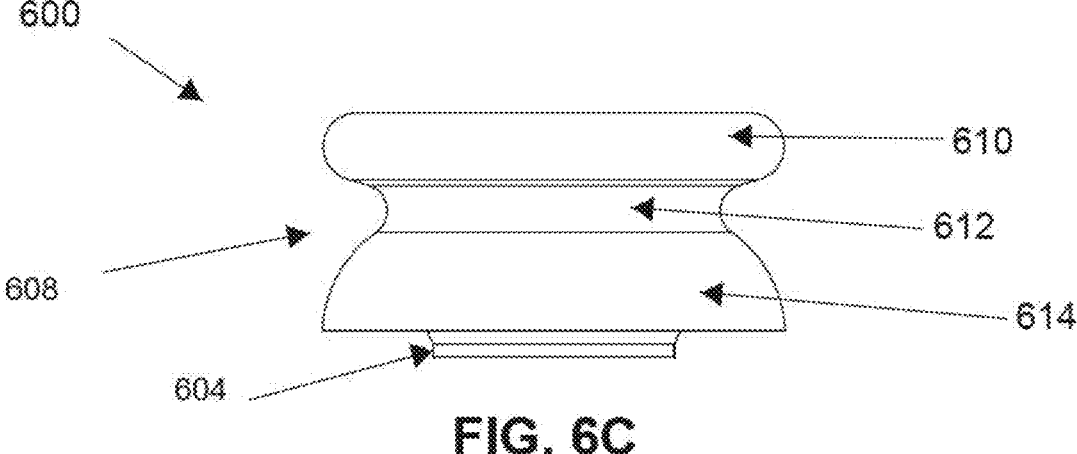
Figure 6D:
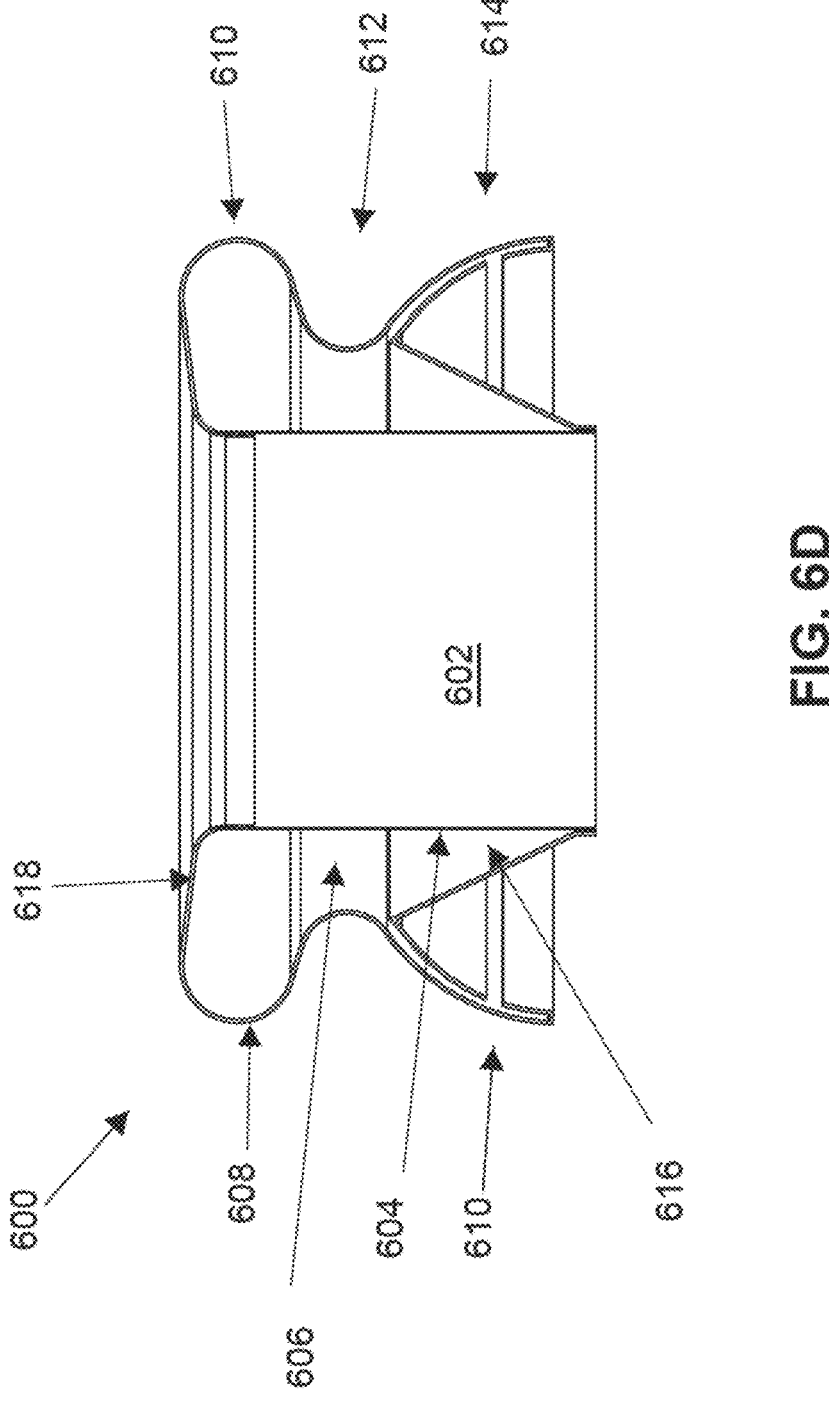
FIG. 6D is a cross-sectional view of the skirt structures in FIGS. 6A to 6C.

FIGS. 5A and 5B depict one example of a replacement valve 500 with a skirt 502 comprising two different materials attached to the stent structure 504. In this particular embodiment, a solid or tight weave material is provided as a cuff structure 506 around the outer and inner surfaces of the downstream or lower region 508 of the outer wall 510. The same or a different cuff structure of the solid or tight weave material is provided on the outer surface of the inner wall 512. FIG. 5C depicts a variant with separate material for the inner wall 512, and FIG. 5D depicts another variant with the same cuff structure spanning the annular cavity 522 and covering the outer surface of the inner wall 512. A porous knit material is used for another cuff structure 514 around the upper region 516 of the outer wall 510, the transition wall 518 and to the upstream opening 520 of the inner wall 512 of the stent structure 504. An artificial or animal-derived material may be used to form the valve pockets and valve leaflets 516a-c located in the inner lumen 512. In addition to provide elasticity to expand with the expansion of the stent structure, the porous knit material may also provide for cellular migration and tissue ingrowth into the replacement valve. This dual material skirt 502 permits blood that flows into the annular cavity 522 of the to pass through the porous material of cuff structure 514, but the porous material may be provided with a porosity that is small enough to resist the passage of thrombus that might have formed.

In another variation, depicted in FIGS. 6A to 6D, the skirt 600 comprises a tubular material. The shaped skirt 600 may provide a more consistent attachment of the skirt 600 to a stent structure with less potential problems with excess sheet material in narrower stent regions, in this particular variation, the skirt 600 comprises an internal central cavity 602 formed by an inner wall 604, and an internal annular cavity 606 between the inner wall 604 and the shaped outer wall 608. The outer wall 608 may be shaped to a complementary configuration to the outer wall of the stent structure, e.g., an expanded upstream region 610, a reduced diameter middle region 612, and an enlarged diameter downstream region 614. The skirt 600 is placed over the closed end of the stent structure so that the stent structure is located in the annular cavity 606 and where the inner wall 604 of the skirt 600 is positioned inside the inner lumen of the stent structure. In some variations, the inner wall 604 may be inverted into the inner lumen of the stent structure. A tapered annular skirt 616 may be provided to span the annular cavity 606 between the inner wall 604 and the shaped outer wall 608. The outer wall 608 of the skirt 600 may comprise a porous or knitted material that may be heat set into the expanded configuration and span the entire outer wall 608, the transition wall 618 of the skirt 600 and optionally a portion of the inner wall 604, where it is sewn, adhered, and/or welded to a tubular tight weave material configured to line the inner lumen of the stent structure. The tapered annular skirt 616 may also be sewn, adhered welded or otherwise attached to the inner surface of the outer wall 608 and the outer surface of the inner wall 604 after the outer wall 608 and inner wall 604 are initially assembled with the stent structure. Similarly, the valve leaflet structure may be sewn, adhered welded or otherwise attached to the inner wall 604 of the skirt 600, after the inner wall 604 is inserted into the inner lumen of the stent structure.

The skirt materials may be sutured against the outer and/or inner surfaces of the inner wall, transition wall, and/or outer wall of the stent, and in some variations may be provided as a cuff or folded structure over the outer end, inner end or transition wall of the stent structure to span over the inner and outer surfaces of a stent wall, or to transition from an inner or outer surface of one wall to another wall, e.g., lining the annular cavity of the replacement valve, so as to cover the inner surface of the outer wall, the inner surface of the transition wall and the outer surface of the inner wall, for example.

Figure 15:
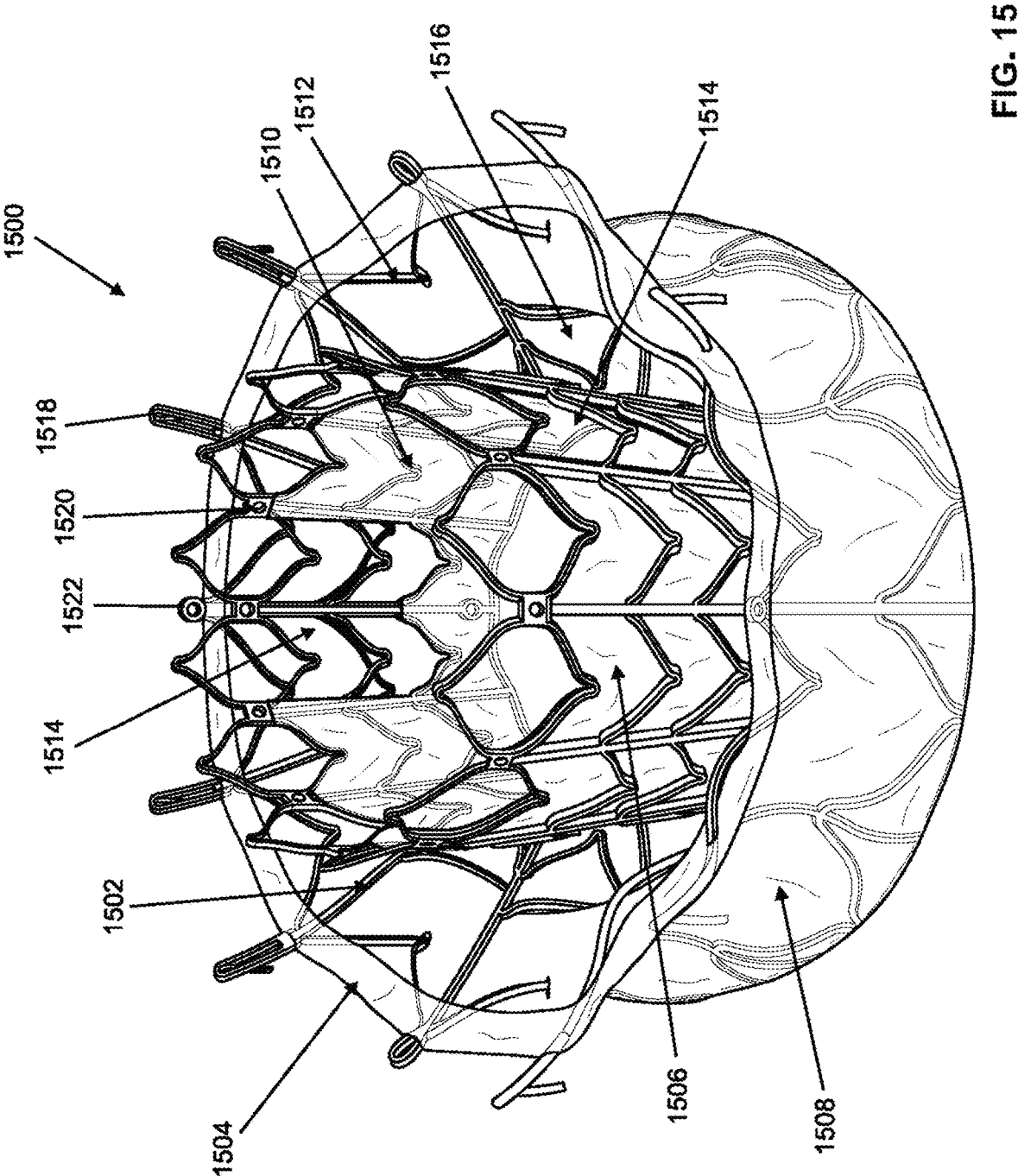
FIG. 15 depicts another variation of a replacement heart valve comprising inset barbs, eyelets and valve skirt openings or cut-outs.

FIG. 15 depict another exemplary embodiment of a replacement valve 1500, comprising a stent frame 1502 and valve assembly 1504. For illustrative purposes, the valve leaflets have been omitted from the figure, so that only inner skirt 1506 and outer skirt 1508 valve skirts of the valve assembly 1504 are depicted. In this embodiment, the inner skirt 1506 lining the inner wall 1510 and/or outer skirt 1508 covering the outer surface of the outer wall 1512 comprises a polymeric material as disclosed earlier, and may be a knit or woven fabric comprising PET or PET/ultra-high molecular weight polyethylene hybrid material. In some variations, a woven material may be used when reduced porosity or sealing material is desired, while a knit material may be used when greater porosity or tissue ingrowth is desired. In the particular embodiment depicted the inner skirt 1506 further comprises one or more cut-outs or openings 1514 which are located between the valve commissures. It is hypothesized that retrograde flow into the open end of the valve 1500 can fill the annular cavity 1516 between the inner and outer walls 1510, 1512 of the valve 1500 and the be directed through the through the skit openings 1514 toward the valve leaflets (not shown). This increased flow toward the valve leaflets may improve the force and speed of valve closure, which may improve leaflet kinematics and valve hemodynamics. This particular embodiment is also depicted with exemplary inset barbs 1518 and eyelets 1520, 1522 as described elsewhere herein, though with eyelets 1520, 1522 are depicted without any rings, for illustrative simplicity.

Figure 7A:
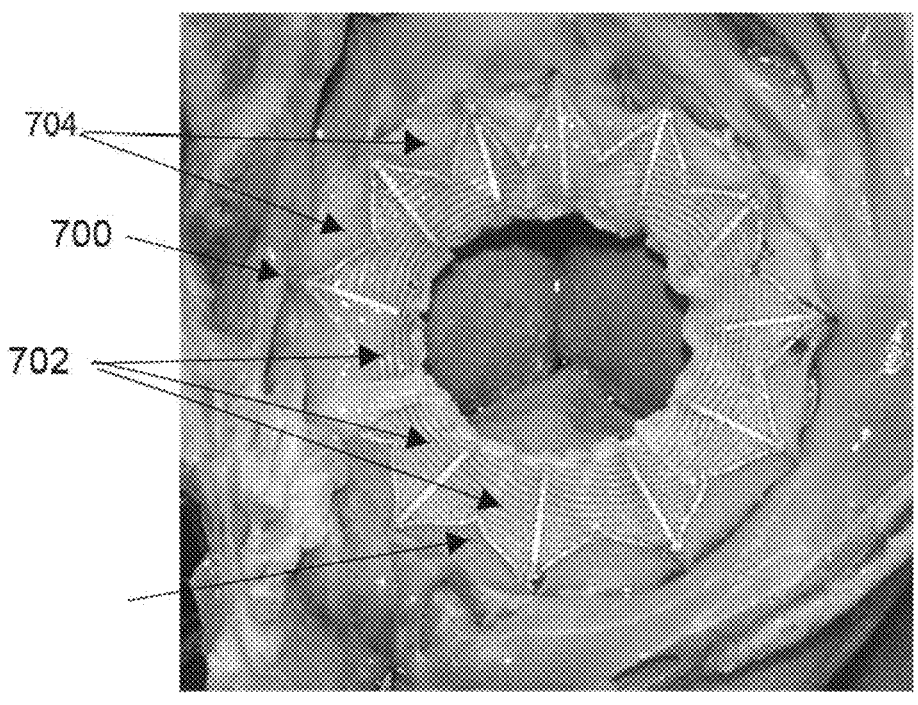
FIGS. 7A and 7B are atrial/top and ventricular/bottom views of an implanted heart valve.
Figure 7B:
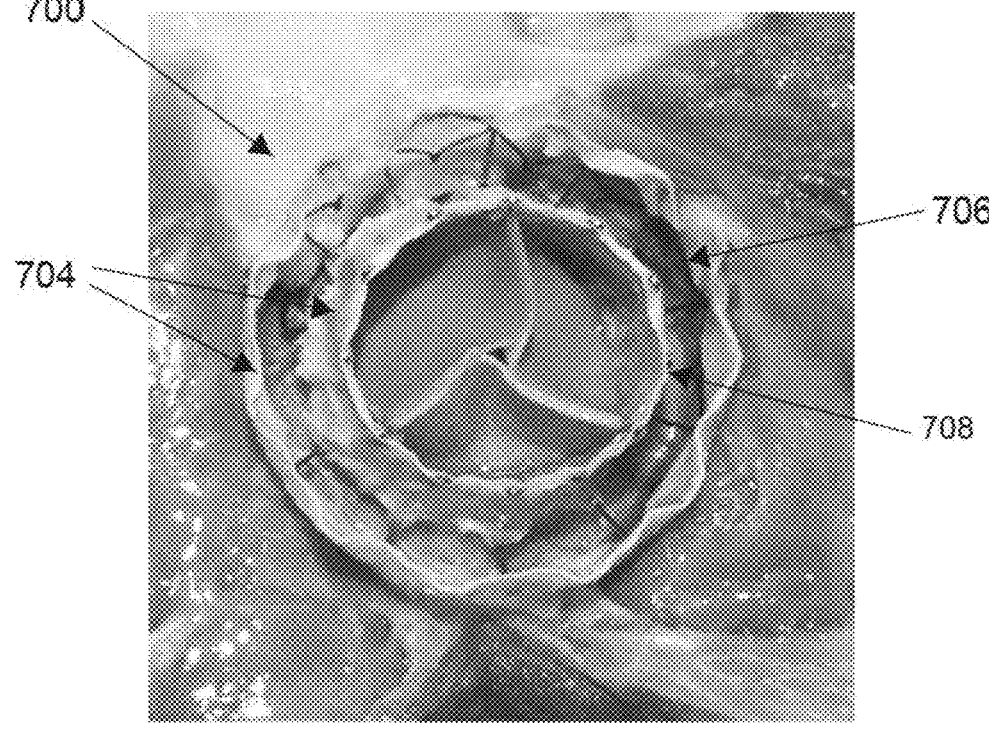

FIGS. 7A and 7B are photographs of an exemplary replacement valve 700 with a dual material skirt as described with respect to FIGS. 5A and 5B above, used in a mitral valve animal study, explanted after 30 days. On the atrial side of the valve 700 depicted in FIG. 7A, tissue or cellular ingrowth into the large pore knitted fabric 702 was found, as well as good ingrowth at the boundary or junction between the large port knitted fabric 702 and the tight weave fabric, while on the ventricular side of the valve 700, which is primarily covered by a small pore tight weave fabric 704 about the outer and inner openings 706,708, good tissue ingrowth is noted.

Figure 16A:
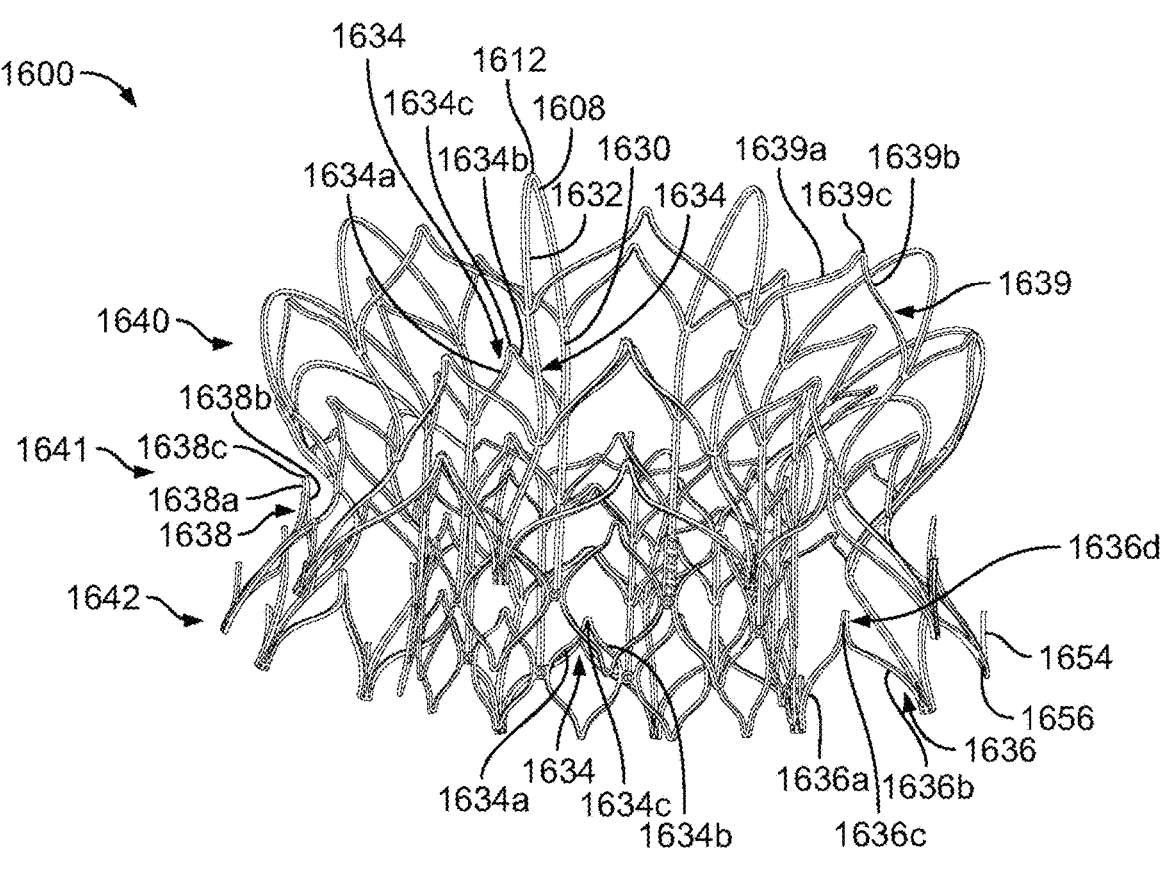
FIG. 16A depicts a schematic perspective view of a stent structure of a replacement valve, according to one embodiment of the present disclosure.
Figure 16B:
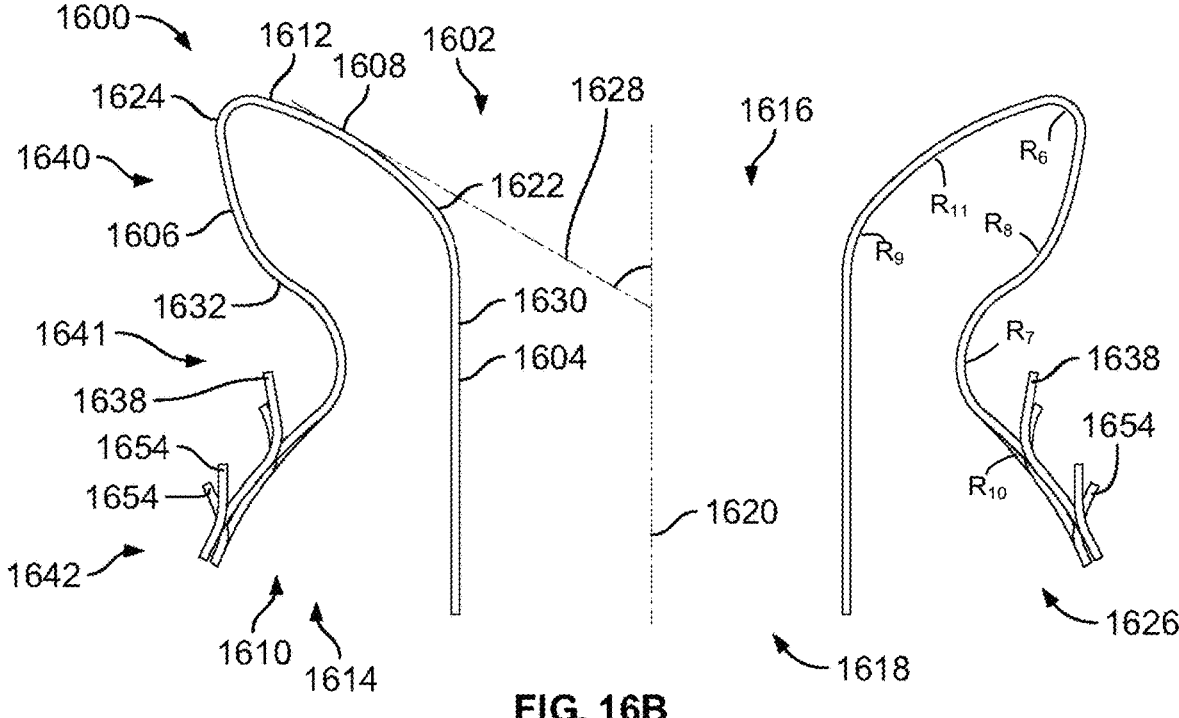
FIG. 16B depicts a cross-sectional view of the stent structure of FIG. 16A.

An exemplary embodiment of a stent structure or frame 1600 is depicted in FIGS. 16A and 16B in an expanded configuration. While not illustrated, the stent structure 1600 may be collapsed into a collapsed configuration. In some embodiments, the stent structure 1600 may self-expand when not constrained. FIG. 16A illustrates a perspective view of the stent structure 1600 and FIG. 16B illustrates a cross-sectional view of the stent structure 1600.

The stent structure 1600 comprises an inner lumen 1602 formed by an inner wall 1604. An outer wall 1606 is spaced radially apart from the inner wall 1604 via a transition wall 1608, and forms an annular cavity 1610. The inner wall 1604 and the outer wall 1606 form a folded double wall. The transition wall 1608 may result from the folding, inversion, or eversion of a single tubular structure into a double-wall unibody tubular stent frame or structure. In the illustrated embodiment, the transition wall 1608 may extend radially outward. The stent structure 1600 has a first closed end 1612 that is located at the transition wall 1608, and a second open end 1614 of the outer wall 1606, wherein the annular cavity 1610 is open and accessible. Due to an angle 1628 of the transition wall 1608, the first closed end 1612 is tapered.

The inner lumen 1602 comprises a first opening 1616 surrounded by the transition wall 1608 and a second opening 1618 at the second open end 1614 of the stent structure 1600. In the illustrated embodiment, a longitudinal axis 1620 of the inner lumen 1602 is coincident with a central axis of the stent structure 1600. In some embodiments, the inner lumen 1602 may be eccentrically located relative to the outer wall 1606 of the stent structure 1600. The inner lumen 1602 typically comprises a circular cross-sectional shape with a generally cylindrical shape between the first opening 1616 and the second opening 1618, as depicted in FIGS. 16A and 16B. In other examples, the inner lumen 1602 may comprise a frustoconical, oval or polygonal shape. In some variations, the stent structure may comprise an inner lumen where the size and/or shape of the first and second openings may be different. In embodiments where the inner lumen comprises a non-cylindrical shape.

The location of the first and second openings 1616, 1618 of the inner lumen 1602 relative to the overall stent structure 1600 may also vary. In the illustrated embodiment, the first opening 1616 of the inner lumen 1602 is recessed relative to the first closed end 1612, as depicted in FIGS. 16A and 16B. Due to the first closed end 1612 being tapered, the first opening 1616 is also tapered as the first opening 1616 extends away from the inner wall 1604. In other examples, the first opening 1616 may be generally flush with the transition wall 1608 of the stent structure 1600. The location of the first opening 1616 may also be characterized as recessed, flush or protruding relative to the longitudinal location of an inner junction 1622 between the inner wall 1604 or lumen 1602 and transition wall 1608, or relative to the outer junction 1624 between the transition wall 1608 and the outer wall 1606, as depicted in FIG. 16B. Likewise, the second opening 1618 of the inner lumen 1602 may also be characterized as recessed, flush or protruding, relative to the longitudinal location of outer opening 1626 of the outer wall 1606. For example, with stent structure 1600, the second opening 1618 of the inner lumen 1602 comprises an offset or protruding location relative to the outer opening 1626 of the outer wall 1606. In some variations, the inner lumen 1602 may protrude relative to the second open end 1614 of the outer wall 1606 in variations where a smaller or shorter outer wall 1606 is preferred to accommodate smaller size native valve anatomy. The inner lumen 1602 size, however, may remain relatively the same size between different size variations, to provide consistent valve geometry and/or hemodynamic characteristics.

As discussed above, the transition wall 1608 of the stent structure 1600 generally extends radially outward at a pre-determined angle 1628 and surrounds the inner lumen 1602 in the expanded configuration, but in other variations may have a different shape and/or surface angle. In the illustrated embodiment, the transition wall 1608 also comprises a curved shape, e.g., a concave or convex shape. In other variations, the transition wall 1608 may have a generally orthogonal angle relative to the longitudinal axis of the inner lumen 1602. Referring back to FIG. 16B, the transition walls 1608 of stent structure 1600 may form an external acute angle 1628 relative to the longitudinal axis 1620 of the inner lumen 1602. The angle 1628 may be in the range of +45 to +89 degrees, +75 to +89 degrees, or +81 to +85 degrees, with optional variances in the range of ±1 degree, ±2 degrees, ±3 degrees or ±4 degrees. In other variations, the transition wall angles may be in the range of −45 to +45 degrees, −75 to +75 degrees, or −85 to +85 degrees.

The stent structure 1600 comprises a plurality of inte-grally formed stent struts, such as longitudinal struts 1630, 1632 and lateral struts 1634, 1636, 1638, 1639. The inner wall 1604 may comprise longitudinal struts 1630 along the inner lumen 1602 of the stent structure 1600, the longitu-dinal struts 1630 comprising a linear configuration, so the longitudinal struts 1630 are generally parallel to one another in both their expanded and contracted configurations. Because of this arrangement, the inner lumen 1602 does not exhibit any foreshortening when changing from the con-tracted to the expanded configuration. This may reduce or eliminate any axial stretching of the valve structure attached to the inner lumen. This may also permit the inner lumen 1602 to be predictably positioned and deployed while reduc-ing the risk of inadvertent position shifting.

The outer wall 1606 may comprise longitudinal struts 1632 that extend from the first closed end 1612 to the second open end 1614 of the outer wall 1606.

The transition wall 1608 of the stent structure 1600 transitions from the longitudinal struts 1630 of the inner wall 1604 to the longitudinal struts 1632 of the outer wall 1606. The transition wall 1608 may curve back on itself from the longitudinal struts 1630 of the inner wall 1604 to the longitudinal struts 1632 of the outer wall 1606 as illustrated in FIG. 16B.

As noted previously, in some embodiments, the outer wall 1606 of the stent structure 1600 comprises a non-cylindrical shape when in the expanded configuration. The outer wall 1606 may comprise a first end region 1640 that is contiguous with the transition wall 1608, comprising an external convex shape, and a second end region 1642 that forms the outer opening 1626. The shape and curvature of the outer wall 1606 may be similar or fall within the parameters discussed in regard to the stent structure 100 as discussed and illus-trated in regard to FIG. 1G. For example, the outer wall 1606 may comprise a first end region 1640 that is contiguous with the transition wall 1608. The outer wall 1606 may comprise a plurality of longitudinal struts 1632 with each longitudinal strut comprising a compound curve. In the illustrated embodiment of FIG. 16B, each longitudinal strut 1630 transitions from a concave curve at the first closed end 1612, to a convex curve, to a concave curve at the second open end 1614. Each curve may have a different radius of curvature to create the compound curve of the outer wall 1606. In some variations, the stent frame geometry may be characterized by the relative curvatures of the longitudinal struts. The greatest curvature may be concave curve $R_6$ (relative to the annular cavity 1610) adjacent to the outer junction 1624, which is greater than convex curve $R_7$ at the mid region 1641, which in turn is greater than concave curve $R_8$ located in the region of first end region 1640 of the outer wall 1606, followed by concave curve $R_9$ at the inner junction 1622, and then followed by concave curvature $R_{10}$ of the second end region 1642 and then the slight concave curvature $R_{11}$ of the transition wall 1608.

While the non-cylindrical configuration of the outer wall 1606 may exhibit some foreshortening as the outer wall 1606 transitions from a relatively straight orientation in the contracted configuration to the hourglass shape or concave/ convex/concave contour in its expanded configuration, the foreshortening effect may not be uniform or symmetrical and thus alter the relative position of some features of the outer wall 1606. This may be mitigated by adjusting the angular orientation of the transition wall 1608, which can then displace the outer wall 1606 toward or away from the inlet opening 1616 of the stent structure 1600 and offset some of the other longitudinal displacement of the outer wall 1606 that results from the foreshortening. This allows, for example, the reduced diameter middle section of the outer wall 1606 to generally maintain the same relative longitudinal location with respect to the overall length of the stent or to the valve location within the stent, before and after expansion. This in turn may help to maintain the expected implant location during delivery.

The lateral struts 1634 of the inner wall 1604 may be characterized by a contiguous set of lateral struts that form a partial or complete circumferential or perimeter strut around the inner wall 1604 of the stent structure 1600. The lateral struts 1634, however, can vary in more than just their circumferential orientation. To facilitate the expansion and contraction of the overall stent structure, one or more of the lateral struts, or all of the struts, may comprise a pair of angled legs 1634a, 1634b, where each lateral end of each angled leg is contiguous or integrally formed with the longitudinal strut 1630 and where each angled leg is joined together at a central taper 1634c. The pair of angled legs 1634a, 1634b may be angled toward the first closed end 1612 or toward the second open end 1614. The structure of the pair of angled legs 1634a, 1634b may be similar to the lateral struts discussed above in relation to FIGS. 4A-4C.

The lateral struts 1636 of the outer wall 1606 in the second end region 1642 may also be characterized by a contiguous set of lateral struts that form a partial or complete circumferential or perimeter strut around the outer wall 1606 of the stent structure 1600. The lateral struts 1636, however, can vary in more than just their circumferential orientation. To facilitate the expansion and contraction of the overall stent structure, one or more of the lateral struts, or all of the struts, may comprise a pair of angled legs 1636a, 1636b, where each lateral end of each angled leg is contiguous or integrally formed with a longitudinal strut 1632 and where each angled leg is joined together at a central taper 1636c. While the bend configuration of the formed by the two angled legs may comprise a simple bend, in other examples, each leg 1636a, 1636b may extend centrally to form a hairpin bend region 1636d. The structure of the pair of angled legs 1636a, 1636b may be similar to the lateral struts discussed above in relation to FIGS. 4A-4C.

In the illustrated embodiment, lateral struts 1638 in a mid region 1641 may project radially outward relative to the outer wall 1606. For example, in the mid region 1641 of the outer wall 1606, the pair of angled legs 1638a, 1638b project radially outward and are configured to act as a barb or anchor. As illustrated in FIGS. 16A and 16B, the orientation of the legs 1638a, 1638b and middle bends 1638c of one or more set of circumferential struts 1638 may also deviate radially outward relative to the adjacent longitudinal struts 1632 to provide barb-like or force concentration structures to resist displacement of the strut structure relative to the native valve tissue.

In the illustrated embodiment, lateral struts 1639 in the first end region 1640 may project radially outward relative to the outer wall 1606. For example, in the first end region 1640 of the outer wall 1606, the pair of angled legs 1639a, 1639b project radially outward and are configured to act as a barb or anchor. As illustrated in FIGS. 16A and 16B, the orientation of the legs 1639a, 1639b and middle bends 1639c of one or more set of circumferential struts 1639 may also deviate radially outward relative to the adjacent longitudinal struts 1632 to provide barb-like or force concentration structures to resist displacement of the strut structure relative to the native valve tissue.

As depicted in 16A, the stent structure 1600 may further comprise a plurality of longitudinal barbs 1654 that may be optionally adapted for any of the stent frame embodiments described herein. The barb 1654 is located within an elongate cavity or opening 1656 of the longitudinal strut 1632. Structural details of the barb 1654 may be similar to the longitudinal barb 1114 discussed in relation to FIGS. 11A-11B. The exemplary embodiments depicted in FIGS. 16A and 16B are located at an end of a longitudinal strut 1632, at a junction between two lateral struts 1636, but in other variations the barb 1654 may be located along the longitudinal strut 1632 at junction spaced away from the end of the longitudinal strut 1632, or at a location spaced away from a junction where the lateral struts 1636 are located.

Figure 17A:
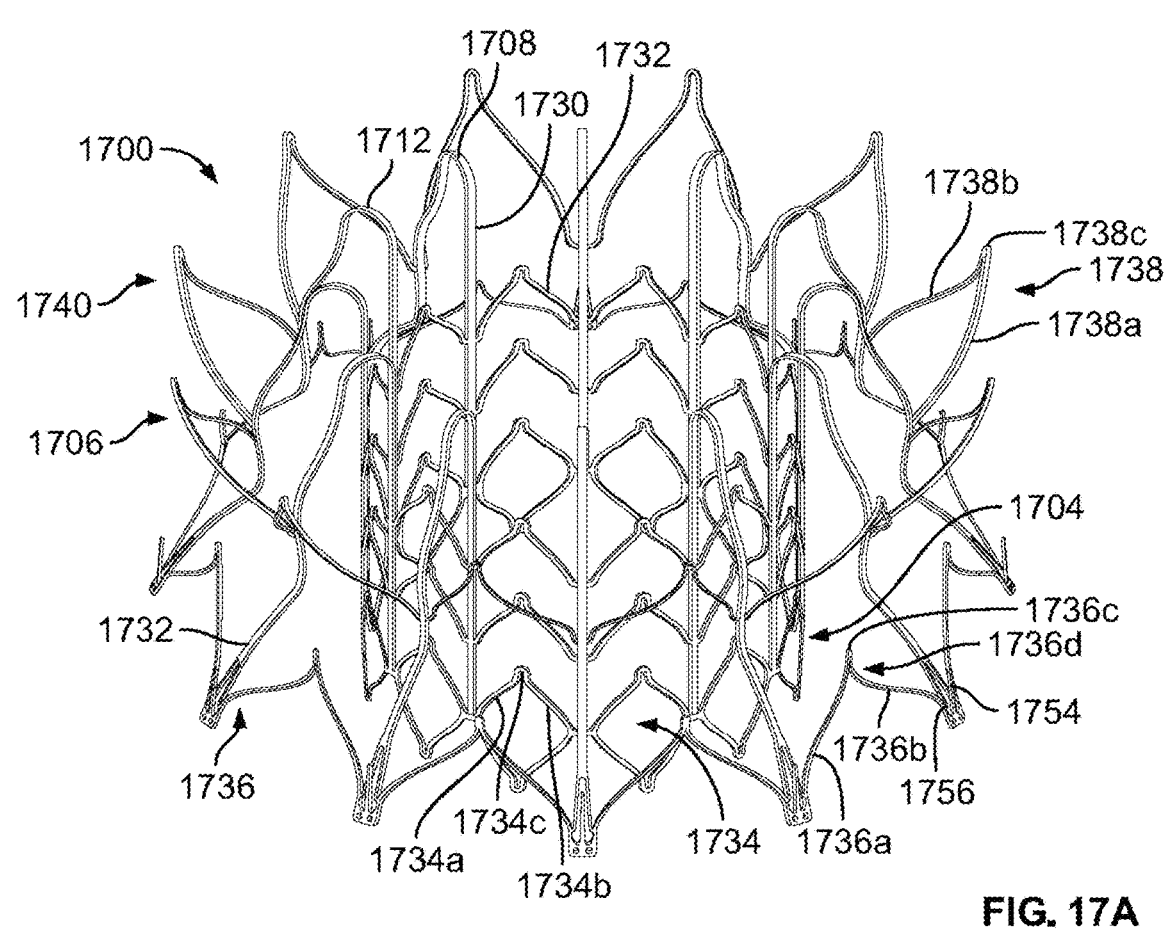
FIG. 17A depicts a schematic perspective view of a stent structure of a replacement valve, according to one embodiment of the present disclosure.
Figure 17B:
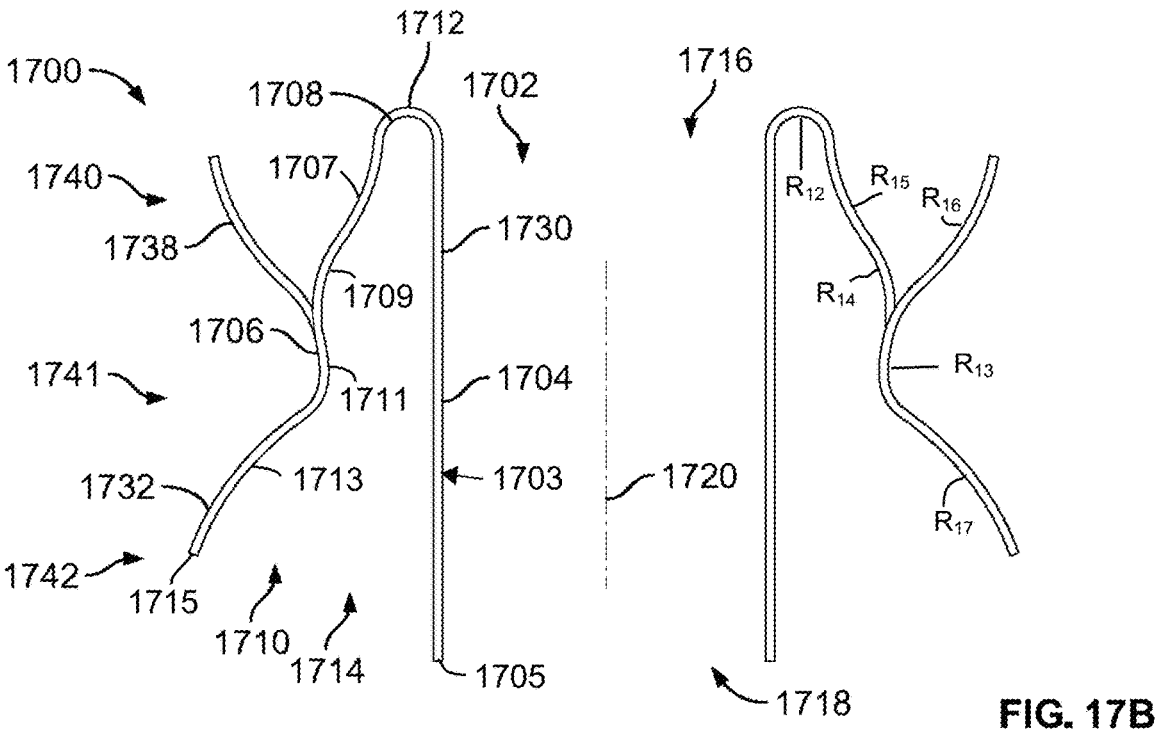
FIG. 17B depicts a cross-sectional view of the stent structure of FIG. 17A.

FIGS. 17A and 17B illustrate an exemplary embodiment of a stent structure or frame 1700 in an expanded configuration. While not illustrated, the stent structure 1700 may be collapsed into a collapsed configuration. In some embodiments, the stent structure 1700 may self-expand when not constrained. FIG. 17A illustrates a perspective view of the stent structure 1700 and FIG. 17B illustrates a cross-sectional view of the stent structure 1700. The stent structure 1700 may have similar features as the stent structure 1600 and may not be repeated hereafter.

The stent structure 1700 comprises an inner lumen 1702 formed by an inner wall 1704. An outer wall 1706 is spaced radially apart from the inner wall 1704 via a transition wall 1708, and forms an annular cavity 1710. The transition wall 1708 may result from the folding, inversion, or eversion of a single tubular structure into a double-wall unibody tubular stent frame or structure. The stent structure 1700 has first closed end 1712 that is located at the transition wall 1708, and a second open end 1714 of the outer wall 1706, wherein the annular cavity 1710 is open and accessible.

The inner lumen 1702 comprises a first opening 1716 surrounded by the transition wall 1708 and a second opening 1718 at the second open end 1714 of the stent structure 1700. In the illustrated embodiment, a longitudinal axis 1720 of the inner lumen 1702 is coincident with a central axis of the stent structure 1700. In some embodiments, the inner lumen 1702 may be eccentrically located relative to the outer wall 1706 of the stent structure 1700. The inner lumen 1702 typically comprises a circular cross-sectional shape with a generally cylindrical shape between the first opening 1716 and second opening 1718, as depicted in FIGS. 17A and 17B. In other examples, the inner lumen 1702 may comprise a frustoconical, oval or polygonal shape. In some variations, the stent structure may comprise an inner lumen where the size and/or shape of the first and second openings may be different. In embodiments where the inner lumen comprises a non-cylindrical shape, some foreshortening of the inner wall may occur.

The stent structure 1700 comprises a plurality of integrally formed stent struts, such as longitudinal struts 1730, 1732 and lateral struts 1734, 1736. The inner wall 1704 may comprise longitudinal struts 1730 along the inner lumen 1702 of the stent structure 1700 which have a linear configuration, so the longitudinal struts 1730 are generally parallel to one another in both their expanded and contracted configurations. Because of this arrangement, the inner lumen 1702 does not exhibit any foreshortening when changing from the contracted to the expanded configuration. This may reduce or eliminate any axial stretching of the valve structure attached to the inner lumen. This may also permit the inner lumen 1702 to be predictably positioned and deployed while reducing the risk of inadvertent position shifting.

The outer wall 1706 may comprise longitudinal struts 1732 that extend from the first closed end 1712 to the second open end 1714 of the outer wall 1706.

The transition wall 1708 of the stent structures 1700 transitions from the longitudinal struts 1730 of the inner wall 1704 to the longitudinal struts 1732 of the outer wall 1706. The transition wall 1708 may curve back on itself from the longitudinal struts 1730 of the inner wall 1704 to the longitudinal struts 1732 of the outer wall 1706. In some embodiment, the transition wall 1708 curves back around 180 degrees as illustrated in FIG. 17B.

The outer wall 1706 of the stent structure 1700 comprises a non-cylindrical shape when in the expanded configuration. The outer wall 1706 of the stent structure 1700 may comprise a first end region 1740, a mid portion 1741, and a second end portion 1742. The first end region 1740 of the outer wall 1706 may be contiguous with the transition wall 1708. The outer wall 1706 may comprise a longitudinal strut 1730 that comprises a compound curve. In the illustrated embodiment of FIG. 17B, the longitudinal strut 1730 comprises a straight section 1703 with a free straight inner end 1705 along the inner wall 1704, which transitions to a concave curve (relative to the annular cavity 1710 formed between the inner wall 1704 and outer wall 1706) at the first closed end 1712, to a convex curve 1707, to a concave curve 1709, to a convex curve 1711, and to a concave curve 1713 and ending with a free curved outer end 1715 about the second open end 1714 of the implant 1700. Each of these segments of the longitudinal strut 1730 lie in the same radial plane, and each curve may have a different radius of curvature to create the compound curve of the outer wall 1706. Referring to FIG. 17A, in addition, the first end region 1740 and the second end portion 1742 of the outer wall 1706 also includes lateral struts 1736, 1738, respectively, with the lateral struts 1736 of the second end region 1742 comprising a generally convex curve profile shape (relative to the annular cavity 1710), while the lateral struts 1738 of the first end region 1740 comprising a generally convex shape (relative to the annular cavity 1710). In some variations, the relative degree of curvature is greatest at the concave curve of the first closed end 1712 ($R_{12}$), followed by the convex curve 1711 ($R_{13}$) of the mid-section 1741, which in turn is greater than the curvatures of the concave curvature 1709 ($R_{14}$) of the first end region 1740, which is greater than the slight curvatures provided in the convex curve 1707 ($R_{15}$) of the first end portion 1740, the concave curve ($R_{16}$) of lateral struts 1738, the convex curve of the lateral struts 1736, or the concave curve 1713 ($R_{17}$) of the second end portion 1742 of the outer wall 1706.

While the non-cylindrical configuration of the outer wall 1706 may exhibit some foreshortening as the outer wall 1706, transitions from a relatively straight orientation in the contracted configuration to the hourglass shape or concave/convex/concave/convex/concave contour in its expanded configuration, the foreshortening effect may not be uniform or symmetrical, and thus may alter the relative position of some features of the outer wall 1706. This may be mitigated by adjusting the angular orientation of the transition wall 1708, which can displace the outer wall 1706 toward or away from the inlet opening 1716 of the stent structure 1700 and offset some of the longitudinal displacement of the outer wall 1706 that results from the foreshortening. This allows, for example, the reduced diameter middle section of the outer wall 1706 to generally maintain its relative longitudinal location with the stent, before and after expansion. This in turn may help to maintain the expected implant location during delivery.

The lateral struts 1734 of the inner wall 1704 may be characterized by a contiguous set of lateral struts that form a partial or complete circumferential or perimeter strut around the inner wall 1704 of the stent structure 1700. The lateral struts 1734, however, can vary in more than just their circumferential orientation. To facilitate the expansion and contraction of the overall stent structure, one or more of the lateral struts, or all of the struts, may comprise a pair of angled legs 1734a, 1734b, where each lateral end of each angled leg is contiguous or integrally formed with the longitudinal struts 1730 and where each angled leg is joined together at a central taper 1734c. The pair of angled legs 1734a, 1734b may be angled toward the first closed end 1712 of toward the second open end 1714. The structure of the pair of angled legs 1734a, 1734b may be similar to the lateral struts discussed above in relation to FIGS. 4A-4C.

The lateral struts 1736 of the outer wall 1706 may also be characterized by a contiguous set of lateral struts that form a partial or complete circumferential or perimeter strut around the outer wall 1706 of the stent structure 1700. The lateral struts 1736, however, can vary in more than just their circumferential orientation. To facilitate the expansion and contraction of the overall stent structure 1700, one or more of the lateral struts 1736, or all of the struts, may comprise a pair of angled legs 1736a, 1736b, where each lateral end of each angled leg 1736a, 1736b is contiguous or integrally formed with a longitudinal strut 1732 and where each angled leg 1736a, 1736b is joined together at a central taper 1736c. While the bend configuration of the formed by the two angled legs 1736a, 1736b may comprise a simple bend, in other examples, each leg 1736a, 1736b may extend centrally to form a hairpin bend region 1736d. The structure of the pair of angled legs 1736a, 1736b may be similar to the lateral struts discussed above in relation to FIGS. 4A-4C.

In the illustrated embodiment, lateral struts 1738 in the first end region 1740 may project radially outward relative to the outer wall 1706 to form a plurality of lateral projections. The plurality of lateral projections may extend circumferentially around the outer wall of the stent structure 1700. For example, in a first end region 1740 of the outer wall 1706, a pair of angled legs 1738a, 1738b that connect at a middle bend 1738c at an apex project radially outward and are configured to act as a barb or anchor. As illustrated in FIG. 17B, the orientation of the angled legs 1738a, 1738b and middle bends 1738c of one or more set of circumferential struts 1738 may also deviate radially outward relative to the adjacent longitudinal struts 1732 to provide barb-like or force concentration structures to resist displacement of the strut structure relative to the native valve tissue. The pair of angled legs 1738*a*, 1738*b* comprises a compound curve with an inflection point that transitions each of the angled legs 1738*a*, 1738*b* from a concave curve where the pair of angled legs 1738*a*, 1738*b* couples to the longitudinal strut 1732 to the convex curve.

As depicted in 17A, the stent structure 1700 may further comprise a plurality of longitudinal barbs 1754 that may be optionally adapted for any of the stent frame embodiments described herein. The barb 1754 is located within an elongate cavity or opening 1756 of the longitudinal strut 1732. Structural details of the barb 1754 may be similar to the longitudinal barb 1114 discussed in relation to FIGS. 11A-11B. The exemplary embodiments depicted in FIGS. 17A and 17B are located at an end of a longitudinal strut 1732, at a junction between two lateral struts 1736, but in other variations the barb 1754 may be located along the longitudinal strut 1732 at junction spaced away from the end of the longitudinal strut 1732, or at a location spaced away from a junction where the lateral struts 1736 are located.

Figure 18A:
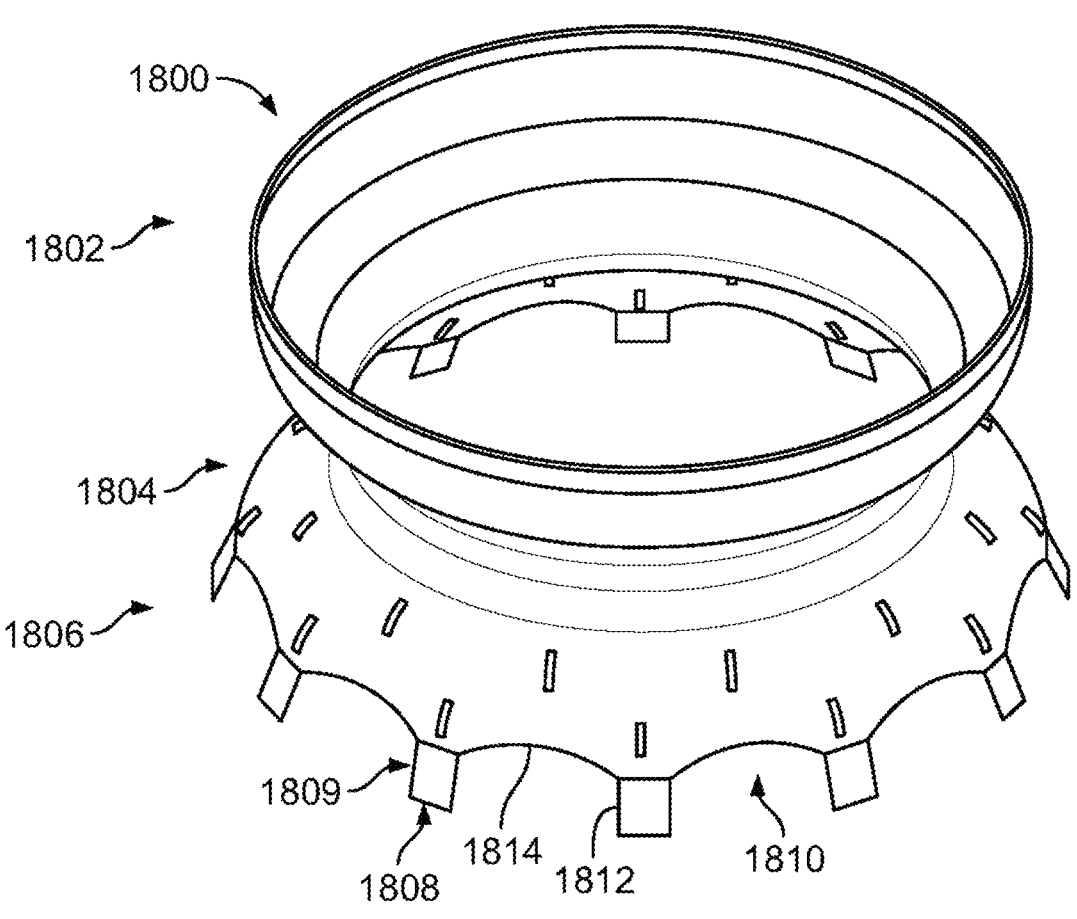
FIG. 18A depicts a perspective view of a skirt of a replacement valve according to one embodiment of the present disclosure.
Figure 18B:
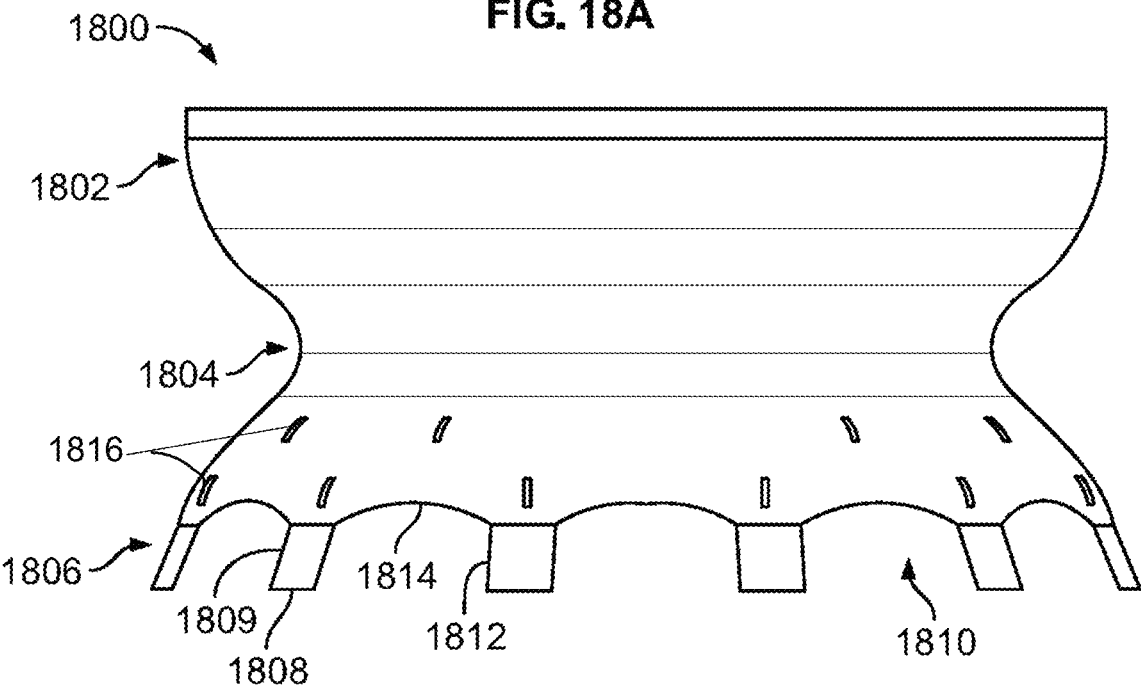
FIG. 18B depicts a side view of the skirt of FIG. 18A.

FIGS. 18A-18B illustrate a skirt 1800 for a stent structure. FIG. 18A illustrates a perspective view of the skirt 1800. FIG. 18B illustrates a side view of the skirt 1800. In some embodiments, the skirt 1800 is configured to conform to the shape of the stent structure and/or is pre-shaped with an hourglass shape to facilitate conforming the skirt 1800 to the stent structure, e.g., stent 1120, 1600 and 1700 in FIGS. 11C and 16A-17B. The skirt 1800 is configured to be secured to an outer wall of the stent structure and therefore the skirt may have a similar shape as the outer wall of the stent structure. The skirt 1800 comprises an upper portion 1802, a central portion 1804, and a lower portion 1806. The upper portion 1802 comprises a first diameter, the central portion 1804 comprises a second diameter, and the lower portion 1806 comprises a third diameter. The first diameter and the third diameter are greater than the second diameter and the first diameter may be is similar to the third diameter. Accordingly, the skirt 1800 comprises an hourglass type shape.

The lower portion 1806 of the skirt 1800 comprises a plurality of cutouts 1810 that are disposed along a lower edge 1808 of the skirt 1800. The plurality of cutouts 1810 are disposed between extensions 1809 such that the lower edge 1808 alternates between the extensions 1809 and the cutouts 1810. In some embodiments, the extensions 1809 may align with longitudinal struts of the strut structure, similar to the longitudinal struts 1630, 1730 of the stent structures 1600, 1700 discussed above in relation to FIGS. 16A-17B. The extensions 1809 may provide additional suturing or attachment surface area of the skirt 1800 to the longitudinal struts, and may comprise an elongate shape, e.g., rectangle or tab-like shape. Preformed apertures or slots 1816 may also be provided for any tissue engagement barbs provided on the stent structure, such as the barbs depicted in FIGS. 11A to 11C. Due to the longitudinal orientation of the barbs, the apertures or slots may have a vertical or longitudinal orientation or shape.

The plurality of cutouts 1810 may comprise vertical edges 1812 connected by a concave curve 1814. The concave curve 1824 may follow the lateral struts of the outer wall of the stent structure, similar to the lateral struts 1634, 1734 of the stent structures 1600, 1700 discussed above in relation to FIGS. 16A-17B. Among other benefits, the plurality of cutouts 1810 of the skirt 1800 improve volumetric efficiency of a replacement valve and can lower sheathing loads. The exemplary skirt/cover 1800 in FIGS. 18A and 18B may be adapted for use with the stent structures 100, 150, 1600, 1700

FIG. 19A-19C illustrate a replacement valve 1900 comprising a stent frame 1910 and a valve assembly 1920. FIG. 19A illustrates a perspective view of the replacement valve 1900 with the valve assembly 1920 attached to the stent frame 1910. The valve assembly 1920 comprises a plurality of leaflets 1922*a-c* that are located in an inner lumen 1912 of the stent frame 1910. The illustrated embodiment includes three leaflets 1922*a-c*, however, the present disclosure is not limited. The valve assembly 1922 may comprise more or fewer than three leaflets 1922*a-c*. The plurality of leaflets 1922*a-c* may be formed from an artificial or animal-derived material. The valve assembly 1920 further comprises valve commissures 1924*a-c* where the leaflets 1922*a-c* abut in the inner lumen 1912 of the stent frame 1910. The replacement valve 1900 may further comprise an inner skirt liner 1930 and an outer skirt liner (not shown). The outer skirt liner may be similar to the skirt 1800 described in relation to FIGS. 18A-18B.

The valve assembly 1920 may be attached to the stent frame 1910 with a plurality of brackets 1940. The number of brackets 1940 may correspond with the number of leaflets 1922*a-c* of the valve assembly 1920. In the illustrated embodiment of FIG. 19A, the replacement valve 1900 includes three brackets 1940 that corresponds with the three leaflets 1922*a-c* of the valve assembly 1920.

FIG. 19B illustrates a perspective detailed view of the replacement valve 1900 with the valve assembly 1920 attached to the stent frame 1910 with a bracket 1940 with one of the brackets 1940 attaching the first leaflet 1922*a* and the second leaflet 1922*b* to the bracket 1940 and the stent frame 1910. In the illustrated embodiment, the bracket 1940 comprises a U-shape with a first arm 1942 and a second arm 1944 with a connection 1946 attaching the first arm 1942 and the second arm 1944. The bracket 1940 further comprises an opening 1943 between the first arm 1942 and the second arm 1944. The bracket 1940 further comprises a plurality of apertures 1948 on the first arm 1942 and on the second arm 1944. The stent frame 1910 further comprises a plurality of apertures 1914 disposed along a longitudinal strut 1916.

The leaflets 1922*a-b* and the commissure 1924*a* extend through the opening 1943 of the bracket 1940 on an inner surface of the bracket 1940. The leaflet 1922*a* wraps around the bracket 1940 onto an outer surface of the first arm 1942 and the leaflet 1922*b* wraps around the bracket 1940 onto an outer surface of the second arm 1944. A suture 1949 may be used to couple the leaflets 1922*a-b* and the commissure 1924*a* to the stent frame 1910. The suture 1949 extends though the apertures 1914 of the stent frame 1910, the apertures 1948 of the first arm 1942 and the second arm 1944, and the leaflets 1922*a-b*. In the illustrated embodiment, two adjacent sutures 1949 are used to illustrate the routing paths indicated by the arrows (two arrows per each suture 1949) in FIG. 19B. Each suture 1949 passes through an aperture 1914 of a longitudinal strut 1916 (lowest arrow) toward the valve assembly 1920, passing into one of the everted commissure flap 1922*d* of leaflet 1922*b* and into an aperture 1948 of a first arm 1944 of the bracket 1940, into the gap or opening 1943 between the arms 1942, 1944 of the bracket 1940, and through the apposed leaflets 1922*a*, 1922*b* residing in the opening 1943, and out through the opening 1948 on the other arm 1942 of the bracket 1940, and out through the everted flap 1922*c* of the other leaflet 1922*a*, as depicted in FIG. 19C. The suture 1949 is then looped back through the same aperture 1914 of the longitudinal strut 1916, and then routed to the next adjacent aperture 1914 of the strut 1916, and routing again through the everted flaps of the leaflets 1922a, 1922b, bracket apertures 1948 and apposed leaflets 1922a, 199b, and then back through the adjacent aperture 1914 (second lowest arrow). The other suture 1949 takes a similar routing through the next two adjacent going the apposed leaflets 1922a, 1922 through the two internal layers of the leaflets 1922a, 1922b between the arms 1942, 1944 of the bracket 1940, and through the apposed leaflets 1922a, 1922b residing in the opening 1943, and out through the opening 1948 on the other arm 1942 of the bracket 1940, and out through the everted flap 1922c of the other leaflet 1922a.

FIG. 19C illustrates a cross-sectional view of the leaflets 1922a-b and the commissure 1924a coupled to the bracket 1940 by the sutures 1949. For case of illustration, the stent frame 1910 is not shown in FIG. 19C. The suture 1949 extends through the one layer of the leaflet 1922a, then through an aperture 1948 of the first arm 1942, then through another layer of the leaflet 1922a, then though a layer of the leaflet 1922b, then through an aperture 1948 of the second arm 1944, and then through another layer of the leaflet 1922b.

FIGS. 20A and 20B illustrate a replacement valve 2000 comprising a stent frame 2010 and a valve assembly 2020 comprising another embodiment of attaching leaflets to a bracket 2040. The replacement valve 2000 may comprise all of the structural components discussed in relation to the replacement valve 1900 of FIG. 19A.

FIG. 20A illustrates a perspective detailed view of the replacement valve 2000 with the valve assembly 2020 attached to the stent frame 2010 with the bracket 2040. The bracket 2040 attaches a first leaflet 2022a and a second leaflet 2022b to the bracket 2040 and the stent frame 2010. The bracket 2040 is similar to the bracket 1940 of FIGS. 19A-19C. The bracket 2040 comprises a U-shape with a first arm 2042 and a second arm 2044 with a connection 2046 attaching the first arm 2042 and the second arm 2044. The bracket 2040 further comprising an opening 2043 between the first arm 2042 and the second arm 2044. The bracket 2040 further comprises a plurality of apertures 2048 on the first arm 2042 and on the second arm 2044. The stent frame 2010 further comprises a plurality of apertures 2014 disposed along a longitudinal strut 2016.

The leaflets 2022a-b and a commissure 2024a all extend through the opening 2043 of the bracket 2040 and then the leaflets 2022a-b turn back and form two layers of each leaflets 2022a-b and engage an inner surface of the first arm 2042 and the second arm 2044 of the bracket 2040, respectively. The leaflet 2022a wraps around the bracket 2040 onto an outer surface of the first arm 2042 and the leaflet 2022b wraps around the bracket 2040 onto an outer surface of the second arm 2044. A suture 2049 may be used to couple the leaflets 2022a-b and the commissure 2024a to the stent frame 2010. The suture 2049 extends though the apertures 2014 of the stent frame 2010, the apertures 2048 of the first arm 2042 and the second arm 2044 and the leaflets 2022a-b. In the illustrated embodiment, two sutures 2049 may be used and they may follow the path indicated by the arrows in FIG. 20A.

FIG. 20B illustrates a cross-sectional view of the leaflets 2022a-b and the commissure 2024a coupled to the bracket 2040 by the sutures 2049. For case of illustration, the stent frame 2010 is not shown in FIG. 20B. The suture 2049 extends through the one layer of the leaflet 2022a, then through an aperture 2048 of the first arm 2042, then through two layers of the leaflet 2022a within the opening 2043, then though two layers of the leaflet 2022b within the opening

2143, then through an aperture 2048 of the second arm 2044, and then through another layer of the leaflet 2022b.

FIGS. 21A and 21B illustrate a replacement valve 2100 comprising a stent frame 2110 and a valve assembly 2120 comprising another embodiment of attaching leaflets to a bracket 2140. The replacement valve 2100 may comprise all of the structural components discussed in relation to the replacement valve 1900 of FIG. 19.

FIG. 21A illustrates a perspective detailed view of the replacement valve 2100 with the valve assembly 2120 attached to the stent frame 2110 with the bracket 2140. The bracket 2140 attaches a first leaflet 2122a and a second leaflet 2122b to the bracket 2140 and the stent frame 2110. The bracket 2140 is similar to the bracket 1940 of FIGS. 19A-19C. The bracket 2140 comprises a U-shape with a first arm 2142 and a second arm 2144 with a connection 2146 attaching the first arm 2142 and the second arm 2144. The bracket 2140 further comprising an opening 2143 between the first arm 2142 and the second arm 2144. The bracket 2140 further comprises a plurality of apertures 2148 on the first arm 2142 and on the second arm 2144. The stent frame 2110 further comprises a plurality of apertures 2114 disposed along a longitudinal strut 2116.

The leaflets 2122a-b and a commissure 2124a all extend through the opening 2143 of the bracket 2140 on an inner surface of the bracket 2140. The leaflet 2122a wraps around the bracket 2140 onto an outer surface of the first arm 2142 and turns back to form two layers of the leaflet 2122a. The leaflet 2122b wraps around the bracket 2140 onto an outer surface of the second arm 2144 and turns back to form two layers of the leaflet 2122b. A suture 2149 may be used to couple the leaflets 2122a-b and the commissure 2124a to the stent frame 2110. The suture 2149 extends though the apertures 2114 of the stent frame 2110, the apertures 2148 of the first arm 2142 and the second arm 2144 and the leaflets 2122a-b. In the illustrated embodiment, two sutures 2149 may be used and they may follow the path indicated by the arrows in FIG. 21B.

FIG. 21B illustrates a cross-sectional view of the leaflets 2122a-b and the commissure 2124a coupled to the bracket 2140 by the sutures 2149. For case of illustration, the stent frame 2110 is not shown in FIG. 21B. The suture 2149 extends through the two layers of the leaflet 2122a, then through an aperture of the first arm 2142, then through another layer of the leaflet 2122a within the opening 2143, then though a layer of the leaflet 2122b within the opening 2143, then through an aperture of the second arm 2144, and then through two layers of the leaflet 2122b.

FIGS. 22A-22D illustrate a replacement valve 2200 that comprises a stent frame 2210, a valve assembly 2220, a skirt 2230, and a plurality of ring structures 2240 that are coupled to the stent frame 2210 to help collapse and expand the replacement valve 2200. A fist set 2250 of the plurality of ring structures 2240 are coupled to a first end region 2212 of the stent frame 2010. A second set 2260 of the plurality of ring structures 2240 may be coupled to a second end region 2214 of the stent frame 2210. A first suture 2202 may extend through a ring 2242 or loop of each of the rings 2242 of the first set 2250 of the plurality of ring structures 2240. A second suture 2204 may extend through the ring 2242 of each of the rings 2242 of the second set 2260 of the plurality of ring structures 2240. Tightening of the sutures 2202 and 2204 collapses and constrains the replacement valve 2200 and loosening of the sutures 2202 and 2204 allows the replacement valve 2200 to self-expand.

Figure 22A:
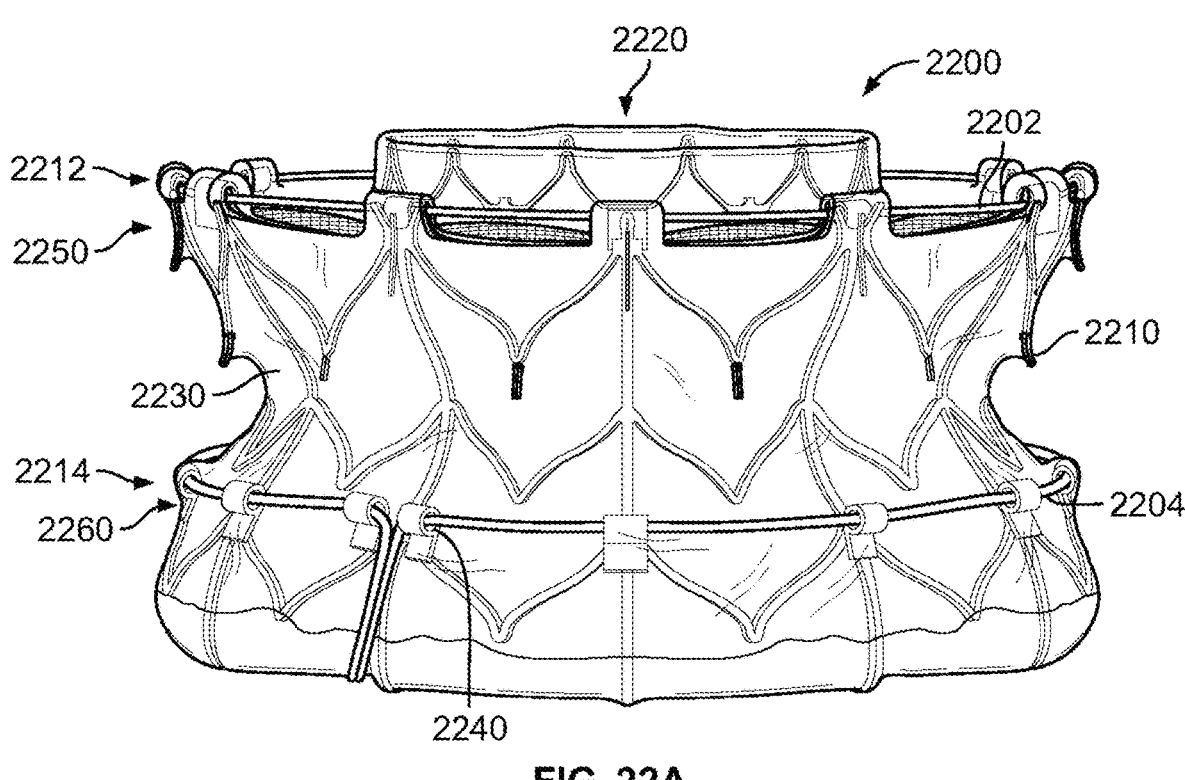
FIG. 22A depicts a perspective view of a replacement valve comprising a plurality of ring structures coupled to a stent structure of the replacement valve, according to one embodiment of the present disclosure.
Figure 22B:
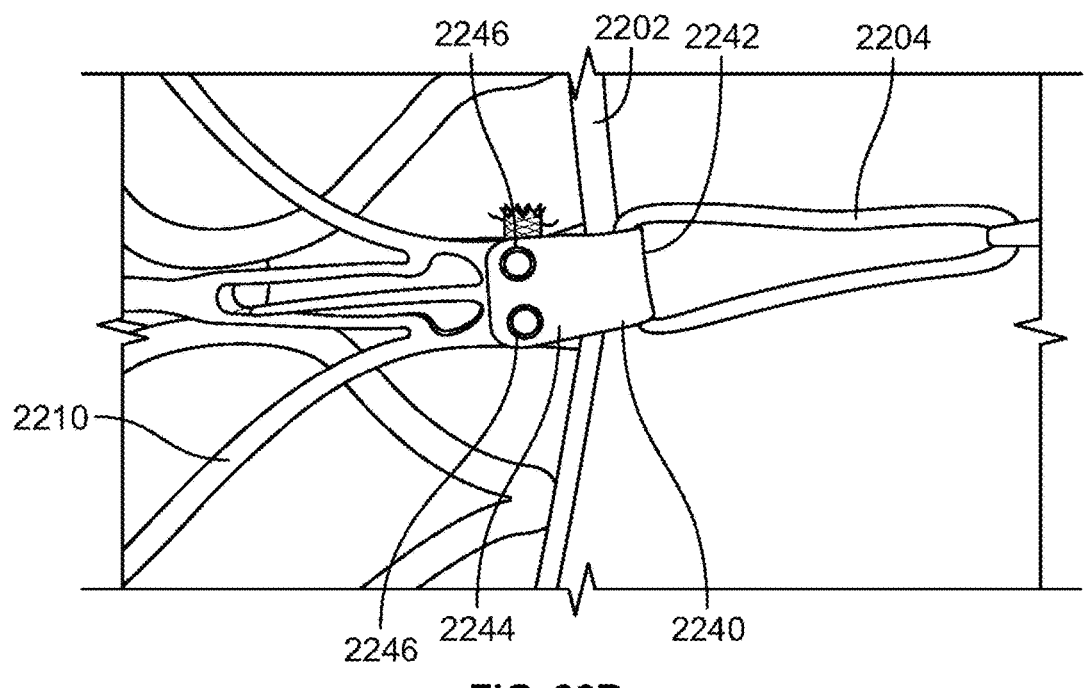
FIG. 22B depicts a detailed view of one of the ring structures of FIG. 22A.
Figure 22C:
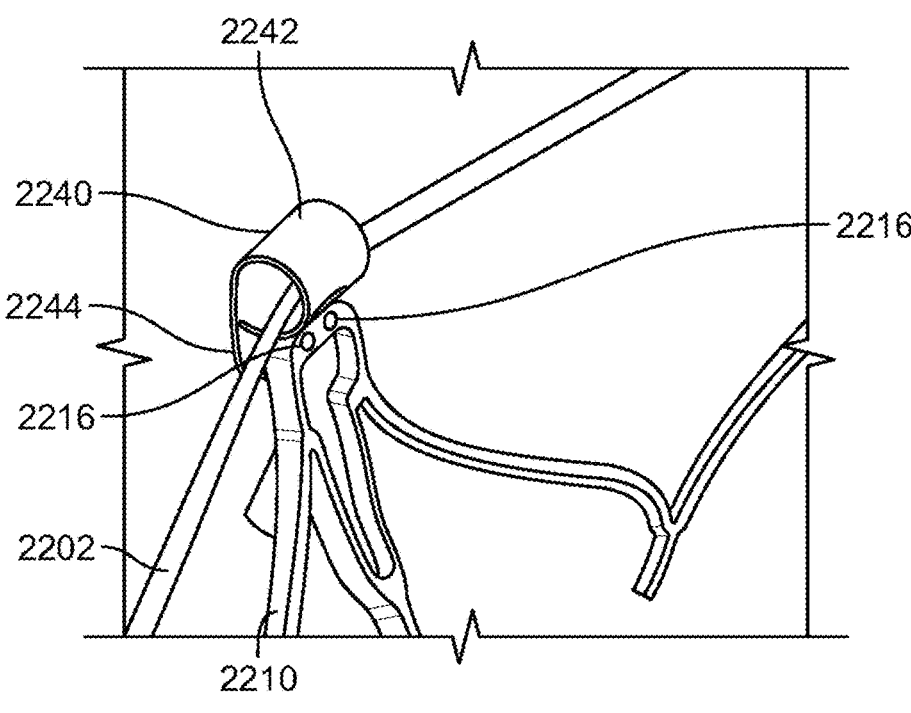
FIG. 22C depicts a detailed view of one of the ring structures of FIG. 22A.

FIGS. 22B and 22C illustrate detailed views of one of the plurality of ring structures 2240. In the illustrated embodiment, the ring structure 2240 includes the ring 2242 and a projection 2244 that is integral with the ring 2242. The ring 2242 is a circular loop that comprises an opening on each end. As discussed above, the ring 2242 is configured to receive a suture 2202 or 2204. As illustrated in FIG. 22B, the ring 2242 may receive more than one suture.

The projection 2244 of the ring structure 2240 comprises a pair of apertures 2246 that may be used to lash the ring structure 2240 to the stent frame 2210. As illustrated in FIG. 22C, the stent frame 2210 may comprise a pair of corresponding apertures 2216 for lashing the ring structure 2240 to the stent frame 2210.

Figure 22D:
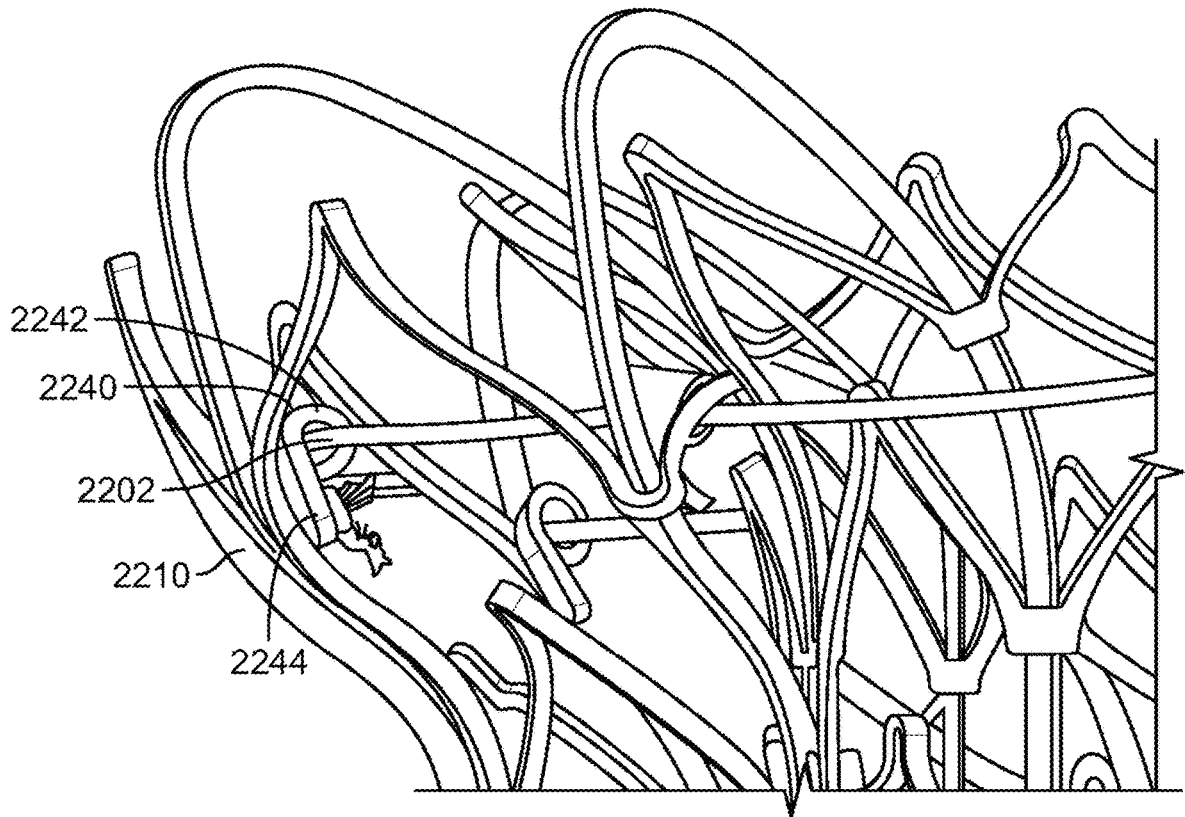
FIG. 22D depicts a detailed perspective view of a replacement valve comprising a plurality of ring structures coupled to an atrial side of a stent structure, according to one embodiment of the present disclosure.

In some embodiments, the plurality of ring structures 2240 may be coupled to an atrial side of the stent frame 2210 as illustrated in FIG. 22D. In other words, the plurality of ring structures 2240 are coupled to an inside of the stent frame 2210 rather than the outside of the stent frame 2210 as illustrated in FIG. 22A.

Figure 23A:
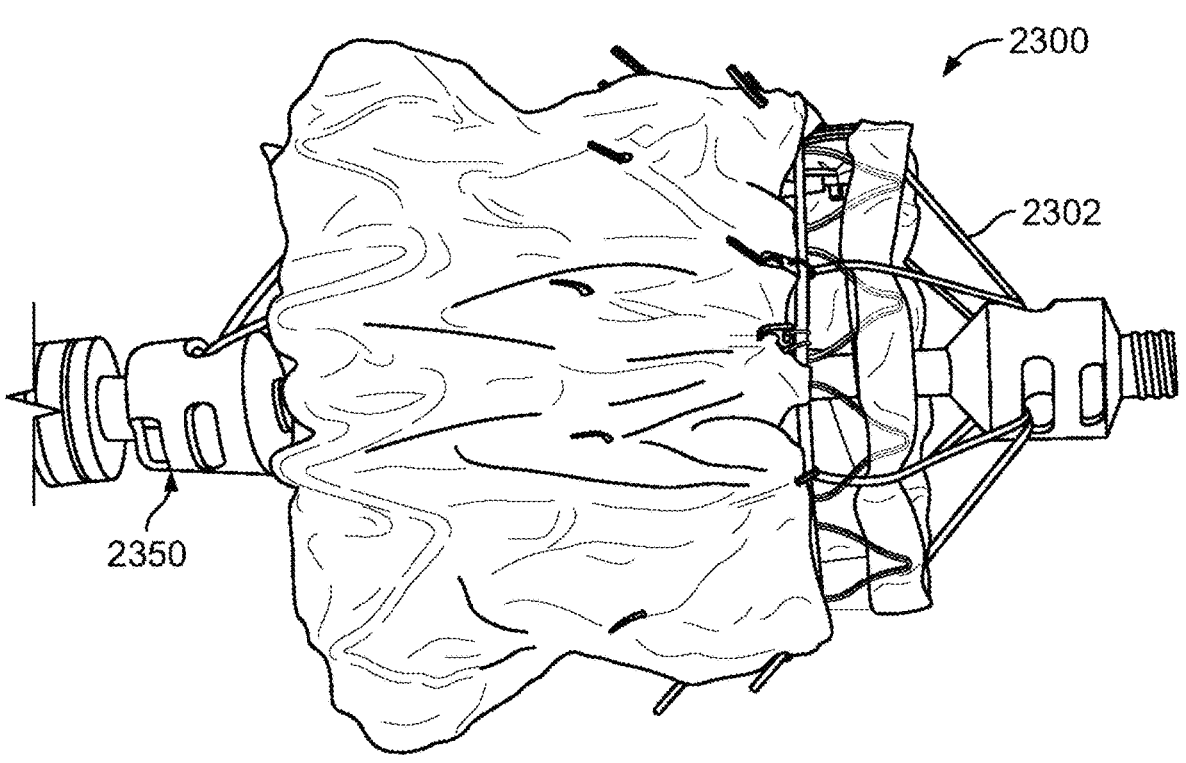
FIG. 23A depicts a perspective view of an implant retention/release assembly of a catheter delivery system that includes a rotor/stator assembly that is used to collapse a replacement valve.
Figure 23B:
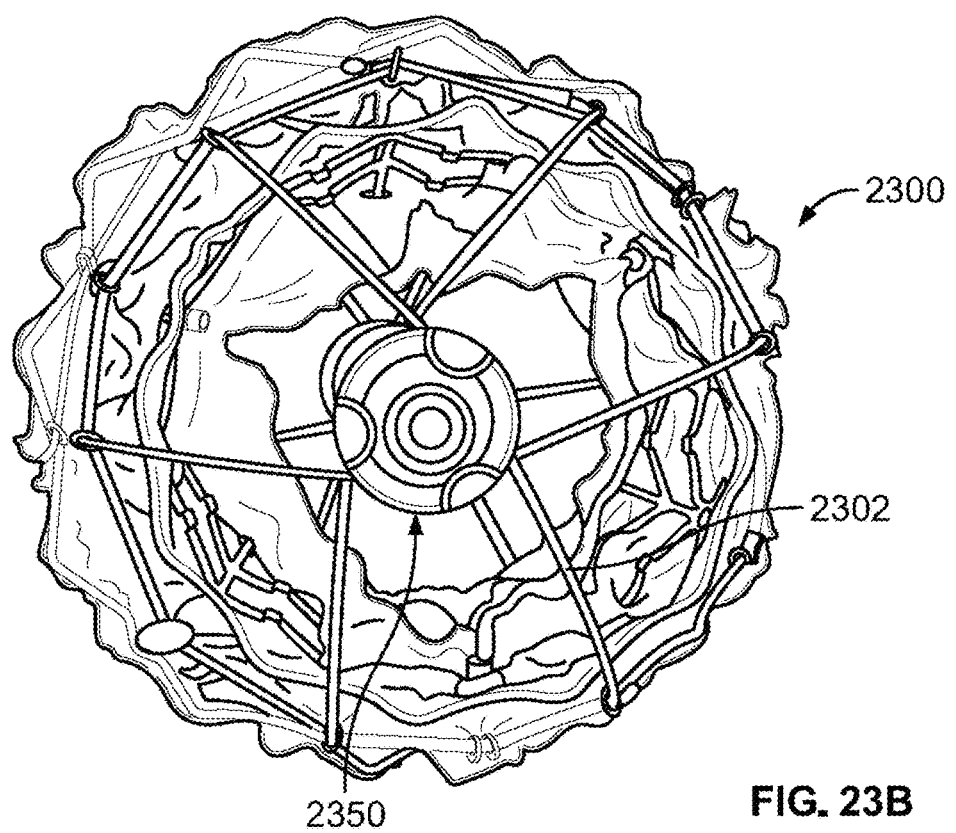
FIG. 23B depicts an end view of the implant retention/release assembly and the replacement valve of FIG. 23A.

FIGS. 23A and 23B illustrate a side view of an implant retention/release assembly 2350 of a catheter delivery system that includes a rotor/stator assembly that is used to maintain a replacement valve 2300 in a contracted or compressed configuration. A suture 2302 is used for routing the replacement valve 2300. Exemplary routing processes are disclosed in regard to FIGS. 24 and 25.

Figures 24, 25:
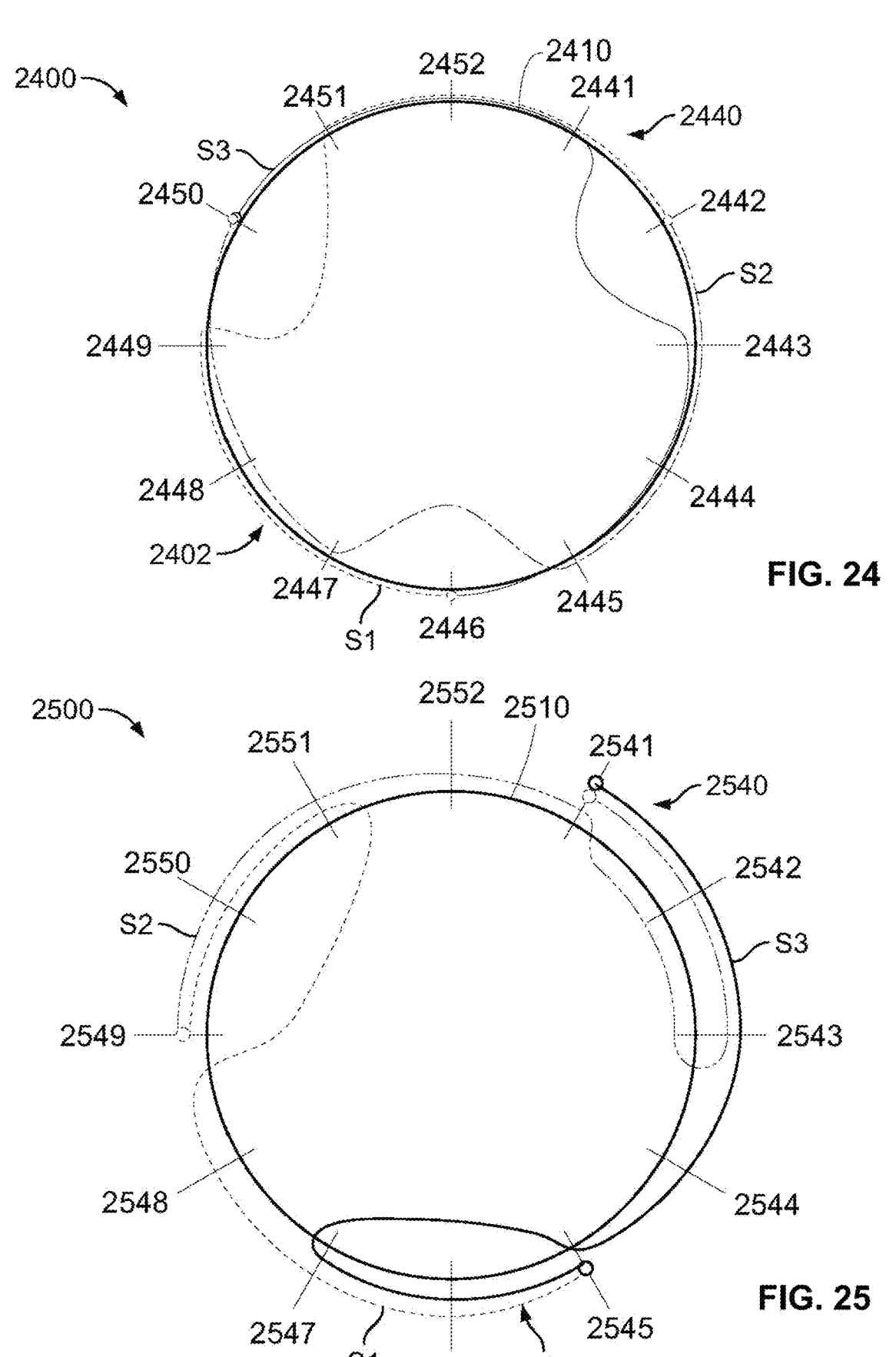
FIG. 24 depicts a schematic end view of a routing process pattern of a suture to collapse a replacement valve, according to one embodiment of the present disclosure.
FIG. 25 depicts a schematic end view of a routing process pattern of a suture to collapse a replacement valve, according to one embodiment of the present disclosure.

FIG. 24 illustrates a schematic end view of a routing process pattern of a suture 2402 to collapse a replacement valve 2400 and maintain the replacement valve 2400 in a collapsed configuration. The replacement valve 2400 may comprise a plurality of ring structures 2440 that may be similar to the ring structures 2240 discussed in relation to FIG. 22A-22D. In the illustrated schematic, the replacement valve 2400 includes twelve ring structures 2240 that are equally spaced along a circumference of a stent frame 2410. The twelve ring structures are disposed at the twelve hour positions of an analog clock, and include a first ring 2441, a second ring 2442, a third ring 2443, a fourth ring 2444, a fifth ring 2445, a sixth ring 2446, a seventh ring 2447, an eighth ring 2448, a ninth ring 2449, a tenth ring 2450, an eleventh ring 2451, and a twelfth ring 2452.

The routing process pattern of FIG. 24 begins with a first segment S1 of the suture 2402 tied to the sixth ring 2446. In some embodiments, an excess portion of the suture 2402 may be left behind and used in the routing process. In some embodiments, the excess portion of the suture 2402 may be six inches. The first segment S1 of the suture 2402 is threaded clockwise through the seventh ring 2447, the eighth ring 2448, the ninth ring 2449, skips the tenth ring 2450, threaded through the eleventh ring 2451, the twelfth ring 2452, the first ring 2441, and a knot is tied at the second ring 2442.

The routing process continues with a second segment S2 of the suture 2402. The second segment S2 is threaded clockwise through the third ring 2443, the fourth ring 2444, the fifth ring 2445, skips the sixth ring 2446, threaded clockwise through the seventh ring 2447, the eighth ring 2448, and the ninth ring 2449, and a knot is tied at the tenth ring 2450.

The routing process continues with a third segment S3 of the suture 2402. The third segment S3 threaded clockwise through the eleventh ring 2451, the twelfth ring 2452, the first ring 2441, skips the second ring 2442, threaded clockwise through the third ring 2443, the fourth ring 2444, and the fifth ring 2445, and a knot is tied at the sixth ring 2446. In some embodiments, an excess portion of the suture 2402 may be left behind after being tied to the sixth ring 2446. In some embodiments, the excess portion of the suture 2402 may be the six inches.

The routing process above may be repeated for a second side (atrial of ventricular) of the replacement valve 2400. The above exemplary tether routing configuration is based upon a stent structure comprising twelve longitudinal struts, and therefore comprises an arrangement of twelve tether rings used with three tethers. The arrangement, however, may be generalized to stents with other numbers of struts or rings. For example, the relationship between the number of rings and the arrangement of subsets for the number of tethers X, is that for X number of subset of rings, N number total rings should be divisible by X+1. Each subset of rings, however, may be configured with any number Y of rings. Thus, in the embodiment depicted in FIG. 24, there are N=12 rings with X=3 subsets for each X=3 tether, with each subset comprising Y=3 rings. In other variations, however, the number of tethers could be two, requiring X=2 two subsets, the number of rings or longitudinal struts would need to be a multiple of three (X+1), so N could be 3, 6, 9, 12, 15, 18 etc. but because the number of subsets is even, usable configurations would have 6, 12 or 18 rings, or where subsets have a ring count of Y=3, Y=6 or Y=9. For the configuration in FIG. 25, FIG. 25 illustrates a schematic end view of a routing process pattern of a suture 2502 to collapse a replacement valve 2500 and maintain the replacement valve 2500 in a collapsed configuration. The replacement valve 2500 may comprise a plurality of ring structures 2540 that may be similar to the ring structures 2240 discussed in relation to FIG. 22A-22D. In the illustrated schematic, the replacement valve 2500 includes twelve ring structures 2540 that are equally spaced along a circumference of a stent frame 2510. The twelve ring structures are disposed at the twelve hour positions of an analog clock, and include a first ring 2541, a second ring 2542, a third ring 2543, a fourth ring 2544, a fifth ring 2545, a sixth ring 2546, a seventh ring 2547, an eighth ring 2548, a ninth ring 2549, a tenth ring 2550, an eleventh ring 2551, and a twelfth ring 2552.

The routing process of FIG. 25 begins with a first segment S1 of the suture 2502 tied to the fifth ring 2545. In some embodiments, an excess portion of the suture 2502 may be left behind and used in the routing process. In some embodiments, the excess portion of the suture 2502 may be six inches. The first segment S1 of the suture 2502 is threaded clockwise through the sixth ring 2546, the seventh ring 2547, the eighth ring 2548, the ninth ring 2549, skips the tenth ring 2550, threaded counterclockwise through the eleventh ring 2551 from the far side (as illustrated), threaded counterclockwise through the tenth ring 2550, and a knot is tied at the ninth ring 2549.

The routing process continues with a second segment S2 of the suture 2502. The second segment S2 is threaded clockwise through the tenth ring 2550, the eleventh ring 2551, the twelfth ring 2552, the first ring 2541, skips the second ring 2542, threaded counterclockwise through the third ring 2543 from the far side (as illustrated), threaded counterclockwise through the second ring 2542, and a knot is tied at the first ring 2541.

The routing process continues with a third segment S3 of the suture 2502. The third segment S3 is threaded clockwise through the second ring 2542, the third ring 2543, the fourth ring 2544, the fifth ring 2545, skips the sixth ring 2546, threaded counterclockwise through the seventh ring 2547 from the far side (as illustrated), threaded counterclockwise through the sixth ring 2546, and a knot is tied at the fifth ring 2545. In some embodiments, an excess portion of the suture 2502 may be left behind after being tied to the fifth ring 2545. In some embodiments, the excess portion of the suture 2502 may be the six inches.

The routing process above may be repeated for a second side (atrial of ventricular) of the replacement valve 2500. Like with the stent configuration illustrated in FIG. 24, the above exemplary tether routing configuration is based upon a stent structure comprising twelve longitudinal struts, and therefore comprises an arrangement of twelve tether rings used with three tethers. The arrangement, however, may be generalized to stents with other numbers of struts, rings or tethers, or different levels of overlap or ring skipping among or between the tethers. For example, in an alternative embodiment, a first suture segment may be attached to a first anchor ring of the plurality of rings and threaded in a first direction through a first X consecutive rings of the plurality of rings immediately adjacent to the first anchor ring, wherein X>0, skipping in the first direction Y rings immediately adjacent to the first X consecutive rings, and threaded in the second direction through Z consecutive rings of the plurality of rings, wherein Z is zero or greater than one, and Z<X, and attached to the next consecutive ring of the plurality of rings in the first direction if Z=0, or the next consecutive rings of the plurality of rings in the second direction if Z>0. A second suture segment attached to the same ring as the first segment of suture that is not the first anchor ring, and threaded in the first direction through a second X consecutive rings of the plurality of rings, skipping in the first direction Y rings of the plurality of rings immediately adjacent to the second X consecutive rings, threaded in the second direction Z consecutive rings of the plurality of rings, wherein Z is zero or greater than one, and Z<X, and attached to the next consecutive ring of the plurality of rings from the second X consecutive rings in the first direction if Z=0, or the next consecutive rings of the plurality of rings in the second direction if Z>0. A third suture segment attached to the same ring as the second suture segment corresponding to the next consecutive ring from the second X consecutive rings in the first direction if Z=0, or the next consecutive rings in the second direction if Z>0 in the first direction, and threaded through a third X consecutive rings of the plurality of rings, skipping in the first direction Y rings immediately adjacent to the third X consecutive rings, threaded in the second direction Z consecutive rings of the plurality of rings, wherein Z is zero or greater than one, and Z<X, and attached to the next consecutive ring from the third X consecutive rings in the first direction if Z=0, or the next consecutive rings in the second direction if Z>0. Within this framework of tether routing, various tether configurations may be generated, e.g.:

A) X=3, Y=1 and Z=0.

B) X=4, Y=1 and Z=2.

C) X≥2.

D) X–Z=2.

Figures 27, 28:
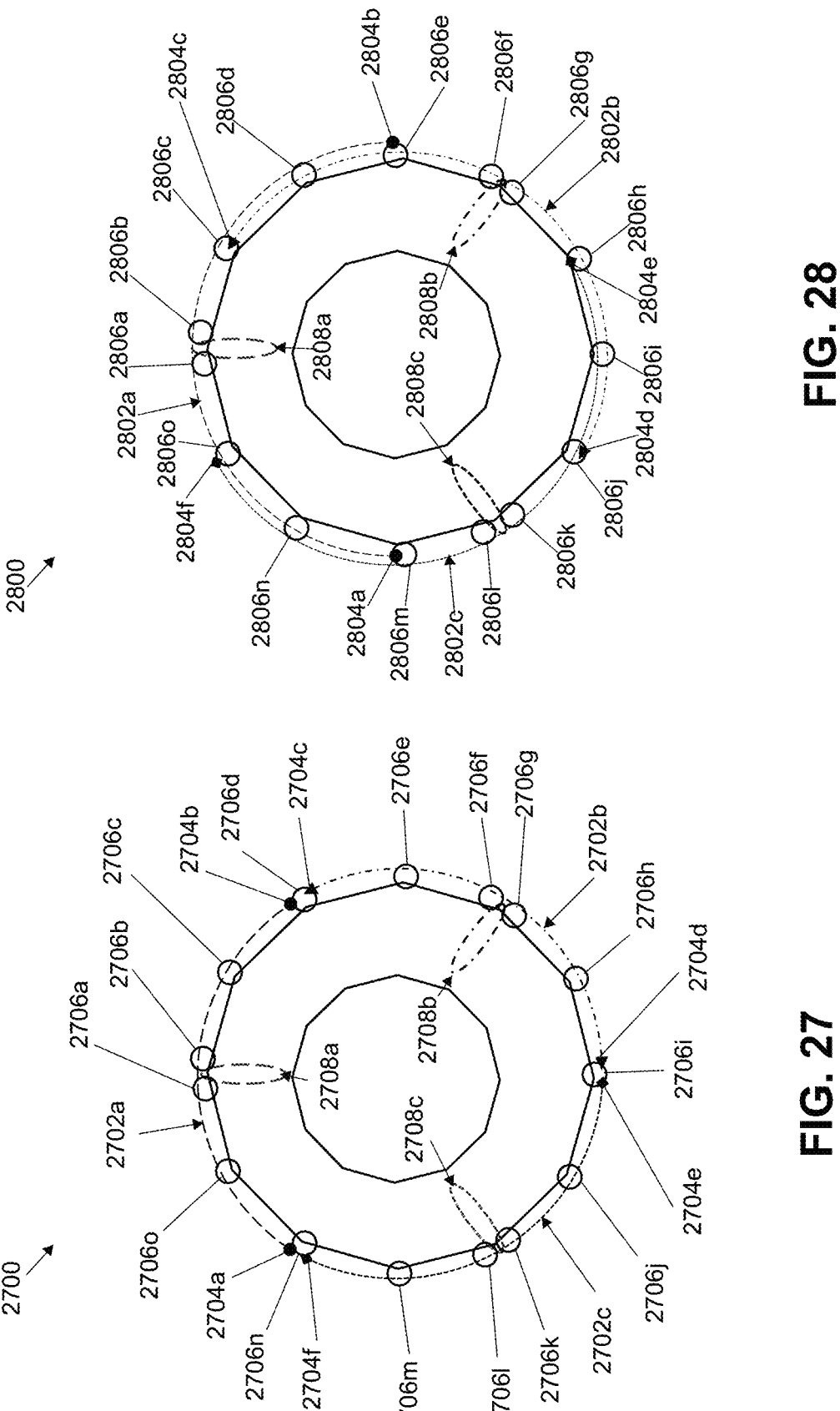
FIG. 27 is a schematic depiction of exemplary tether line attachment and loop configuration, utilizing multiple separate tether lines in a non-overlapping configuration.
FIG. 28 is a schematic depiction of another exemplary tether line attachment and loop configuration, utilizing multiple separate tether lines in an overlapping configuration.

In another embodiment, depicted in FIG. 27, a stent 2700, comprising a plurality of non-overlapping tethers 2702*a-c*, wherein the ends 2704*a-f* of each tether 2702*a-c* are attached to a tether retention structure or ring 2706*d,h,m*. Each tether 2702*a-c* has a nominal coverage length of one-third the stent circumference, or a 120 degree arc. Each structure 2706*d, h,m* is attached by two of the tethers 2702*a-c*, and paired or double rings 2706*a-b, f-g, j-k* are provided to reinforce the locations where the tether loops 2708*a-c* are pulled out to engage the delivery system. Each tether 2702*a-c* also slidably engages other rings 2702*c,e,h,j,m,o* that are located between the attachment rings 2706*d,h,m* and the paired rings

2706*a-b, f-g, j-k*. The depicted tether configuration may be applicable to any circumferential tether configuration location as described herein, e.g., at the end tips and/or strut junctions of the inner wall, outer wall, and/or transition wall or other support struts. In this specific example, the stent 2700 has twelve longitudinal struts which correspond to clock hour positions 12 to 11 o'clock of each location of the single or paired rings 2706*a-0*. Three separate tethers 2704*a-*2704*c* are provided, with the first tether 2702*a* comprising ends 2704*a*, 2704*b* that are fixedly attached to rings 2706*n* and 2706*d*, respectively, slidably engaged to single rings 2706*o* and 2706*c*, and to paired rings 2706*a*, 2706*b*, between which loop 2708*a* is pulled. Similarly, tether 2702*b* comprises ends 2704*c*, 2704*d* that are fixedly attached to rings 2706*d*, 2706*i*, and is slidably engaged to single rings 2706*e*, 2706*h*, and paired rings 2706*f* and 2706*g*, between which loop 2708*b* is pulled. Finally, tether 2702*c* comprises ends, 2704*c*, 2704*f* that are fixedly attached to rings 2706*i*, 2706*n*, respectively, and is slidably engaged to single rings 2706*j*, 2706*m* and to paired rings 2706*k*, 2706*l* between which loop 2708*c* is pulled or engaged. In other stent structures with a different number of tether retention rings or structures, each tether retains the same relative configuration of attachment structures and paired retention structures, but where the single retention structures located between the attachment structure and the paired retention structures will be absent or comprise additional slidably engaged retention structures, if the number of tether lines remains the same. In still other variations, with a greater number of longitudinal struts or tether retention structures, a greater number of tether lines may be provided to maintain a similar arrangement for each tether.

FIG. 28 depicts one embodiment of a tether configuration of a stent 2800, comprising a plurality of overlapping tethers 2802*a-c*, wherein each tether 2802*a-c* nominally encircles half of the circumference of the stent 2800, e.g., 180 degrees. In the overlapping configuration, only the middle third of the tether 2802*a-c* where the loop 2808*a-c* is located, is non-overlapping, while the end third of each tether 2802*a-c* is overlapping with the adjacent tether 2802*a-c*. In contrast to the tether configuration in FIG. 27, wherein the each ring that is fixedly attached to a tether is attached by two tethers, in the embodiment depicted in FIG. 28, the ends 2804*a-f* of the tethers 2802*a-c* are fixedly attached to tether retention structures or rings 2806*m,e,c,j, h,o*, respectively, that are not fixedly attached to other tethers 2802*a-c*, but are slidably passed through or engaged an adjacent tether 2802*a-c* as a result of the overlapping configuration. Paired or double rings 2806*a-b, f-g, j-k* are still provided to reinforce the locations where the tether loops 2808*a-c* are pulled out to engage the delivery system. Each of the paired rings 2806*a-b, f-g, j-k* are slidably engaged by only one tether 2802*a-c*, respectively, but the rings 2806*d,i,n* are each slidably engaged to two overlapping tethers 2802*a-c*. The depicted tether configuration may be applicable to any circumferential tether configuration location as described herein, e.g., at the end tips and/or strut junctions of the inner wall, outer wall, and/or transition wall or other support struts. In this specific example, the stent 2800 also has twelve longitudinal struts which correspond to clock hour positions 12 to 11 o'clock of each location of the single or paired rings 2806*a-0*, respectively. Three separate tethers 2804*a-*2804*c* are provided, with the first tether 2802*a* comprising ends 2804*a*, 2804*b* that are fixedly attached to rings 2806*m* and 2806*e*, respectively, slidably engaged to rings 2806*n-o,c-d* and to paired rings 2806*a-b*, between which loop 2808*a* is pulled. Similarly, tether 2802*b* comprises ends 2804*c*, 2804*d* that are fixedly attached to rings 2806*c*, 2806*j*, and is slidably engaged to single rings 2806*d*-*c*,*h*-*i*, and paired rings 2806*f*-*g*, between which loop 2808*b* is pulled. Finally, tether 2802*c* comprises ends, 2804*c*, 2804*f* that are fixedly attached to rings 2806*h*, 2806*o*, respectively, and is slidably engaged to single rings 2806*i*-*j*,*m*-*n* and to paired rings 2806*k*-*l* between which loop 2808*c* is pulled or engaged. In other stent structures with a different number of tether retention rings or structures, each tether retains the same relative configuration of attachment structures and paired retention structures, but where the single retention structures located between the attachment structure and the paired retention structures will be absent or comprise additional slidably engaged retention structures, if the number of tether lines remains the same. In still other variations, with a greater number of longitudinal struts or tether retention structures, a greater number of tether lines may be provided to maintain a similar arrangement for each tether.

Figure 29:
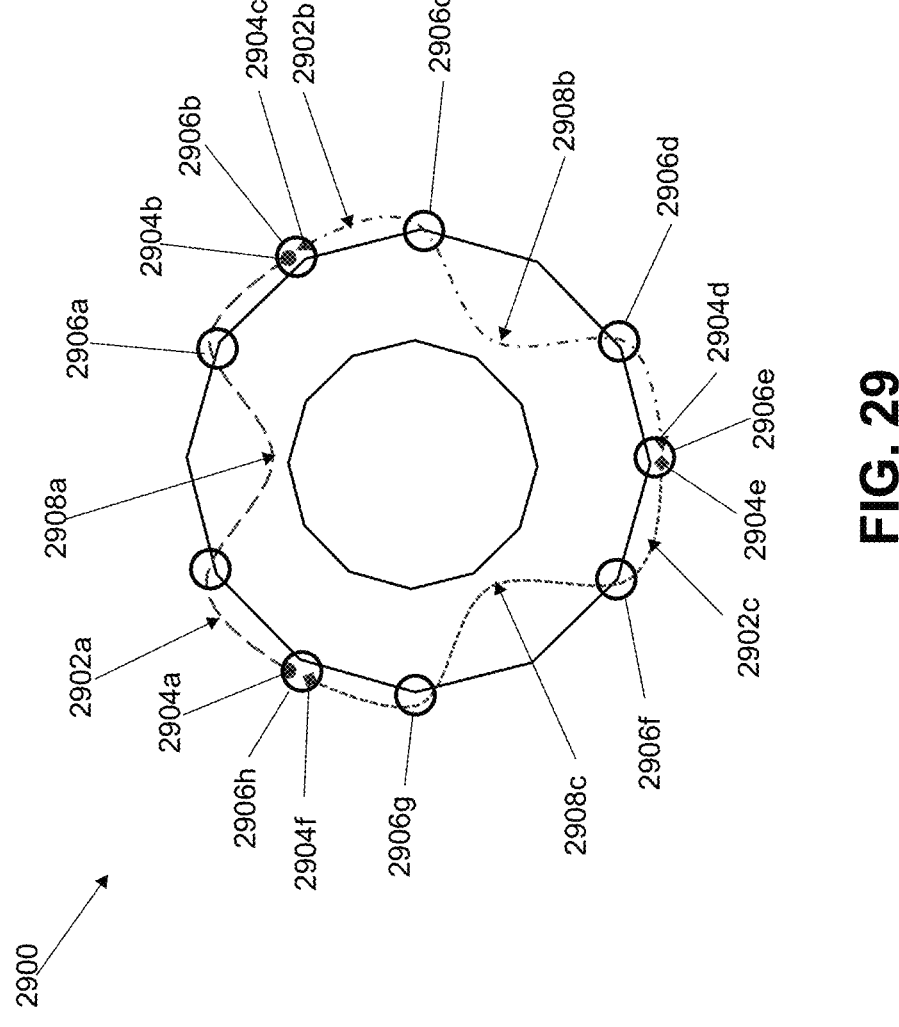
FIG. 29 is a schematic illustration of another exemplary tether line attachment and loop configuration.

FIG. 29 depicts one embodiment of a tether configuration of a stent 2900, comprising a plurality of non-overlapping tethers 2902*a*-*c* similar to the tether configuration of stent 2700 in FIG. 27, except where the paired tether retention structures or rings are not provided or otherwise not used for tether routing. In this variation, the loops 2908*a*-*c* of the tethers 2902*a*-*c* have a broader base pulled between two single rings 2906*i*-*a*,*c*-*d*, *f*-*g* that are spaced apart by more than 5 or 10 degrees, e.g., by 30 degrees or more, or 60 degrees or more. In this tether configuration, the ends 2904*a*-*f* of each tether 2902*a*-*c* are attached to a tether retention structure or rings 2906*h*,*b*,*c*. Each tether 2902*a*-*c* has a nominal coverage length of one-third the stent circumference, or a 120 degree arc. Each tether retention structure 2906*h*,*b*,*c* is attached by two of the tethers 2902*a*-*c*, and single rings 2906*i*-*a*,*c*-*d*,*f*-*g* spaced apart by 60 degrees and also support the tether loops 2908*a*-*c* that are pulled out to engage the delivery system. This depicted tether configuration may be applicable to any circumferential tether configuration location as described herein, e.g., at the end tips and/or strut junctions of the inner wall, outer wall, and/or transition wall or other support struts. In this specific example, the stent 2900 has twelve longitudinal struts which correspond to clock hour positions 12 to 11 o'clock of each location. Locations 2910*a*-*c*, which are spaced 120 degrees apart, lack any tether retention structure or ring. Three separate tethers 2904*ac* are provided, with the first tether 2902*a* comprising ends 2904*a*-*b* that are fixedly attached to rings 2906*h* and 2906*b*, respectively, slidably engaged to single rings 2906*i* and 2906*a*, between which loop 2908*a* is pulled. Similarly, tether 2902*b* comprises ends 2904*c*-*d* that are fixedly attached to rings 2906*b*, 2906*e*, and is slidably engaged to single rings 2906*c*-*d*, between which loop 2908*b* is pulled. Finally, tether 2902*c* comprises ends, 2904*e*-*f* that are fixedly attached to rings 2906*e*, 2906*h*, respectively, and is slidably engaged to single rings 2906*f*-*g* between which loop 2908*c* is pulled or engaged. In other stent structures with a different number of tether retention rings or structures, each tether retains the same relative configuration of attachment structures and paired retention structures, but where the single retention structures located between the attachment structure and the paired retention structures will be absent or comprise additional slidably engaged retention structures, if the number of tether lines remains the same. In still other variations, with a greater number of longitudinal struts or tether retention structures, a greater number of tether lines may be provided to maintain a similar arrangement for each tether.

Figures 30A, 30B:
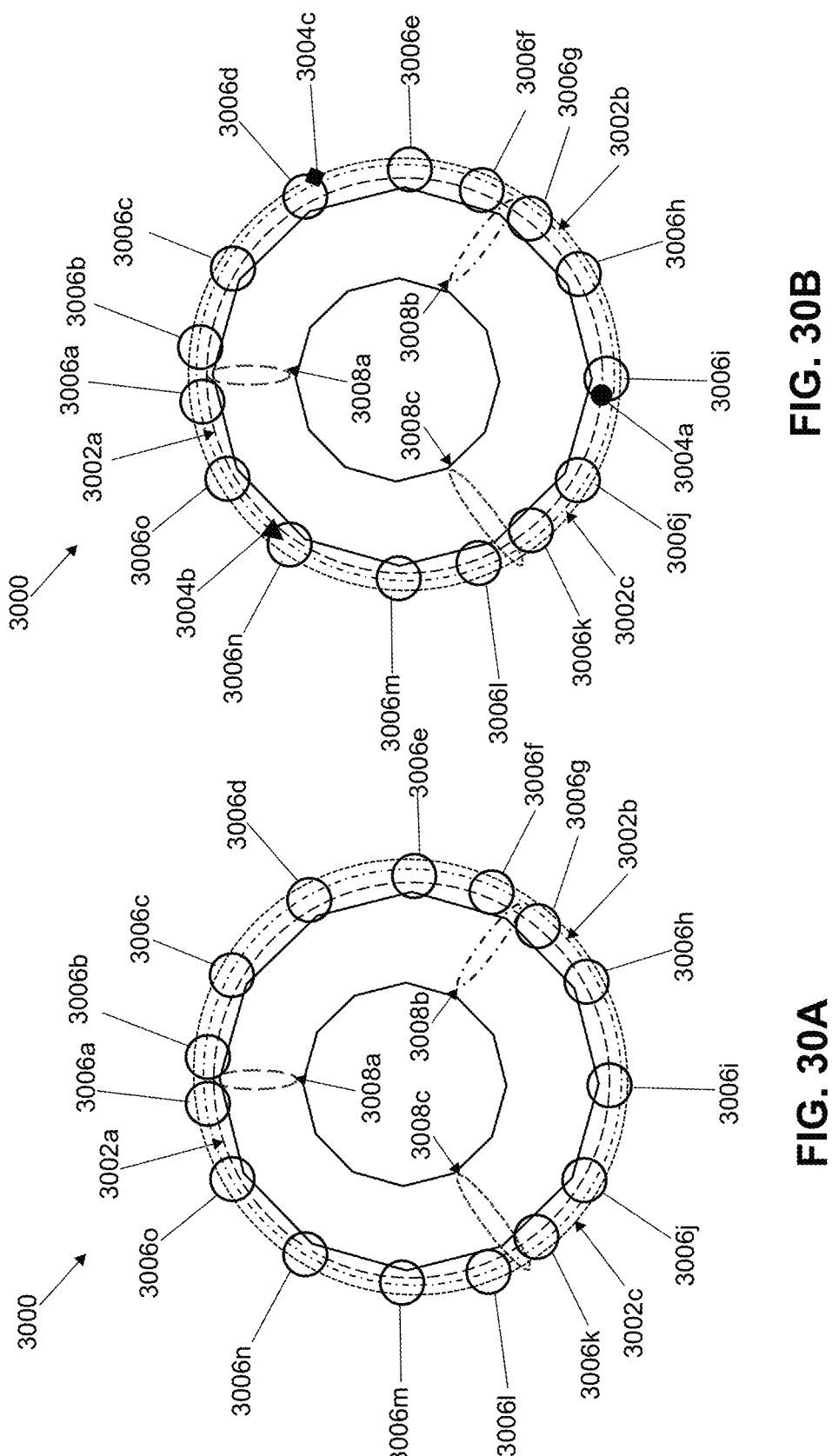
FIGS. 30A and 30B are schematic illustrations of other exemplary tether lines and loop configurations, utilizing multiple fully circumferential tethers in an unattached and attached configurations, respectively.

In still another variation of an exemplary tether configuration usable with a stent assembly, FIG. 30A depicts a stent 3000 comprising a plurality of tether lines 3002*a*-*c* that are intact and form a closed shape, e.g., without any ends or wherein the ends of the tether lines are tied together to form a closed shape. In the variation depicted in FIG. 30A, each tether line 3002*a*-*c* is slidably passed through each tether retention structure 3006*a*-*o*. The loop 3008*a*-*c* of each tether line 3002*a*-*c* is still provided with a corresponding double tether retention structure 3006*a*-*b*, 3006*f*-*g*, 3006*k*-*l*, to supports its loop 3008*a*-*c*. In other variations, however, a double tether retention structure is not provided at any of the path locations, and the loops of each tether may be supported by separate single tether retention structures located at uniformly circumferentially located positions along the circumferential tether path. In some variations, the closed loop tether 3002*a*-*c* permits the tether 3002*a*-*c* to slide around the circumferential tether path without any mechanical restriction, e.g., only frictional resistance between the tether retention structure and the tether. In other variations, however, the closed shaped tether line 3002*a*-*c* may still be attached to one of the tether retention structures 3006*a*-*o*, as depicted in FIG. 30B. in this variation, each tether loop 3002*a*-*c* is still provided with a double or pair of tether retention structures 3006*a*-*b*, 3006*f*-*g*, 3006*k*-*l*, respectively, to support its loop 3008*a*-*c*. In addition, each closed shape tether loop 3002*a*-*c* is also attached at one or more other tether retention structures 3006*h*-*j*, 3006*m*-*o*, 3006*c*-*e*, respectively. In some further variations, the tether retention structure is at the location circumferentially opposite of the loop 3008*a*-*c* of the tether 3002*a*-*c*, e.g., tether retention structure 3006*i*, 3006*n*, 3006*d*. The attachment may be performed using an adhesive, thermoplastic polymer, suture or clip, for example. In still other variations, one location of the close-shaped tether may instead be attached directly to a strut of the stent. In other embodiments, one or more blocking structures may be attached to the tether, to restrict passage of the tether between two tether retention structures, but not to directly attach the tether, whether close-shaped or open-shaped with two ends. Depending on the size of the blocking structure, some limited movement may be provided between the two tether retention structures.

In some embodiments of the stent assembly, where two tether configurations are provided, each tether configuration may have the same number of tethers, the same number of tether retention structures or rings at analogous stent locations between the junction locations and stent tip locations, the same relative tether attachment locations, and/or the same overlapping or non-overlapping arrangement. In other variations, however, the two tether configurations may be different. For example, the number of tethers may be different and/or the use of overlapping or non-overlapping tethers may be different. In some variations, the ventricular or outflow end of the stent assembly may utilize an overlapping tether configuration as described herein, while the atrial or inflow of stent assembly may utilize a non-overlapping tether configuration as described herein. In still another variation, the ventricular or outflow end of the stent assembly may utilize a non-overlapping tether configuration as described herein, while the atrial or inflow of stent assembly may utilize an overlapping tether configuration as described herein.

The routing processes of the present disclosure are not limited to the routing processes discussed in relation to FIGS. 24, 25 and 27 to 29. In some embodiments of the stent assembly, where two tether configurations are provided, each tether configuration may have the same number of tethers, the same number of tether retention structures or rings at analogous stent locations between the junction locations and stent tip locations, the same relative tether attachment locations, and the same overlapping or non-overlapping arrangements. In other variations, however, the two tether configurations may be different. For example, the number of tethers may be different and/or the use of overlapping or non-overlapping tethers may be different. In some variations, the ventricular or outflow end of the stent assembly may utilize an overlapping tether configuration as described herein, while the atrial or inflow of stent assembly may utilize a non-overlapping tether configuration as described herein. In still another variation, the ventricular or outflow end of the stent assembly may utilize a non-overlapping tether configuration as described herein, while the atrial or inflow of stent assembly may utilize an overlapping tether configuration as described herein.

Also, in the specific examples illustrated in FIGS. 24 and 26, and in FIGS. 27 to 29, the exemplary stent structure is configured with 12 longitudinal struts to provide uniform and distributed support for a three-leaflet heart valve. The number of rings provided in the exemplary embodiments are also adapted to correspond to the number of struts, which in turn is related to the number of commissures of the three-leaflet heart valve, e.g., there are four times as many longitudinal struts as there are valve commissures. In other embodiments, however, a different multiple may be used, e.g., 1×, 2×, 3×, 5×, or a multiple in the range of 1× to 4×, or 2× to 5×, or 3× to 5×m, may be used. A different number of tether lines may also be utilized, e.g., two tether lines, or four tether lines per stent end. The exemplary ring configurations illustrated in FIGS. 24 and 25 may thus be adapted to other stent configurations.

Manufacturing

In some variations, the stent structure may be manufactured using a super-elastic nitinol tube that is laser cut with various slits and slots to achieve the initial tubular stent shape. Next, in a series of cyclic deformation, heating, and cooling steps, the tubular stent is expanded stepwise to at least the initial size of the inner lumen of the stent structure. Then the portion of the stent structure corresponding to the transition wall and outer wall are than further expanded stepwise to the desired diameter, and followed by a stepwise eversion to form the outer wall using a mandrel, and a stepwise reduction of the middle region of the outer wall, or further expansion of the upstream and downstream end regions of the outer wall, is performed to achieve the reduce diameter shape of the outer wall. In another step, one or more bend regions on the lateral struts about the middle region are radially displaced outward to form the retention barbs or structures.

In an alternate embodiment, after initial cutting the tube, the tube may undergo a series of cyclic deformation, heating, and cooling steps, to expand the tube in a stepwise manner to at least the initial size of the outer lumen of the stent structure, then the portion of the stent structure corresponding to the transition wall and inner wall are then inverted into the outer wall to form the closed end and the inner wall. The outer wall may be further expanded or adjusted stepwise to the desired shape, e.g., by further expanding the open and closed end regions of the outer wall, or by reducing the cross-sectional size or diameter of the middle region. One or more bend regions on the lateral struts about the middle region may also be radially displaced outward to form the retention barbs or structures Valve Loading and Delivery As noted previously, a plurality of control apertures may be provided on stent structure, which may be used to attach one or more sutures to control the expansion and contraction of different regions on the stent structure, and/or one or more hooks to releasably retain the stent structure until final deployment at the treatment site. In other examples, rather than using a control aperture, a suture or wrap may be provided over the exterior of one or more regions of the stent structure.

In some examples, the sutures may be tensioned or cinched to collapse the outer and inner walls of the stent structure, for loading onto the delivery catheter. The sutures may be manipulated to collapse inner wall first, before the outer wall, or may collapse both simultaneously. Similarly, one end of the inner wall or outer wall may be collapsed first, or both ends of the inner wall or outer wall may be collapsed simultaneously. This may be done at room temperature, or in a sterile cold or ice water bath at the point of use or at the point of manufacture. After collapse, a sheath may be extended distally over the distal catheter portion where the replacement valve resides. The valve may also be rinsed in sterile saline before loading to remove any remaining preservative on the valve.

In some variations, the transition wall of the stent structure folds down at the inner junction such that in the collapsed configuration, the transition wall is positioned directly over the delivery catheter or tool, like the inner wall, but in other examples, the outer wall is pulled distally during collapse and loading, and unfolds the transition wall at the outer junction, such as the transition wall is located radially outward from the inner wall when contracted into the collapsed configuration.

The retaining sutures of the delivery system may be controlled proximally by the user with pulling rings, sliding levers, and/or rotating knobs, which are further configured to lock into place except during movement via bias springs or mechanical interfit locking configurations as known in the art. The proximal end of the delivery system may also be controlled robotically, using any of a variety of robotic catheter guidance systems known in the art. The sutures may slide along one or more interior lumens of the delivery catheter, in addition to any flush lumen, guidewire lumen, or steering wire lumen(s) provided, including rapid exchange guidewire configurations. The sutures may exit at different locations about the distal region of the delivery catheter, and may exit about the distal region of the catheter via multiple openings. The multiple openings may be spaced apart around the circumference of the catheter body and/or spaced apart longitudinally, depending on the region of the stent structure controlled by sutures.

In one exemplary method of delivering the replacement valve, the patient is positioned on the procedure table, and the draped and sterilized in the usual fashion. Anesthesia or sedation is achieved. Percutaneous or cutdown access to the femoral vein is obtained and an introducer guidewire is inserted. A guidewire is manipulated to reach the right atrium and then a Brockenbrough needle is positioned and used to puncture the interatrial septum to achieve access to the left atrium. Alternatively, image guidance may be used to detect whether a patent septum ovale or remnant access is available, and the guidewire may be passed through the pre-existing anatomical opening. A balloon catheter may also be used as need to enlarge the opening across the intra-atrial septum. An electrocautery catheter may also be used to form an opening in the intra-atrial septum. Once in the left atrium, the guidewire is passed through the mitral valve and intro the left ventricle. Pre-shaped guidance catheters or balloon catheters may be used to facilitate the crossing of the mitral valve. Once in the left ventricle, the delivery catheter with the replacement valve is inserted over the guidewire.

Figures 8A, 8B, 8C:
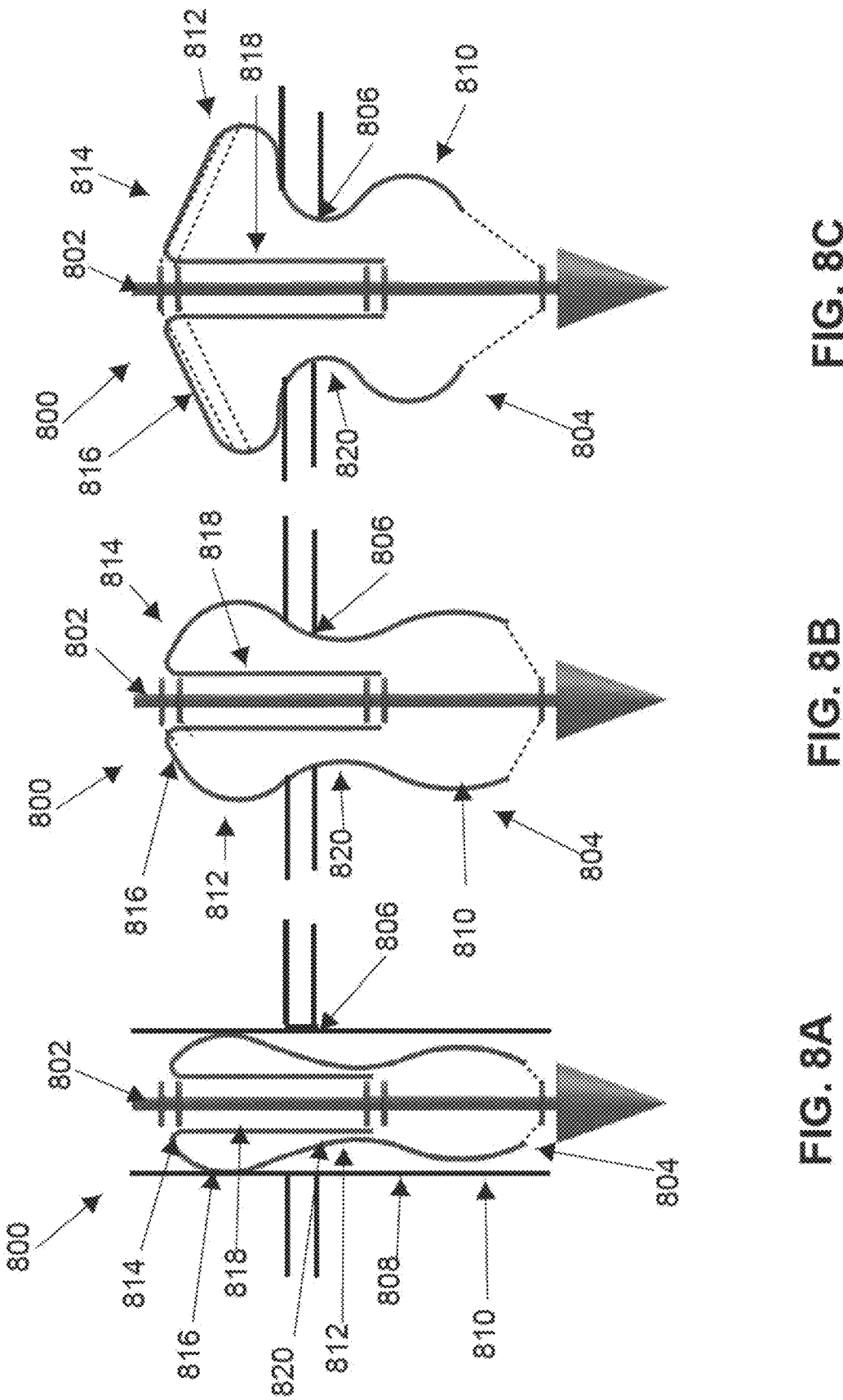
FIGS. 8A to 8E are schematic cross-sectional views of an exemplary views of a deployment procedure for a heart valve stent and delivery system.

Referring to FIG. 8A, the delivery system 800 with the delivery catheter 802 and valve 804 is positioned across the mitral valve opening 806. The delivery system 800 may also be further manipulated to adjust the angle of entry through the mitral valve opening 806 to be roughly orthogonal to the native valve opening and/or to be centered with the mitral valve opening 806. Once the desired catheter pose is achieved, the delivery sheath 808 is withdrawn proximally, to expose the collapsed valve 804.

In FIG. 8B, the set of sutures controlling the release of the downstream or ventricular end 810 of the outer wall 812 of the valve 804 is partially released, while the tension members controlling the inner wall 816 remains tensioned. Next, in FIG. 8C, ventricular end 810 of the outer wall 812 of the valve 804 is further released, allowing the ventricular end, the middle region and more of the atrial end 814 of the outer wall 812 to expand further, thereby allowing the transition wall 816 of the valve 804 to at least partially expand outward. The partial expansion of the atrial end 814 and the ventricular end 810 of the valve 804 helps to further center and orient the middle region 820 of the valve 804 orthogonally prior to complete release. While the initial expansion of the atrial end 814 of the outer wall 812 in this embodiment is a secondary effect from the partial release of the ventricular end 810 of the valve 804 as longitudinal tension is released, in other examples, independent tension member control of the atrial end 814 may be provided.

Figures 8D, 8E:
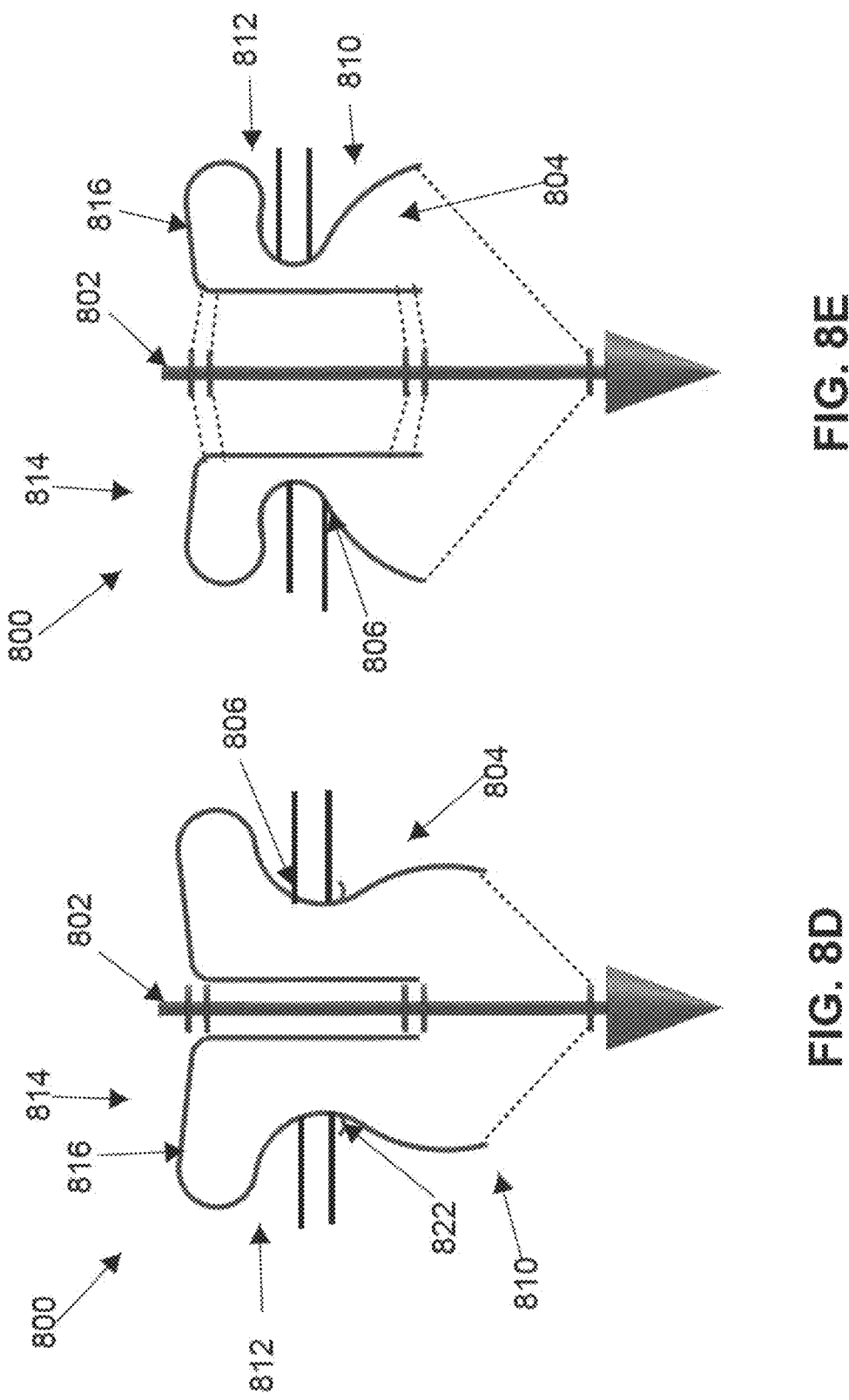

In FIG. 8D, the tension members of the ventricular end 810 and atrial end 814 are further released, either simultaneously or singly in a stepwise fashion, further engaging the middle region 820 of the outer wall 812 against the valve opening 806. This further expansion of the outer wall 812 also exposes the retention barbs or projections 822 on the outer wall 812. Proper centering and orientation of the valve is reconfirmed, to make sure the valve has not been deployed in a skewed or partially disengaged pose with respect to the mitral valve annulus. In some variations, the tension members may be re-tensioned to re-collapse the valve 804 may be performed, to facilitate re-positioning and/or re-orienting of the valve 804. Once confirmed, the tension members of the inner wall 818 may be released, as shown in FIG. 8E, which also allows the outer wall 812 to achieve its untethered expansion against the mitral valve opening 806. The tension members can then be cut or otherwise released or separated from the valve and the tension members may be withdrawn into the catheter and optionally out of the proximal end of the catheter. The delivery catheter and guidewire can then be withdrawn from the patient and hemostasis is achieved at the femoral vein site.

In one exemplary method of delivering the replacement valve, the patient is positioned on the procedure table, and the draped and sterilized in the usual fashion. Anesthesia or sedation is achieved. Percutaneous or cutdown access to the vascular or entry site is obtained, e.g., at the femoral vein, femoral artery, radial artery, subclavian artery, and an introducer guidewire is inserted. A guidewire is manipulated to reach the desired valve implantation site. Pre-shaped guidance catheters or balloon catheters may be used to facilitate the crossing of the valve implantation site Referring to FIG. 8A, the delivery system 800 with the delivery catheter 802 and valve 804 is positioned across the valve opening 806. The delivery system 800 may also be further manipulated to adjust the angle of entry through the valve opening 806 to be roughly orthogonal to the native valve opening and/or to be centered with the valve opening 806. Once the desired catheter pose is achieved, the delivery sheath 808 is withdrawn proximally, to expose the collapsed valve 804.

In FIG. 8B, the set of tension members controlling the release of the downstream end 810 of the outer wall 812 of the valve 804 are partially released, while the tension members controlling the inner wall 816 remain tensioned. Next, in FIG. 8C, downstream end 810 of the outer wall 812 of the valve 804 is further released, allowing the downstream end, the middle region 820 and more of the upstream end 814 of the outer wall 812 to expand further, thereby allowing the transition wall 816 of the valve 804 to at least partially expand outward. The partial expansion of the atrial end 814 and the ventricular end 810 of the valve 804 helps to further center and orient the middle region 820 of the valve 804 orthogonally prior to complete release. While the initial expansion of the atrial end 814 of the outer wall 812 in this embodiment is a secondary effect from the partial release of the ventricular end 810 of the valve 804 as longitudinal tension is released, in other examples, independent tension member control of the upstream end 814 may be provided.

In FIG. 8D, the tension members of the downstream end 810 and upstream end 814 are further released, either simultaneously or singly in a stepwise fashion, further engaging the middle region 820 of the outer wall 812 against the valve opening 806. This further expansion of the outer wall 812 also exposes the retention barbs or projections 822 on the outer wall 812. Proper centering and orientation of the valve is reconfirmed, to make sure the valve has not been deployed in a skewed or partially disengaged pose with respect to the valve annulus. The tension members may be optionally re-tensioned to re-collapse the valve 804 may be performed, to facilitate re-positioning and/or re-orienting of the valve 804. Once confirmed, the tension members of the inner wall 818 are released, as shown in FIG. 8E, which also allows the outer wall 812 to achieve its untethered expansion against the mitral valve opening 806. The tension members can then be separated from the valve 804 and withdrawn into the catheter and optionally out of the proximal end of the catheter 804.

In still another exemplary method of delivering the replacement valve, the patient is positioned on the procedure table, and the draped and sterilized in the usual fashion. Anesthesia or sedation is achieved, with selective ventilation of the right lung and optionally the left upper lobe of the lung to permit controlled collapse of the left lower lobe of the lung. A pursestring suture is placed at the transapical or other cardiac entry site. A trocar is inserted through a cannula or introducer with a proximal hemostasis valve, and the trocar assembly is inserted through the pursestring suture to access the cardiac chamber and the target valve.

Referring to FIG. 8A, the delivery system 800 with the delivery rigid tool 802 and valve 804 is positioned across the valve opening 806. The delivery system 800 may also be further manipulated to adjust the angle of entry through the valve opening 806 to be roughly orthogonal to the native valve opening and/or to be centered with the valve opening 806. Once the desired tool pose is achieved, the delivery sheath 808, if any, is withdrawn proximally, to expose the collapsed valve 804.

In FIG. 8B, the tension members controlling the release of the downstream end 810 of the outer wall 812 of the valve 804 are partially released, while the sutures controlling the inner wall 816 remains tensioned. Next, in FIG. 8C, downstream end 810 of the outer wall 812 of the valve 804 is further released, allowing the downstream end, the middle region 820 and more of the upstream end 814 of the outer wall 812 to expand further, thereby allowing the transition wall 816 of the valve 804 to at least partially expand outward. The partial expansion of the atrial end 814 and the ventricular end 810 of the valve 804 helps to further center and orient the middle region 820 of the valve 804 orthogonally prior to complete release. While the initial expansion of the atrial end 814 of the outer wall 812 in this embodiment is a secondary effect from the partial release of the ventricular end 810 of the valve 804 as longitudinal tension is released, in other examples, independent suture control In FIG. 8D, the tension members of the downstream end 810 and upstream end 814 are further released, either simultaneously or singly in a stepwise fashion, further engaging the middle region 820 of the outer wall 812 against the valve opening 806. This further expansion of the outer wall 812 also exposes the retention barbs or projections 822 on the outer wall 812. The tension members may be optionally re-tensioned to re-collapse the valve 804 may be performed, to facilitate re-positioning and/or re-orienting of the valve 804. Proper centering and orientation of the valve is reconfirmed, to make sure the valve has not been deployed in a skewed or partially disengaged pose with respect to the valve annulus. Once confirmed, the tension members of the inner wall 818 are released, as shown in FIG. 8E, which also allows the outer wall 812 to achieve its untethered expansion against the mitral valve opening 806. The suture lines can then be cut and the cut ends withdrawn into the catheter and optionally out of the proximal end of the delivery tool 802.

Figure 9A:
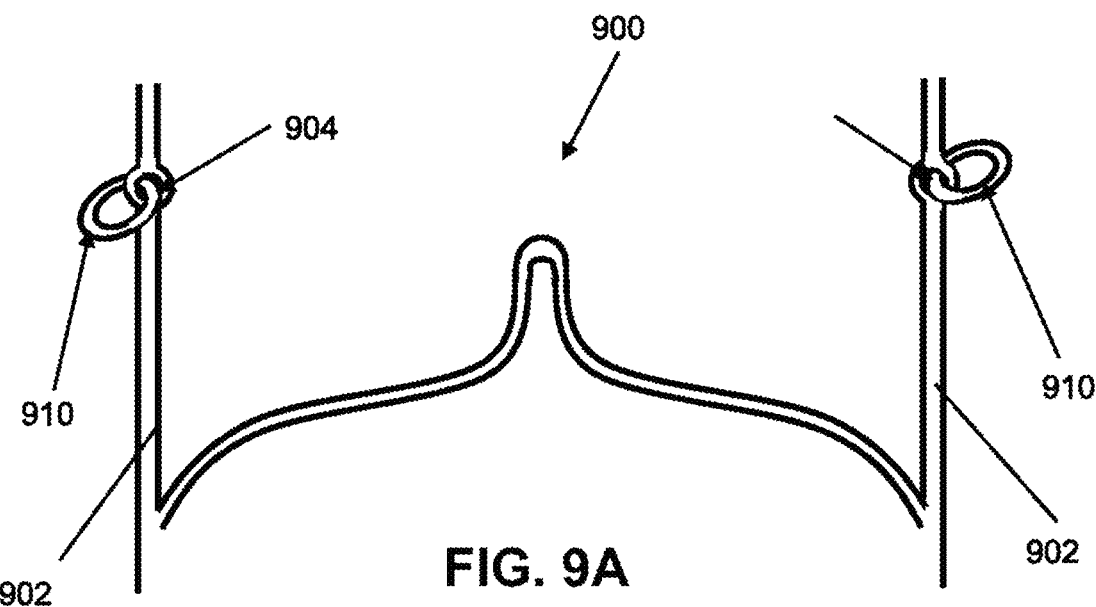
FIGS. 9A to 9C depict various attachment rings located in openings of a stent structure.
Figure 9B:
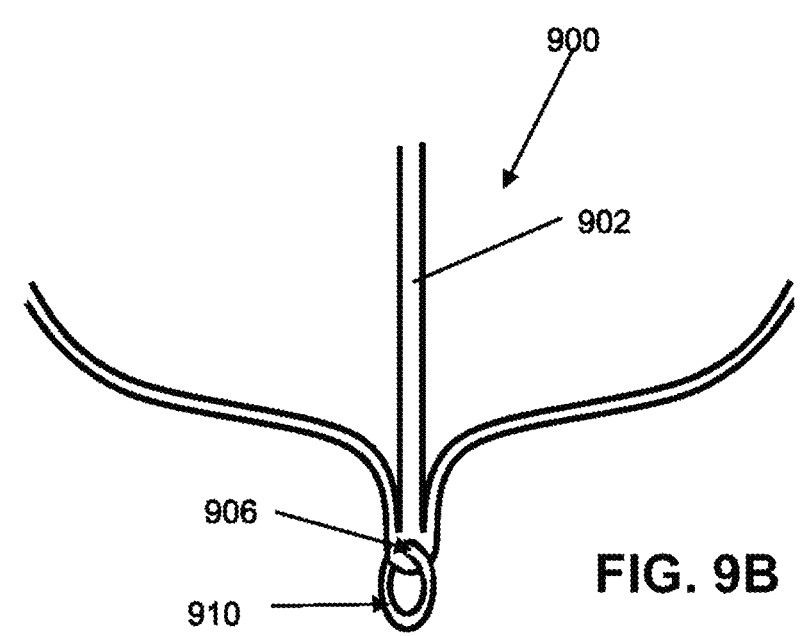
Figure 9C:
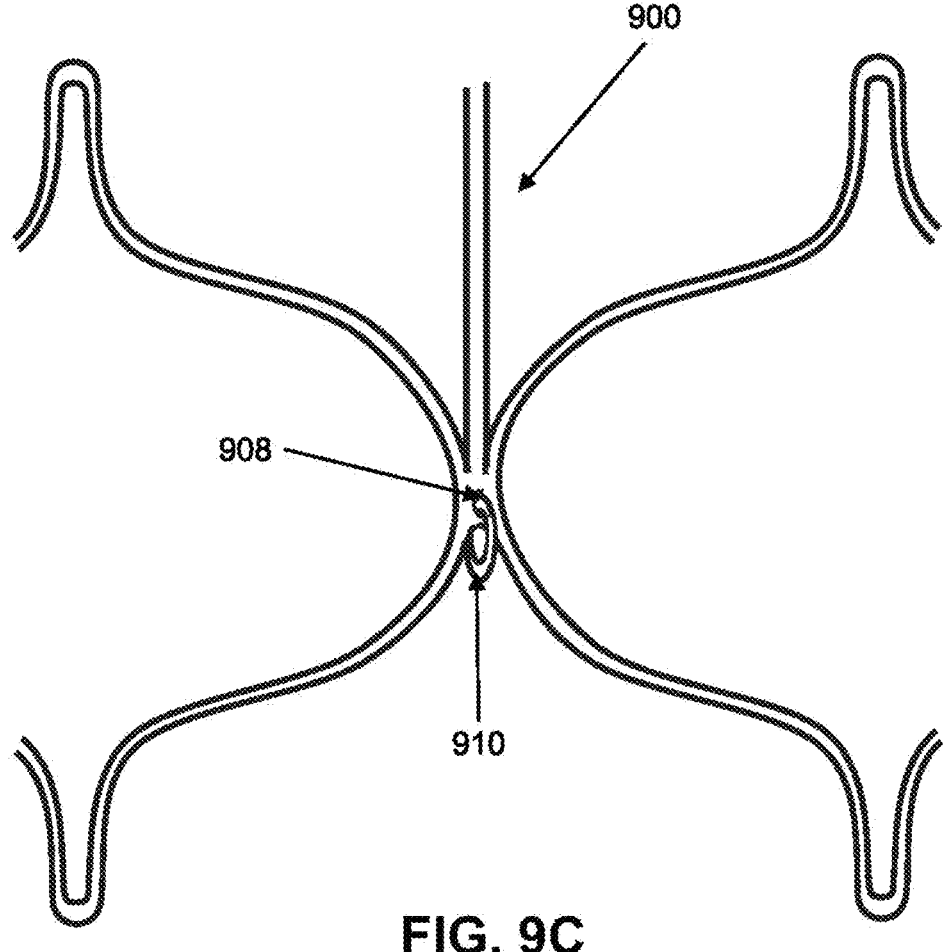
Figure 10:
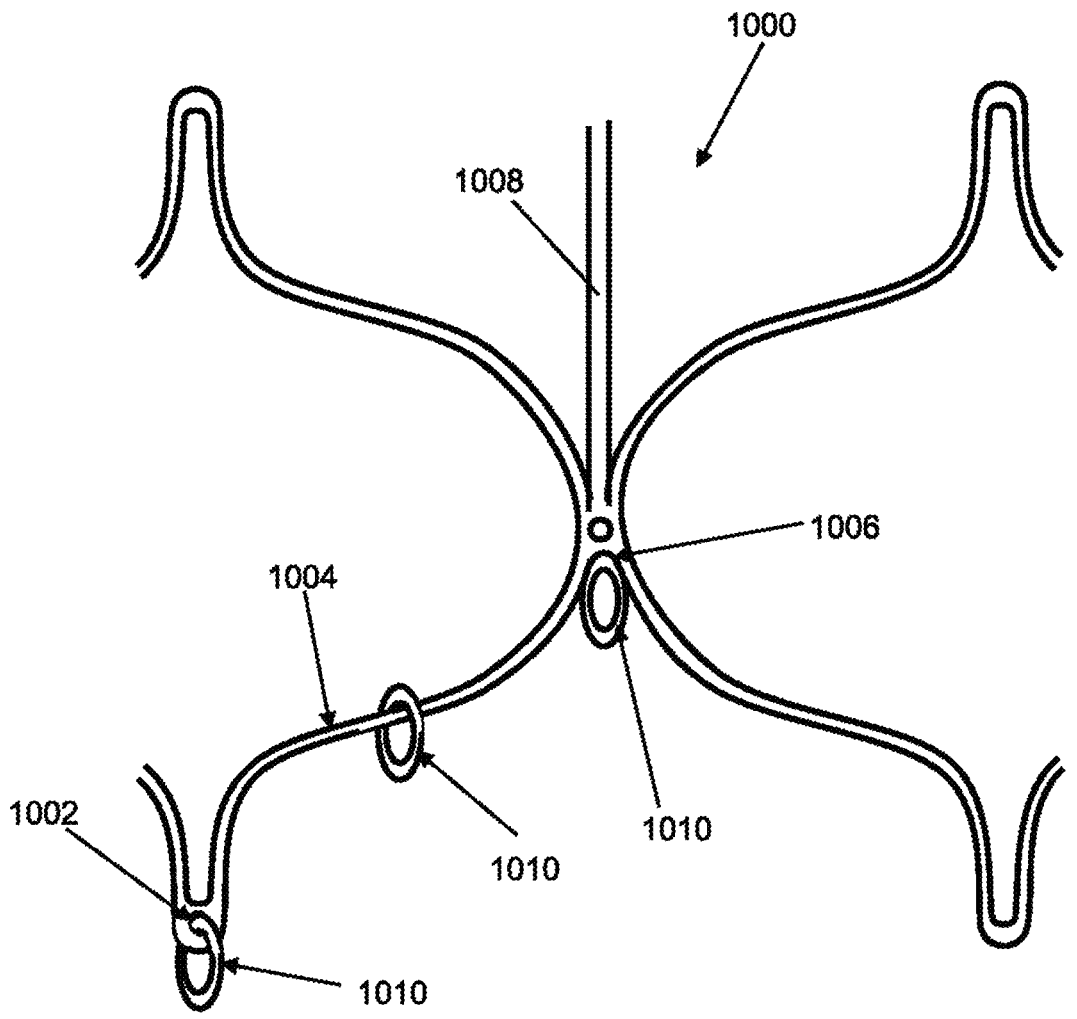
FIG. 10 depicts other exemplary attachment rings coupled to a stent structure.

In some further variations, one or more rings or wire loops may be attached to the stent structure to facilitate attachment of the tensioning members. The rings, in contrast to the stent struts, may comprise a more rounded surface for the tensioning members can slide over. The rings may be directed fixed to the stent structure, or may be provided in an opening of the stent structure. The latter configuration permits the rings to move or rotate in the opening, which may help to orient the tensioning direction between tensioning member and the attachment region of the strut. FIGS. 9A to 9C depict various openings 904, 906, 908 that may be provided on the stent 900. In these particular examples, the openings 904, 906, and 908 are located on the longitudinal struts 902 of the stent 900, but in other variations, as depicted in FIG. 10, the opening 1002 may be located along the lateral or circumferential struts 1004 of the stent 1000. The rings or wire loops 910, 1010 may comprise a circular shape as depicted in FIG. 10, but in other variations, may be oval, square, rectangular or other polygonal or curvilinear closed shape. The rings or wire loops may be formed of round wire with a diameter in the range of 0.001" to 0.100", 0.005" to 0.050", or 0.007" to 0.020", for example, and may comprise a ring or other shape with a diameter or maximum internal opening dimension in the range of 0.010" to 0.5", 0.010" to 0.3", 0.10" to 0.1", 0.010" to 0.080", 0.015" to 0.075", 0.020" to 0.70", 0.25" to 0.65", for example. In some variations, the rings attached to a stent structure may have different sizes, depending on size constraints at a particular location, to provide greater changes to the orientation of the tensioning member. The wire may comprise titanium, stainless steel, nitinol, cobalt-chromium, or other biocompatible wire. The wire may be square cut to provide flat end faces for joining them together, or may be angle cut to increase the surface area for creating a joint. The wire may be crimped into the opening and the ends of the wire may be joined by laser welding a butt joint. The stent structure and the rings may be further processed together, e.g., passivation. In some variations, the ring openings provided formed in the stent structure may have a shape that is the same or different from the cross-sectional shape of the ring, and the relative size may be up to 110%, 120%, 130%, 140%, 150%, 200%, 250%, or 300% of the wire diameter or wire maximum transverse cross-section dimension. The location of the ring openings relative to an end of the strut may also be characterized relative to the wire diameter or wire maximum transverse cross-section dimension, e.g., up to 150%, 200%, 250%, 300%, 400% or 500% or more from the end of the strut or strut segment.

FIG. 10 schematically depicts other embodiments of the stent rings, including a ring 1010 welded to an end 1006 of a longitudinal strut 1008 of stent 1000 in a fixed manner, a ring 1010 slidably located along a circumferential strut 1004, and a ring 1010 located in an opening 1002 of the circumferential strut 1004.

Figure 26A:
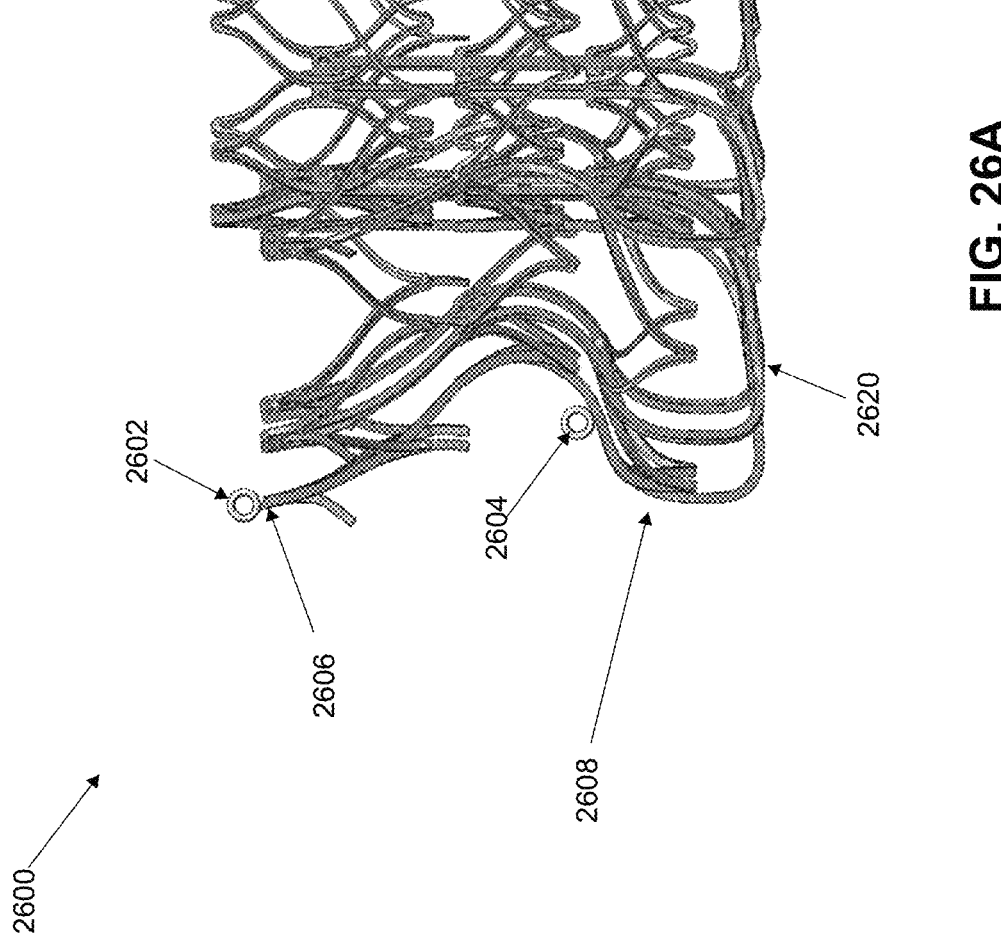
FIG. 26A is a schematic depiction of exemplary attachment regions for tether retention rings or structures on the ventricular region and atrial regions.
Figures 26B, 26C, 26D, 26E, 26F, 26G:
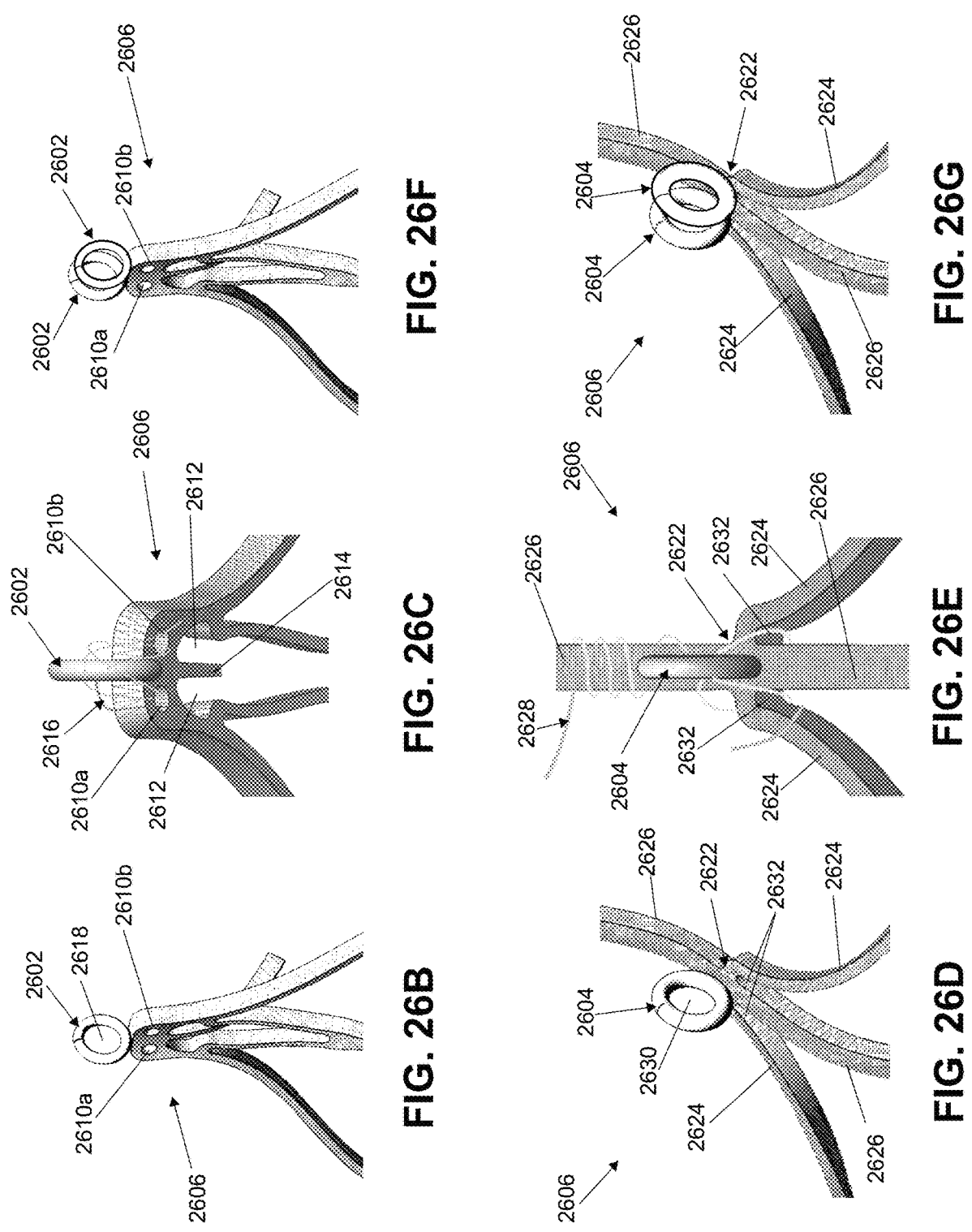
FIG. 26B is a schematic close-up view of a tether retention ring oriented at a ventricular end strut of the stent in FIG. 26A.
FIG. 26C depicts an exemplary suture attachment for attaching the tether retention ring in FIG. 26B to the strut.
FIG. 26D is a schematic close-up of a tether retention ring oriented at a strut junction in the atrial region of the stent in FIG. 26A.
FIG. 26E depicts an exemplary suture attachment for attaching the tether retention ring in FIG. 26D to the strut junction.
FIGS. 26F and 26G depict double or paired tether retention ring variants of FIGS. 26B and 26D, respectively.

FIG. 26A depicts another exemplary embodiment of suture or tether retention structures 2602, 2604 that may be coupled to a stent 2600. In this particular embodiment, a tether retention ring 2602 is provided on a distal tip 2606 of the outer wall 2608 of the stent 2600. Referring to FIGS. 26B and 26C, the distal tip 2606 may include one or more openings or apertures 2610*a*, 2610*b* to facilitate the attachment of the ring 2602. In other variations, however, the apertures 2610*a*-*b* may not be provided, and the recesses 2612 formed by the cavity surrounding the tissue barb 2614, depicted in FIG. 26C, may be used instead to attach the ring 2602. FIG. 26C depicts the use of a suture line 2616 to attach the ring 2602 to the distal tip 2606 using a criss-cross pattern where the suture line 2616 passes through one aperture 2610*a*, then crosses diagonally through the opening 2618 of the ring 2602, then through the other aperture 2610*b*, then diagonally through the opening 2618 of the ring 2602 in the opposite direction, and back again through the first aperture 2610*a*. This criss-cross routing may be provided 2 to 8 times, 2 to 6 times, 2 to 5 times, 2 to 4 times, or 2 or 3 times before the suture lines is knotted and cut to secure the ring 2602. Depending on the mechanical properties of the suture line and/or the number or routing passes used to attach the ring 2602, the ring 2602 may or may not be able to move, tilt or pivot relative to the distal tip 2606.

FIG. 26A also depicts another tether retention structure or ring 2604 located at a different location of the outer wall 2608, closer to the transition wall 2620 of the stent 2600. At this location, also depicted in FIG. 26D, the ring 2604 is located at the junction 2622 of the lateral struts 2624 and the longitudinal struts 2626 of the outer wall 2606. The routing of the suture 2628 may utilize attachment apertures provided in the stent strut as was depicted in FIGS. 26B and 26C, if any. In FIGS. 26D and 26E, however, no attachment apertures are provided, so the criss-cross routing of the suture 2628 between the junction 2622 and the opening 2630 of the ring 2618 may instead utilize the acutely angled grooves 2632 formed between the angled lateral struts 2624 and the longitudinal struts 2626. The criss-cross routing at this location may also be performed 2 to 8 times, 2 to 6 times, 2 to 5 times, 2 to 4 times, or 2 or 3 times before the suture lines is knotted and cut to secure the ring 2602. In addition, because of the availability of the surrounding struts 2624, 2626 at the junction 2622, the suture 2628 may also be optionally wrapped one or more times around one or more of the struts before, after or between the criss-cross routing patterns of the suture 2628. In the exemplary embodiment depicted in FIG. 26E, for example, the suture 2628 is wrapped three times around the longitudinal strut 2626 that is located away from the two angled lateral struts 2624 before routing in the criss-cross pattern.

In some variations, a single ring 2602, 2604 may be attached at each of the distal tips 2606 or junctions 2622 of the stent structure 2600. Depending on the arrangement or configuration of the tether lines used with the rings 2602 of the stent 2600, however, some locations may be provided with two rings 2602, 2604 rather than a single ring 2602, 2604, as depicted in FIGS. 26F and 26G. Alternatively, some distal tip 2606 or junctions 2622 may be provided with no ring at all. Two rings 2602, 2604 may be provided at a single distal tip 2606 or junction 2622 where the tether line loops away from the circumferential tether path, providing a narrower loop base. In other variations, a ring may not be provided or may be unused, if a broader loop base from two ring locations spaced are preferred. Potential arrangements and configurations While the embodiments herein have been particularly shown and described with references to embodiments thereof, it will be understood by those skilled in the art that various changes in form and details may be made therein without departing from the scope of the embodiments. For all of the embodiments described above, the steps of the methods need not be performed sequentially.

What is claimed is:

1. A stent assembly, comprising:
an expandable stent, the expandable stent comprising an arrangement of struts forming an outer wall, the outer wall comprising a first end region, a second end region and a middle region therebetween;
a plurality of tether retention structures arranged circumferentially around the first end region of the stent and defining a circumferential tether path;
a plurality of tether path locations uniformly spaced along the circumferential tether path, wherein each of the tether retention structures is located at one of the tether path locations and
a plurality of tether lines, wherein each tether line of the plurality of tether lines comprises a main region located along the circumferential tether path and a loop that loops away from the circumferential tether path between two tether retention structures, and wherein each tether line of the plurality of tether lines overlaps at least one other tether line of the plurality of tether lines along the circumferential tether path;
wherein the main region of each tether line of the plurality of tether lines comprises a first end region with a first end, and a second end region with a second end, and a middle region therebetween and containing its loop; and
wherein each tether retention structure that is fixedly attached to the first end or the second end of one of the tether lines is also slidably passed through by a different tether line.

2. The stent assembly of claim 1, wherein each first end and second end of each tether line is fixedly attached to one of the plurality of tether path locations, either directly to the outer wall or to a tether retention structure.

3. The stent assembly of claim 1, wherein each tether path location comprises at least one tether retention structure, and wherein at least one tether path location comprises two tether retention structures, wherein the middle region of one of the tether lines is configured to slidably pass through the two tether retention structures the loop of the one tether line loop away from the circumferential tether path between the two tether retention structures.

4. The stent assembly of claim 3, wherein the at least one tether path location comprising two tether retention structures comprises a plurality of tether path locations with two tether retention structures corresponding in number to the plurality of tether lines.

5. The stent assembly of claim 3, wherein each of the plurality of tether lines is configured to:
slidably pass through one of the plurality of tether retention structures without any other of the tether lines slidably passing through or attached thereto;
slidably pass through one of the plurality of tether retention structures along with another of the tether lines also slidably passing through; and
fixedly attached to two of the tether retention structures that are also slidably passed through by another of the tether lines.

6. The stent assembly of claim 5, wherein the number of tether path locations comprises twelve tether path locations.

7. The stent assembly of claim 6, wherein the twelve tether path locations are consecutive tether path locations comprising a first, second, third, fourth, fifth, sixth, seventh, eighth, ninth, tenth, eleventh and twelfth path locations, and wherein the fourth, eighth and twelfth tether path locations each comprises two first tether retention structures, and the first, second, third, fifth, sixth, seventh, ninth, tenth and eleventh tether path locations each comprises one first tether retention structure.

8. The stent assembly of claim 1, wherein each first end region and each second end region of each tether line slidably passes through at least one first tether retention structure at a tether path location that is different from the tether path location of the corresponding first end and second end, respectively.

9. The stent assembly of claim 1, wherein each of the plurality of tether path locations that is fixedly attached to the first end or the second end of one of the tether lines is not fixedly attached to any other tether lines.

10. The stent assembly of claim 1, wherein the number of tether path locations is a multiple of three and the plurality of tether lines comprises three tether lines.

11. The stent assembly of claim 1, wherein each tether line of the plurality of tether lines overlaps at least two other tether lines of the plurality of tether lines along the circumferential tether path.

12. The stent assembly of claim 1, wherein:
the plurality of tether retention structures are a plurality of first tether retention structures, and wherein the circumferential tether path is a first circumferential tether path;
the plurality of tether path locations are a plurality of first tether path locations; and
wherein the stent assembly further comprises:
a plurality of second tether retention structures arranged circumferentially around the second end region of the expandable stent and defining a second circumferential tether path;
a plurality of second tether path locations uniformly spaced along the second circumferential tether path, wherein each of the second tether retention structures is located at one of the first tether path locations, and wherein each second tether path location contains either no second tether retention structure, one second tether retention structure, or two second retention structures;
a plurality of second tether lines, wherein each second tether line of the plurality of second tether lines comprises a main region located along the circumferential tether path and a loop that loops away from the circumferential tether path between two tether retention structures.

13. The stent assembly of claim 12, wherein each second tether line of the plurality of second tether lines overlaps at least one other second tether line of the plurality of second tether lines along the second circumferential tether path.

14. The stent assembly of claim 12, wherein the main region of each tether line of the plurality of tether lines comprises a first end region with a first end, and a second end region with a second end, and a middle region therebetween and containing its loop.

15. The stent assembly of claim 14, wherein:

each first end and each second end of each second tether line is fixedly attached to one of the plurality of second tether path locations either directly to a strut of the outer wall, or a second tether retention structure.

16. The stent assembly of claim 12, wherein the plurality of second tether lines comprises a non-overlapping arrangement.

17. The stent assembly of claim 12, wherein the plurality of second tether lines comprises an overlapping arrangement.

18. The stent assembly of claim 12, wherein the relative configurations of the plurality of first tether retention structures and the plurality of first tether lines along the first circumferential tether path is identical to the relative configuration of the plurality of second tether retention structures and the plurality of second tether lines along the second circumferential tether path.

19. The stent assembly of claim 1, wherein each of the plurality of tether retention structures comprises an opening with a transverse or tangential orientation to the outer wall of the stent.

20. The stent assembly of claim 1, wherein each of the plurality of tether retention structures comprises rings, hoops or clips.

21. The stent assembly of claim 1, wherein each of the plurality of tether retention structures is fixedly attached or contiguously formed with the outer wall of the stent.

22. The stent assembly of claim 1, wherein each of the plurality of tether retention structures is movably or pivotably attached to the outer wall of the stent via sutures or wires.

23. The stent assembly of claim 1, wherein each of the plurality of tether path locations is located at a longitudinal strut of the arrangement of struts.

24. The stent assembly of claim 1, wherein at least one of the first end region and second end region of each tether line of the plurality of tether lines overlaps itself along the circumferential tether path.

* * * * *